United States Patent
Kirshenbaum et al.

(10) Patent No.: US 9,458,449 B2
(45) Date of Patent: Oct. 4, 2016

(54) HYBRID POLYMERS, PHARMACEUTICAL COMPOSITIONS AND METHODS OF SYNTHESIZING THE SAME

(71) Applicants: Kent Kirshenbaum, New York, NY (US); Paul Levine, Brooklyn, NY (US); Timothy Craven, Randolph, NJ (US)

(72) Inventors: Kent Kirshenbaum, New York, NY (US); Paul Levine, Brooklyn, NY (US); Timothy Craven, Randolph, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/282,228

(22) Filed: May 20, 2014

(65) Prior Publication Data

US 2015/0044189 A1     Feb. 12, 2015

Related U.S. Application Data

(60) Provisional application No. 61/825,240, filed on May 20, 2013.

(51) Int. Cl.

| C12N 9/96 | (2006.01) |
|---|---|
| C07K 1/02 | (2006.01) |
| C07K 1/13 | (2006.01) |
| C07K 5/083 | (2006.01) |

(52) U.S. Cl.
CPC ............... *C12N 9/96* (2013.01); *C07K 1/026* (2013.01); *C07K 1/13* (2013.01); *C07K 5/081* (2013.01); *C07K 5/0806* (2013.01)

(58) Field of Classification Search
None
See application file for complete search history.

(56) References Cited

U.S. PATENT DOCUMENTS

| 8,524,663 B2 | 9/2013 | Kirshenbaum et al. |
|---|---|---|
| 8,828,413 B2 | 9/2014 | Kirshenbaum et al. |
| 2012/0015883 A1 | 1/2012 | Sadowski et al. |
| 2014/0100354 A1 | 4/2014 | Kirshenbaum et al. |
| 2014/0113862 A1 | 4/2014 | Kirshenbaum et al. |
| 2015/0011465 A1 | 1/2015 | Kirshenbaum et al. |
| 2015/0044189 A1 | 2/2015 | Kirshenbaum et al. |
| 2015/0299254 A1 | 10/2015 | Kirshenbaum et al. |

FOREIGN PATENT DOCUMENTS

| WO | 2009139922 | 11/2009 |
|---|---|---|
| WO | 2010098843 | 9/2010 |
| WO | WO 2010/098843 | * 9/2010 |
| WO | 2013158600 | 10/2013 |

OTHER PUBLICATIONS

Patch et al., J. Am. Chem. Soc., 2003, 125, 12092-12093.*
Levine et al., Org. Biomol. Chem., 2013, 11, 4142-46.*
Ruijtenbeek et al., ChemBioChem, 2001, 2(3), 171-179.*
Li et al., "Salicylaldehyde ester-induced chemoselective peptide ligations: enabling generation of natural peptidic linkages at the serine/threonine sites", Org. Lett., 2010, 12:1724-1727.
Zhang et al., "Protein chemical synthesis by serine and threonine ligation", Proc. Natl. Acad. Sci., 2013, 110:6657-6662.
Horn et al., "Incorporation of chemoselective functionalities into peptoids via solid-phase submonomer synthesis", Bioconj. Chem. 2004, 15:428-435.
Murnen et al., "Impact of Hydrophobic Sequence Patterning on the Coil-to-Globule Transition of Protein-like Polymers", Macromolecules 2012, 45:5229-5236.
Yoo et al., "Protease-mediated ligation of abiotic oligomers", J. Am. Chem. Soc., 2005, 127:17132-3.
Lee et al., "Protein side-chain translocation mutagenesis via incorporation of peptoid residues", ACS Chem. Biol., 2011, 6, 1367-74.
Shah et al., "Oligo(N-aryl glycines): a new twist on structured peptoids", J. Am. Chem. Soc., 2008, 130:16622-32.
K. Kirshenbaum et al., "Sequence-specific polypeptoids: a diverse family of heteropolymers with stable secondary structure", Proc. Natl. Acad. Sci., 1998, 95:4303-4308.
Levine et al., "Chemoselective fragment condensation between peptide and peptidomimetic oligomers", Org. Biomol. Chem., 2013, 11:4142-4146.
Levine et al., "Semisynthesis of peptoid-protein hybrids by chemical ligation at serine", Organic Letters, 2014, 16:512-515.
Srinivas et al., "Peptidomimetic antibiotics target outer-membrane biogenesis in Pseudomonas aeruginosa", Science, 2010, 327:1010-1013.

* cited by examiner

*Primary Examiner* — James H Alstrum Acevedo
*Assistant Examiner* — Roy Teller
(74) *Attorney, Agent, or Firm* — Klauber & Jackson LLC

(57) ABSTRACT

Novel hybrid polymers are disclosed that have a structure represented by the following

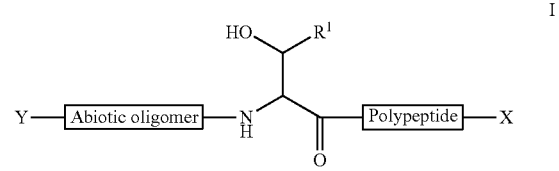

wherein Abiotic oligomer, Polypeptide, X, Y, and $R^1$ are as described herein. The methods to prepare the hybrid polymers via novel oxazolidinyl compounds are also described.

20 Claims, 15 Drawing Sheets

Fig. 3
9
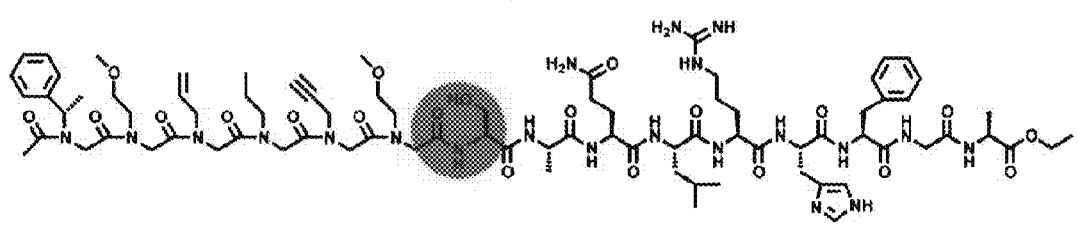
10
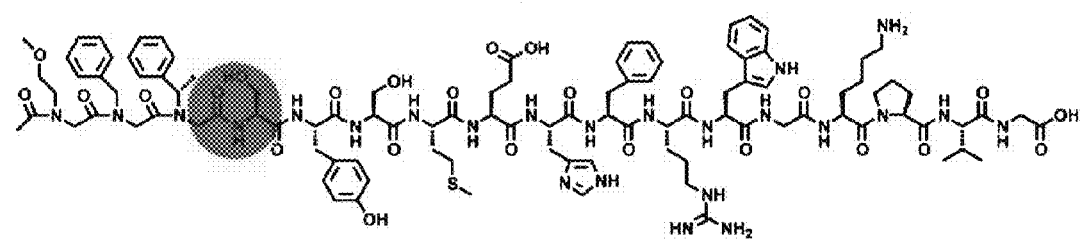

Fig. 8
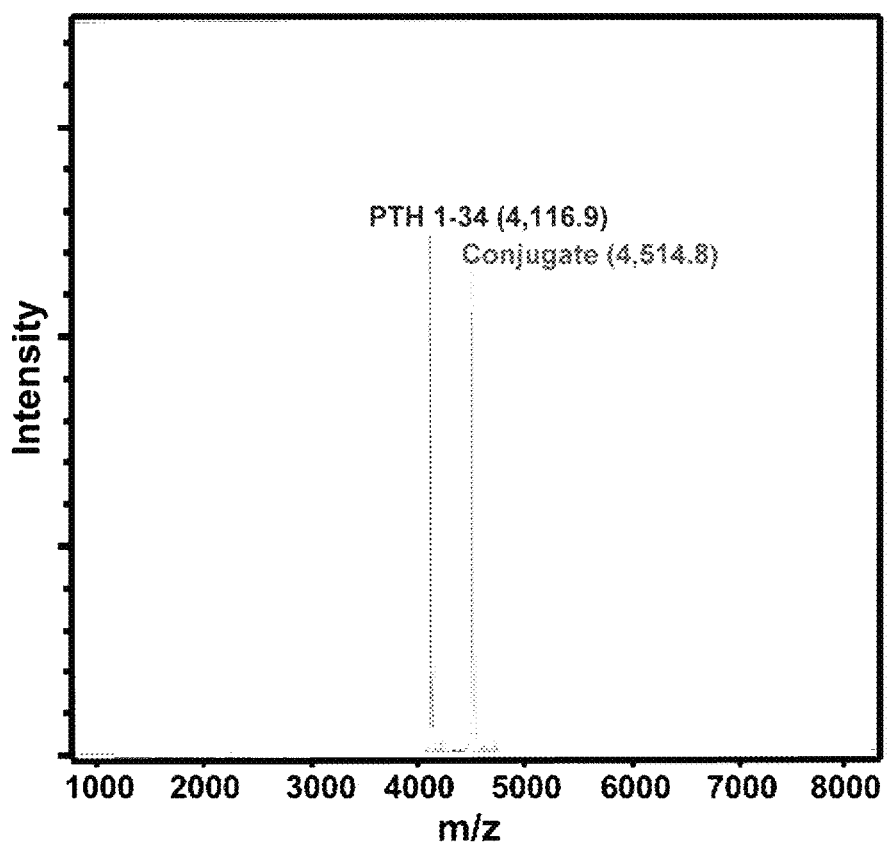
A
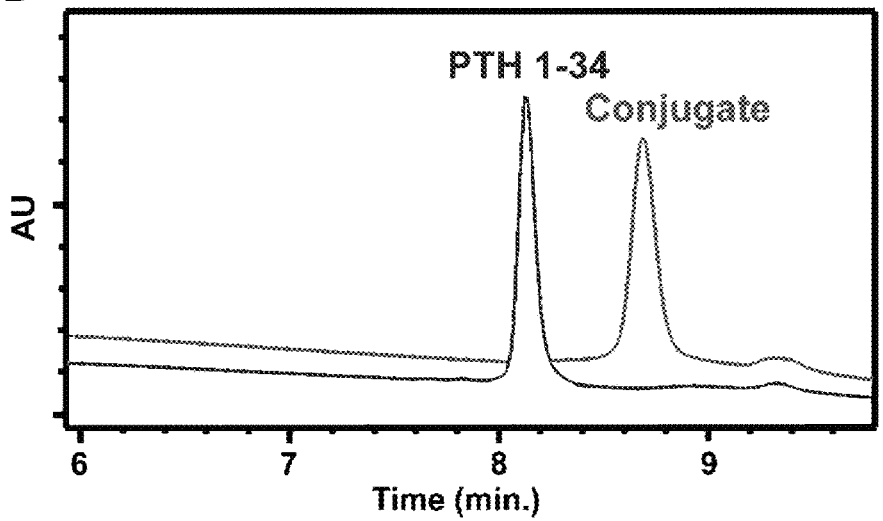
B

HYBRID POLYMERS, PHARMACEUTICAL COMPOSITIONS AND METHODS OF SYNTHESIZING THE SAME

CROSS REFERENCE TO RELATED APPLICATIONS

This application claims priority under 35 USC §119(e) from U.S. Provisional Application Ser. No. 61/825,240, filed May 20, 2013, which application is herein specifically incorporated by reference in its entirety.

GOVERNMENTAL SUPPORT

The research leading to the present invention was supported, at least in part, by National Science Foundation Award CHE-1152317. Accordingly, the Government has certain rights in the invention.

FIELD OF THE INVENTION

This invention relates to novel hybrid polymers. The invention also relates to novel methods for the preparation of the hybrid polymers. This invention further relates to novel oxazolidine compounds and use thereof in preparation of the hybrid polymers.

BACKGROUND OF THE INVENTION

Polypeptides, which are natural oligomers, while capable of exhibiting an extraordinary range of bioactivities, often display poor pharmacological properties. For this reason, synthetic mimics of peptides have been the focus of vigorous development by medicinal and bioorganic chemists. A variety of oligomeric peptidomimetics have been introduced that show potential as partial mimics of natural polypeptide species in that they exhibit some of the structural and functional attributes of natural polypeptides (Patch et al., Curr. Opin. Chem. Biol., 2002, 6, 872). Further elaboration of peptidomimetic structures may lead to a greater range of capabilities for these compounds.

In the field of peptidomimetics research, extensive efforts have been made to recapitulate the structural features present in naturally occurring bioactive peptides (Ripka et al. Curr. Opin. in Chem. Bio. 1998, 2, 441-452; Steer et al. Curr. Med. Chem. 2002, 9, 811-822; Patch et al. Curr. Opin. In Chem. Biol. 2002, 6, 872-877). Many functional peptidomimetics such as magainin mimics (Liu et al. J. Am. Chem. Soc. 2001, 123, 7553-7559; Wieprecht et al. Biochemistry 1996, 35, 10844-10853; Porter et al. J. Am. Chem. Soc. 2005, 127, 11516-11529; Numao et al. Biol. Pharm. Bull. 1997, 20, 800-804; Rennie et al. J. Ind. Microbiol. Biotechnol. 2005, 32, 296-300), integrin mimics (Pasqualini et al. J. Cell Biol. 1995, 130, 1189-1196; Scarborough et al. Curr. Med. Chem. 1999, 6, 971-981) and somatostatin mimics (Gademann et al. J. Med. Chem. 2001, 44, 2460-2468; Gademann et al. Helv. Chim. Acta 2000, 83, 16-33) highlight the significance of structural mimicry for their function. More recently, efforts have been made to enhance the conformational ordering of peptidomimetic oligomers (Fink et al. J. Am. Chem. Soc. 1998, 120, 4334-4344; Phillips et al. J. Am. Chem. Soc. 2002, 124, 58-66; Abell et al. Lett. Pept. Sci. 2001, 8, 267-272; Clark et al. J. Am. Chem. Soc. 1995, 117, 12364-12365; Dimartino et al. Org. Lett. 2005, 7, 2389-2392). Stabilizing or rigidifying polymer conformations may lead to enhanced binding affinities (Sewald et al., Peptides: Chemistry and Biology. Wiley-VCH: Weinheim, Germany: 2002; Wipf Chem. Rev. 1995, 95, 2115-2134). To this end, several methods have been developed to enhance the conformational ordering of non-natural polymers (Sewald et al., Peptides: Chemistry and Biology. Wiley-VCH: Weinheim, Germany: 2002; Wipf Chem. Rev. 1995, 95, 2115-2134; Holub et al. Org. Lett. 2007, 9, 3275-3278). These methods include the introduction of both covalent and non-covalent intramolecular interactions. Some examples of covalent constraints include site-specific macrocyclization via Huisgen 1,3-dipolar cycloaddition (Holub et al. Org. Lett. 2007, 9, 3275-3278), head-to-tail macrocyclization (Gademann et al. Angew. Chem., Int 1999, 38, 1223-1226; Robinson et al. Bioorg. Med. Chem. 2005, 13, 2055-2064; Wels et al. Bioorg. Med. Chem. Lett. 2005, 15, 287-290; Shankaramma et al. Chem. Commun. 2003, 1842-1843; Locardi et al. J. Am. Chem. Soc. 2001, 123, 8189-8196; Chakraborty et al. J. Org. Chem. 2003, 68, 6257-6263; Angell et al. J. Org. Chem. 2005, 70, 9595-9598; Norgren et al. J. Org. Chem. 2006, 71, 6814-6821; Clark et al. J. Am. Chem. Soc. 1998, 120, 651-656; Yuan et al. J. Am. Chem. Soc. 2004, 126, 11120-11121; Nnanabu et al. Org. Lett. 2006, 8, 1259-62; Jiang et al. Org. Lett. 2004, 6, 2985-2988; Mann et al. Org. Lett. 2003, 5, 4567-4570; Wels et al. Org. Lett. 2002, 4, 2173-2176; Bru et al. Tetrahedron Lett. 2005, 46, 7781-7785; Vaz et al. Org. Lett. 2006, 8, 4199-4202; Buttner et al. Chem. Eur. l 2005, 11, 6145-6158; Royo et al. Tetrahedron Lett. 2002, 43, 2029-2032) and generation of hydrogen bond surrogates via metathesis reactions (Dimartino et al. Org. Lett. 2005, 7, 2389-2392).

Peptoids, for example, are a class of peptidomimetics which comprise N-substituted glycine monomer units (Figliozzi et al, Synthesis of N-substituted glycine peptoid libraries. In Methods Enzymol., Academic Press: 1996; Vol. 267, pp 437-447; Bartlett et al., Proc. Natl. Acad. Sci. U.S.A. 1992, 89, 9367-9371). Peptoids are an important class of sequence-specific peptidomimetics shown to generate diverse biological activities (Patch et al. In Pseudo peptides in Drug Development; Nielson, P. E., Ed.; Wiley-VCH: Weinheim, Germany, 2004; pp 1-35; Miller et al. Drug Dev. Res. 1995, 35, 20-32; Murphy et al. Proc. Natl. Acad. Sci. U.S.A. 1998, 95, 1517-1522; Nguyen et al. Science 1998, 282, 2088-2092; Ng et al. Bioorg. Med. Chem. 1999, 7, 1781-1785; Patch et al. J. Am. Chem. Soc. 2003, 125, 12092-12093; Wender et al. Proc. Natl. Acad. Sci. U.S.A. 2000, 97, 13003-13008; Wu et al. Chem. Biol. 2003, 10, 1057-1063; Chongsiriwatana et al. Proc. Natl. Acad. Sci. U.S.S. 2008, 105, 2794-2799). Oligopeptoids can be designed to display chemical moieties analogous to the bioactive peptide side chains while their abiotic backbones provide protection from proteolytic degradation.

Peptoid sequences comprised of bulky chiral side chains have the capacity to adopt a stable helical secondary structure, although some conformational heterogeneity is evident in solution (Armand et al. Proc. Natl. Acad. Sci. U.S.A. 1998, 95, 4309-4314; Kirshenbaum et al. Proc. Natl. Acad. Sci. U.S.A. 1998, 95, 4303-4308; Wu et al. J. Am. Chem. Soc. 2003, 125, 13525-13530). The crystal structure of a linear peptoid homopentamer composed of bulky chiral side chains exhibits a helical conformation resembling that of a polyproline type I helix (Armand et al. Proc. Natl. Acad. Sci. U.S.A. 1998, 95, 4309-4314; Kirshenbaum et al. Proc. Natl. Acad. Sci. U.S.A. 1998, 95, 4303-4308; Wu et al. J. Am. Chem. Soc. 2003, 125, 13525-13530). Oligopeptoid sequences incorporating repeating units of two bulky chiral side chains and a cationic side chain form facially amphiphilic helical structures. Recent studies describe antimicrobial activities generated from facially amphiphilic helical peptoids (Patch et al. *J. Am. Chem. Soc.* 2003, 125, 12092-12093; Chongsiriwatana et al. *Proc. Natl. Acad. Sci. U.S.S.* 2008, 105, 2794-2799). These peptoid oligomers are reported to be good functional mimics of maganin-2 amide, a peptide antimicrobial agent from Xenopus skin (Patch et al. *J. Am. Chem. Soc.* 2003, 125, 12092-12093; Zasloff. *Proc. Natl. Acad. Sci. USA* 1987, 84, 5449-5453).

SUMMARY OF THE INVENTION

In one aspect, the present invention provides sequence-specific oligomers, polymers and hybrid hybrid polymers comprising an abiotic oligomer segment and a polypeptide segment.

The hybrid polymers of the invention have potential to exhibit many advantageous characteristics for development of bioactive compounds, as they:
are amenable to efficient solid phase synthesis;
can incorporate highly diverse chemical functionalities;
can establish a relationship between oligomer sequence, three-dimensional structure, and function;
do not require the presence of chiral centers;
can demonstrate marked resistance to degradation;
have superior cell permeability characteristics relative to natural polypeptides; and can manifest rapid bioactivities.

In certain aspects, the present invention provides sequence-specific oligomers, polymers and hybrid hybrid polymers comprising an abiotic oligomer segment and a polypeptide segment, and wherein the polypeptide segment comprises at least one serine or threonine residue at its N-terminus, and the abiotic oligomer segment is bonded to the polypeptide through the serine or the threonine residue.

More particularly, the present invention relates to hybrid polymers according to formula I:

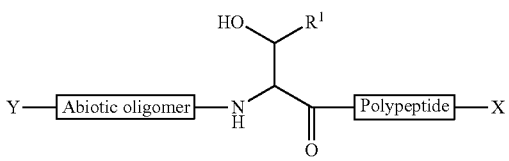

or a pharmaceutically acceptable salt, stereoisomer, isotopic variant or tautomer thereof,
wherein
Polypeptide is as described herein;
Abiotic oligomer is selected from oligomers comprising N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas, and combinations thereof;
the group

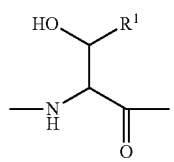

is a serine or threonine residue;

X is hydroxyl, alkoxy, amino or substituted amino;
Y is H or acetyl; and
$R^1$ is H or methyl.

In one embodiment, the abiotic oligomer is selected from beta-amino acid oligomers, gamma-amino acid oligomers, peptoids such as N-substituted glycine oligomers, beta peptoids such as N-substituted beta-alanine oligomers, oligoureas, oligophenyleneethynylenes, peptide nucleic acids (PNAs), and combinations thereof.

In particular aspects, the present invention provides hybrid polymers according to formula II:

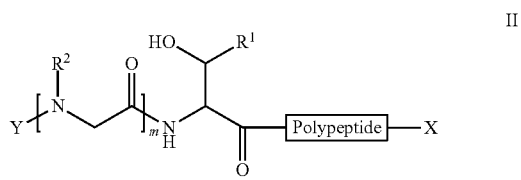

or a pharmaceutically acceptable salt, stereoisomer, isotopic variant or tautomer thereof;
wherein
X is hydroxyl, alkoxy, amino or substituted amino;
Y is H or acetyl;
$R^1$ is H or methyl;
each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
the subscript m is an integer from 2-200.

In more particular aspects, the present invention provides hybrid polymers wherein the hybrid polymer is according to formula III:

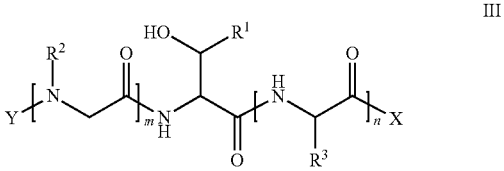

or a pharmaceutically acceptable salt, stereoisomer, isotopic variant or tautomer thereof;
wherein
X is hydroxyl, alkoxy, amino or substituted amino;
Y is H or acetyl;
$R^1$ is H or methyl;
each $R^2$ and $R^3$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl; and
the subscript m is an integer from 2-200; the subscript n is an integer from 2-1000.

In yet another aspect, the present invention provides, processes for preparing hybrid polymer according to formula I.

In one embodiment, the process comprises the steps of
A1) reacting the compound of formula SI-1 with salicylaldehyde of formula SI-2

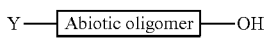
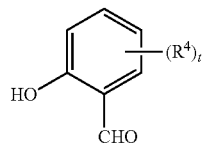

to form a compound of formula SI-3:

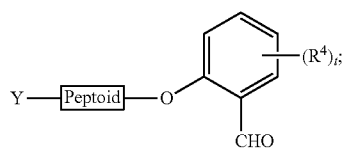

A2) reacting the compound of formula SI-3 with a polypeptide of formula SI-4

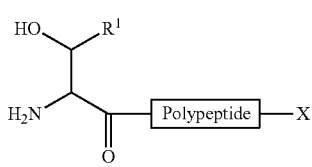

to form the oxazolidine compound of formula SI-5:

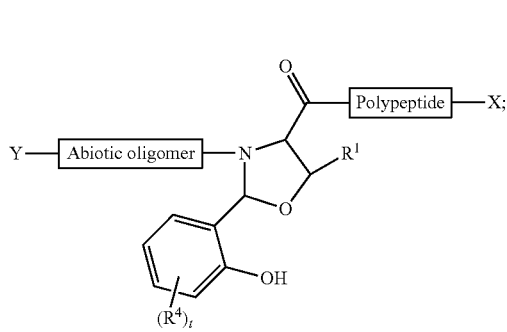

and

A3) reacting the oxazolidine compound of formula SI-5 with an acid to form the hybrid polymer of formula I; and
wherein Polypeptide, Abiotic oligomer, X, Y, $R^4$ and t are as described herein.

In yet another aspect, the present invention provides, processes for preparing hybrid polymer according to formula III:

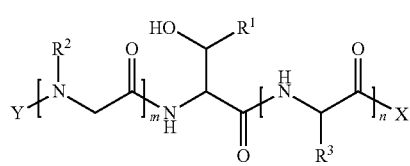

or a pharmaceutically acceptable salt, stereoisomer, isotopic variant or tautomer thereof;

comprising the steps of

B1) reacting the compound of formula SI-1-1 with salicylaldehyde of formula SI-2

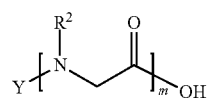

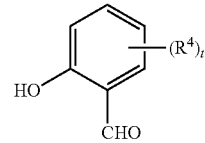

to form a compound of formula SI-3-1:

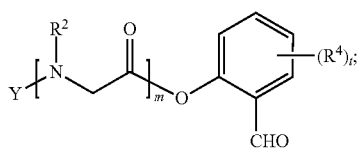

B2) reacting the compound of formula SI-3-1 with a peptide of formula SI-4-1

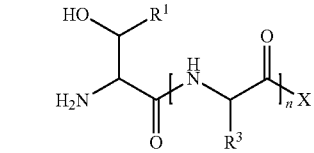

to form the oxazolidine compound of formula SI-5-1:

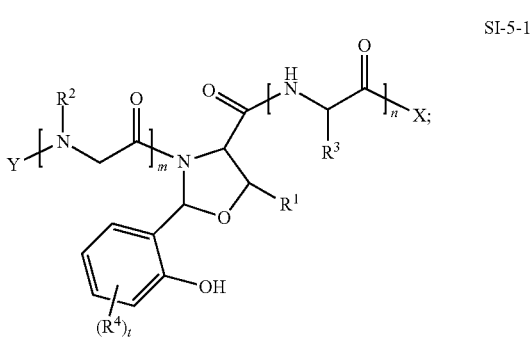

and

B3) reacting the oxazolidine compound of formula SI-5-1 with an acid to form the hybrid polymer of formula III;
wherein X, Y, $R^1$, $R^2$, $R^3$, $R^4$, m, n, and t are as described herein.

In yet another aspect, the present invention provides, oxazolidine compounds according to formula SI-5:

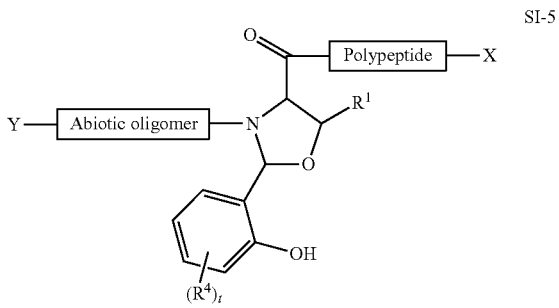

or a stereoisomer, or a tautomer thereof;

Polypeptide is as described herein;

Abiotic oligomer is selected from oligomers comprising N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas, and combinations thereof;

X is hydroxyl, alkoxy, amino or substituted amino;

Y is H or acetyl;

$R^1$ is H or methyl;

each $R^4$ is independently H or substituted or unsubstituted alkyl.

In one embodiment, the abiotic oligomer is selected from beta-amino acid oligomers, gamma-amino acid oligomers, peptoids such as N-substituted glycine oligomers, beta peptoids such as N-substituted beta-alanine oligomers, oligoureas, oligophenyleneethynylenes, peptide nucleic acids (PNAs), and combinations thereof.

In yet another aspect, the present invention provides, oxazolidine compounds according to formula SI-5-1:

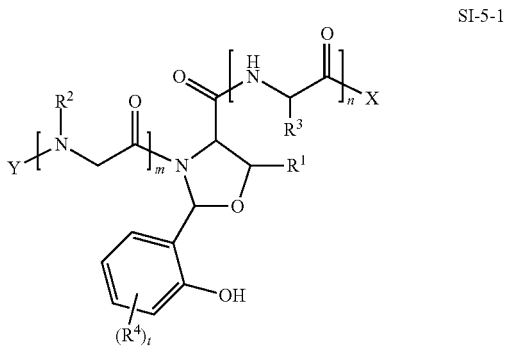

or a stereoisomer, or a tautomer thereof; and
wherein X, Y, $R^1$, $R^2$, $R^3$, $R^4$, m, n, and t are as described herein.

In additional aspects, this invention provides methods for synthesizing the oligomers of the invention, with representative synthetic protocols and pathways disclosed later on herein.

Other objects and advantages will become apparent to those skilled in the art from a consideration of the ensuing detailed description, which proceeds with reference to the following illustrative drawings.

BRIEF DESCRIPTION OF THE DRAWINGS

FIG. 3 shows chemical structures of peptoid-peptide hybrids 9 (ligation product between peptoid 6 and peptide 7) and 10 (ligation product between peptoid 2 and peptide 8). Red circle indicates native amide linkage.

FIG. 8 shows characterization of ligation between PTH (1-34) and a peptide containing a C-terminal salicylaldehyde ester. (A) MALDITOF analysis of purified PTH (1-34) (Forteo) before (blue) and after ligation (red). (B) Analytical HPLC analysis of purified PTH (1-34) (blue) and purified PTH conjugate (red). Upper trace of PTH conjugate offset in y-direction for clarity. AU indicates absorbance units.

DETAILED DESCRIPTION OF THE INVENTION

Definitions

Figure 1:
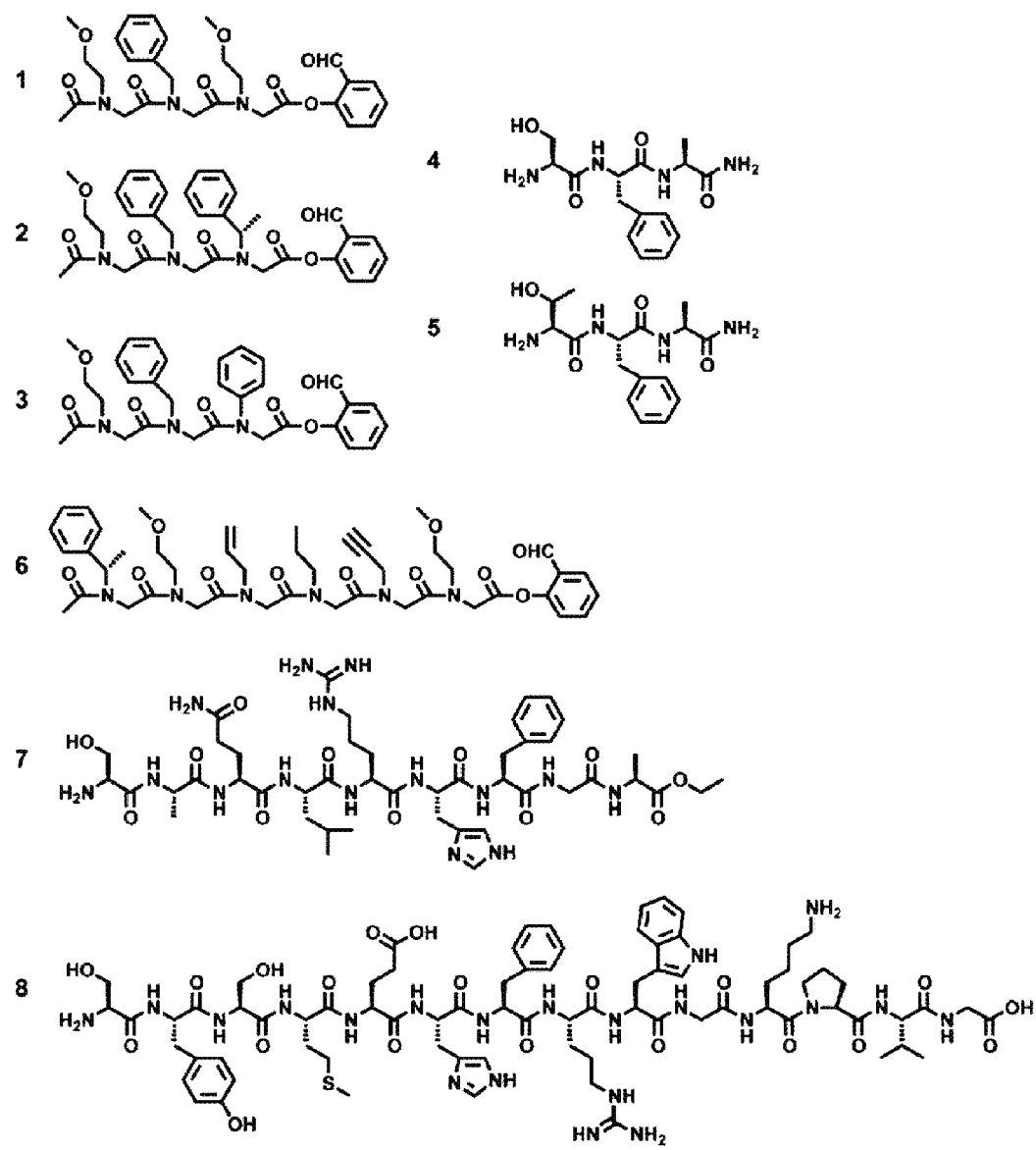
FIG. 1 presents a library of peptoid and peptide fragments utilized in chemoselective fragment condensation reactions.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Abiotic' refers to an unnatural, sequence-specific, or non-natural monomer and/or oligomer unit. This includes chemical fragments that are not present in natural biological systems or living organisms. Abiotic oligomers include monomer units that would not be present in biopolymers synthesized in natural living systems, such as nucleotides present in natural nucleic acids; carbohydrates present in natural polysaccharides; or L- and D-alpha amino acids present in natural polypeptides.

'Oligomer' refers to a unit comprising a linear chain of two or more linked monomers. More specifically, an 'oligomer' of the invention is between 2-100 monomers, more particularly between 2-50 or 2-20.

'Abiotic oligomers' refers to oligomers comprising N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas. Exemplary monomers include, for example, individual amino acid residues (monomeric units of polypeptides), N-substituted glycines (monomeric units of peptoids), N-substituted beta-alanine (monomeric units of beta-peptoids), aminoxy acids, and monomers comprising the aforementioned exemplary oligomers.

'Acyl' or 'Alkanoyl' refers to a radical —C(O)R$^{20}$, where R$^{20}$ is hydrogen, C$_1$-C$_8$ alkyl, C$_3$-C$_{10}$ cycloalkyl, C$_3$-C$_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—C$_1$-C$_8$ alkyl, —C(O)—(CH$_2$)$_t$(C$_6$-C$_{10}$aryl), —C(O)—(CH$_2$)$_t$(5-10 membered heteroaryl), —C(O)—(CH$_2$)$_t$(C$_3$-C$_{10}$cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently C$_1$-C$_8$ alkyl, substituted with halo or hydroxy; or C$_3$-C$_{10}$ cycloalkyl, 4-10 membered heterocycloalkyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Alkoxy' refers to the group —OR$^{29}$ where R$^{29}$ is C$_1$-C$_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl, n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and iso-amyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a C$_1$-C$_8$ alkyl group substituted with halo, cyano, nitro, trifluoromethyl, trifluoromethoxy, azido, —NR'"SO$_2$R", —SO$_2$NR"R'", —C(O)R", —C(O)OR", —OC(O)R", —NR'"C(O)R", —C(O)NR"R'", —NR"R'", or —(CR"R"")$_m$OR'"; wherein each R" is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Each of R" and R'" independently represents H or C$_1$-C$_8$ alkyl.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

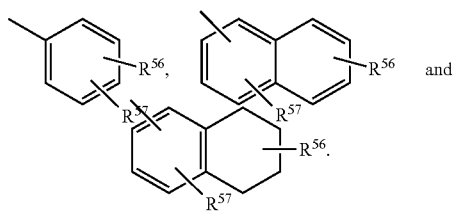

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocycloalkyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O or S. $R^{60}$ and $R^{61}$ are independently hydrogen, C1-C8 alkyl, C1-C4 haloalkyl, C3-C10 cycloalkyl, 4-10 membered heterocycloalkyl, C6-C10 aryl, substituted aryl, 5-10 membered heteroaryl.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

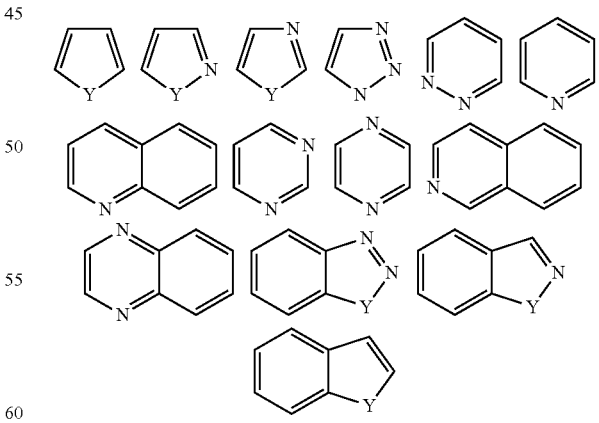

wherein each Y is selected from carbonyl, N, $NR^{65}$, O and S; and $R^{65}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative aryl having hetero atoms containing substitution include the following:

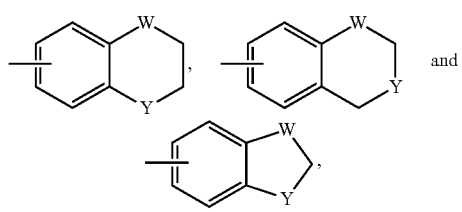

wherein each W is selected from $C(R^{66})_2$, $NR^{66}$, O and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

"Unnatural amino acids" means amino acids and corresponding peptoid oligomers that are synthesized from single amino acid starting materials. Such unnatural amino acids may be prepared and used individually in accordance with the present invention, or may be incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, Science, 244: 182-188 (April 1989).

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "patient" and "subject" are used interchangeably herein. Accordingly, a subject can be a mammal, in a particular embodiment a human, or a bird, a reptile, an amphibian, or a plant.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2$H or D), carbon-13 ($^{13}$C), nitrogen-15 ($^{15}$N), or the like. It will be understood that, in a compound comprising an unnatural proportion of an isotope, any example of an atom where present, may vary in isotope composition. For example, any hydrogen may be $^2$H/D, or any carbon may be $^{13}$C, or any nitrogen may be $^{15}$N, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and a $^{13}$N, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The Novel Hybrid Polymers

As set forth earlier herein, the present invention provides sequence-specific oligomers, polymers and hybrid hybrid polymers comprising an abiotic oligomer segment and a polypeptide segment.

The hybrid polymers of the invention may exhibit many advantageous characteristics for development of bioactive compounds, as they:
are amenable to efficient solid phase synthesis;
can incorporate highly diverse chemical functionalities;
can establish a relationship between oligomer sequence, three-dimensional structure, and function;
do not require the presence of chiral centers;
can demonstrate marked resistance to degradation;
have superior cell permeability characteristics relative to natural polypeptides; and can manifest rapid bioactivities.

Some of the advantageous properties of hybrid polymers such as peptidomimetics for use as antibiotics are described in Srinivas et al. (*Science* 2010, 327, 1010-1013), which is incorporated herein in its entirety.

In certain aspects, the present invention provides sequence-specific oligomers, polymers and hybrid hybrid polymers comprising an abiotic oligomer segment and a polypeptide segment, and wherein the polypeptide segment comprises at least one serine or threonine residue at its N-terminus, and the abiotic oligomer segment is bonded to the polypeptide through the serine or the threonine residue.

In one embodiment, the polypeptide segment comprises a protein, and wherein the protein comprises at least one serine or threonine residue at its N-terminus.

In one embodiment, the polypeptide segment is a long peptide chain. In another embodiment, the polypeptide segment comprises more than 100 amino acids.

In one embodiment, the polypeptide segment is a protein. In another embodiment, the polypeptide segment comprises between 50-100 amino acids.

In one embodiment, the polypeptide segment is a short peptide chain. In another embodiment, the polypeptide segment comprises fewer than 50 amino acids.

In another embodiment, the polypeptide, comprises amino acid residues; and the amino acid residues are selected from one or more glycine, L-lysine, L-cysteine, L-aspartic acid, L-asparagine, L-glutamine, L-alanine, L-valine, L-leucine, L-iso-leucine, L-tyrosine, L-proline, L-serine, L-threonine, L-glutamic acid, L-tryptophan, L-phenylalanine, L-methionine, L-arginine, and L-histidine residues.

In another embodiment, the polypeptide segment is a bovine pancreatic reibonulcease A (RNase A) residue. In yet another embodiment, the polypeptide segment is S-peptide residue; and wherein the S-peptide is N-terminal portion (residues 1-20) of RNase A.

In another embodiment, the polypeptide segment is a parathyroid hormone 1-34 or PTH (1-34) polypeptide.

In one embodiment, the abiotic oligomer segment comprises N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas, and combinations thereof.

In another embodiment, the abiotic oligomer segment comprises beta-amino acid oligomers, gamma-amino acid oligomers, peptoids such as N-substituted glycine oligomers, beta peptoids such as N-substituted beta-alanine oligomers, oligoureas, oligophenyleneethynylenes, peptide nucleic acids (PNAs), or combinations thereof. In another embodiment, the abiotic oligomer comprises beta-amino acid oligomers, or gamma-amino acid oligomers. In yet another embodiment, the abiotic oligomer comprises peptoids such as N-substituted glycine oligomers. In another embodiment, the abiotic oligomer comprises beta peptoids such as N-substituted beta-alanine oligomers. In yet another embodiment, the abiotic oligomer comprises oligoureas, oligophenyleneethynylenes, or peptide nucleic acids (PNAs), or any combinations thereof.

In one embodiment, with respect to the hybrid polymers of the invention, the hybrid polymer is other than compounds HP1-HP6. The CAS Registry number and/or the chemical name and/or the structure of the compounds HP1-HP6 are given below:

Compound HP1

CAS Registry number—1256287-75-8

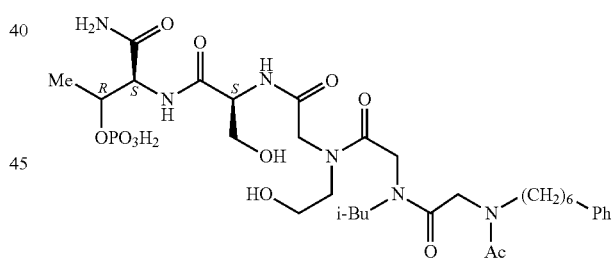

Compound HP2

CAS Registry number—1256287-74-7

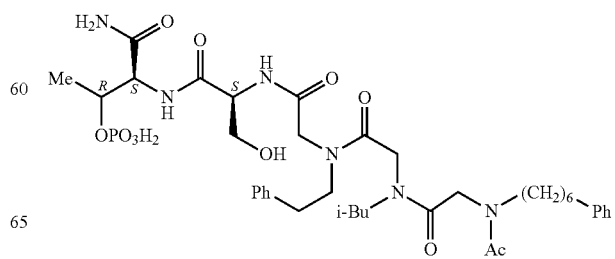

Compound HP3
CAS Registry number—1256287-73-6

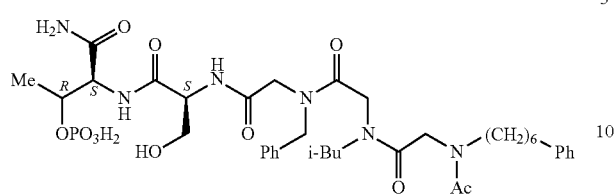

Compound HP4
CAS Registry number—339306-12-6
Name—L-Leucinamide, N-acetyl-N-[[4-(phosphonooxy)phenyl]methyl]glycyl-N-(2-carboxyethyl)glycyl-L-threonyl- Compound HP5
CAS Registry number—210833-50-4
Name—Glycine, N-(1-methylpropyl)glycyl-N-(phenylmethyl)glycyl-N-(1-methylpropyl)glycyl-N-[4-[aminoiminomethyl]amino]butyl]glycyl-L-threonylglycylglycylglycylglycyl-

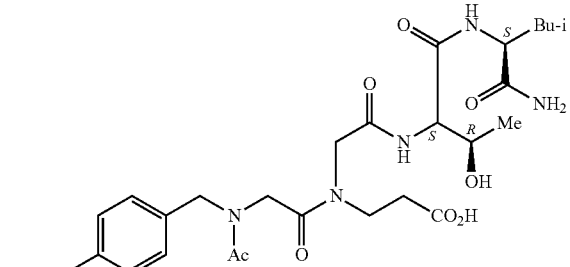

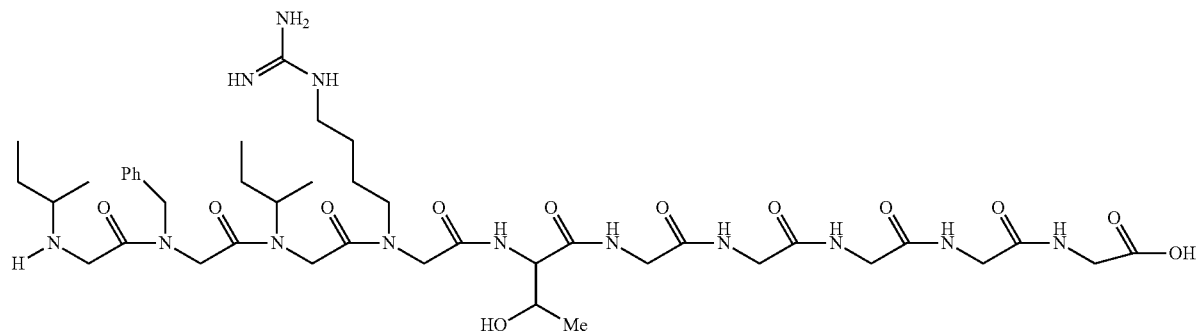 [SMILES: CCC(C)NCC(=O)N(CC(=O)N(CC(=O)N(CCCCNC(=N)N)CC(=O)NC(C(=O)NCC(=O)NCC(=O)NCC(=O)NCC(=O)NCC(=O)O)C(C)O)C(C)CC)Cc1ccccc1]

Compound HP6
CAS Registry number—204516-40-5
Name—L-Serinamide, N-(phenylmethyl)glycyl-L-prolyl-N-(phenylmethyl)glycyl-N-[2-(1H-indol-3-yl)ethyl]glycyl-L-seryl-L-seryl-.

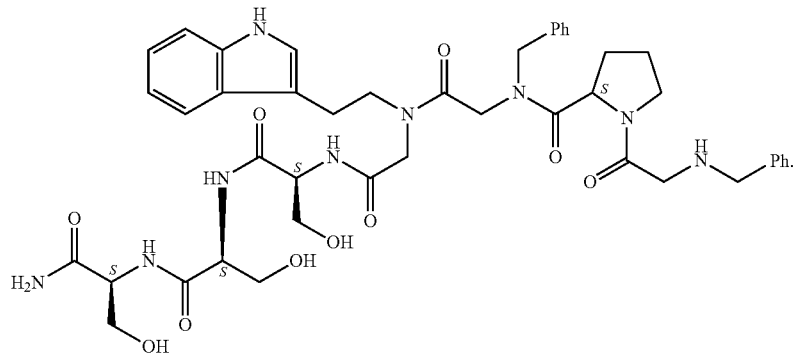

In certain aspects, the present invention provides hybrid polymers according to formula I:

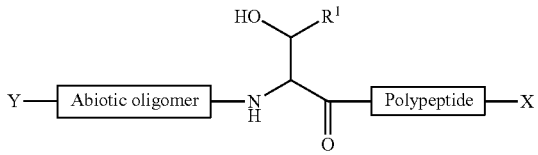

I or a pharmaceutically acceptable salt, stereoisomer, isotopic variant or tautomer thereof;
wherein
Polypeptide is as described herein;
Abiotic oligomer is as described herein;
the group

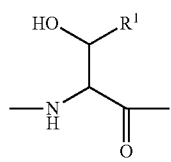

is a serine or threonine residue;
X is hydroxyl, alkoxy, amino or substituted amino;
Y is H or acetyl; and
$R^1$ is H or methyl.

In one embodiment, the abiotic oligomer comprises beta-amino acid oligomers.

In one embodiment, the abiotic oligomer comprises gamma-amino acid oligomers.

In one embodiment, the abiotic oligomer comprises peptoids such as N-substituted glycine oligomers.

In one embodiment, the abiotic oligomer comprises peptoids such as N-substituted beta-alanine oligomers.

In one embodiment, the abiotic oligomer comprises oligoureas.

In one embodiment, the abiotic oligomer comprises oligophenyleneethynylenes.

In one embodiment, the abiotic oligomer comprises peptide nucleic acids (PNAs).

In one embodiment, the abiotic oligomer comprises any combinations of abiotic oligomer selected from a group consisting of beta-amino acid oligomers, gamma-amino acid oligomers, peptoids such as N-substituted glycine oligomers, beta peptoids such as N-substituted beta-alanine oligomers, oligoureas, oligophenyleneethynylenes, and peptide nucleic acids (PNAs).

In one embodiment, the terminal nitrogen of the abiotic oligomer is attached to Y; and the terminal carbonyl carbon, —C(=O)—, of the abiotic oligomer is attached to the nitrogen of the serine or threonine residue.

In certain aspects, the present invention provides hybrid polymers according to formula II:

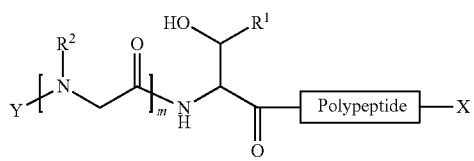

II or a pharmaceutically acceptable salt, stereoisomer, isotopic variant or tautomer thereof;
wherein
Polypeptide is as described herein;
X is hydroxyl, alkoxy, amino or substituted amino;
Y is H or acetyl;
$R^1$ is H or methyl;
each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl; and the subscript m is an integer from 2-200.

In one embodiment, with respect to the hybrid polymers according to formula I or II, the polypeptide is a long peptide chain. In one embodiment, the polypeptide comprises more than 100 amino acids residues.

In one embodiment, the polypeptide is a protein. In another embodiment, the polypeptide comprises between 50-100 amino acid residues.

In one embodiment, the polypeptide is a short peptide chain. In another embodiment, the polypeptide comprises fewer than 50 amino acid residues.

In one embodiment, with respect to the hybrid polymers according to formula I or II, the polypeptide, comprises amino acid residues; and the amino acid residues are selected from one or more glycine, L-lysine, L-cysteine, L-aspartic acid, L-asparagine, L-glutamine, L-alanine, L-valine, L-leucine, L-iso-leucine, L-tyrosine, L-proline, L-serine, L-threonine, L-glutamic acid, L-tryptophan, L-phenylalanine, L-methionine, L-arginine, and L-histidine residues.

In one embodiment, the polypeptide is a protein.
In one embodiment, the polypeptide is PTH (1-34).
In one embodiment, the polypeptide is a S-protein or S-peptide.

In certain aspects, the present invention provides hybrid polymers, wherein the hybrid polymer is according to formula III:

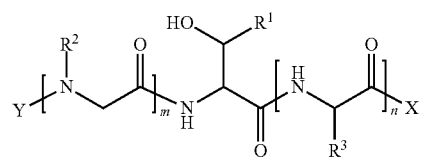

III or a pharmaceutically acceptable salt, stereoisomer, isotopic variant or tautomer thereof;
wherein
X is hydroxyl, alkoxy, amino or substituted amino;
Y is H or acetyl;
$R^1$ is H or methyl;
each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
each $R^3$ is independently selected from a group consisting of H, substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
the subscript m is an integer from 2-200; and the subscript n is an integer from 2-1000.

In one embodiment, with respect to the hybrid polymers of the invention, the hybrid polymer is other than HP1, HP2, HP3, HP4, HP5, or HP6.

In one embodiment, with respect to the hybrid polymers of formula I, II, or III, $R^1$ is H. In another embodiment, $R^1$ is Me.

In one embodiment, with respect to the hybrid polymers of formula II, or III, $R^2$ is other than phenylhexyl.

In one embodiment, with respect to the hybrid polymers of formula II, or III, each of $R^2$ is independently Me, Et, n-Pr, i-Pr, n-Bu, sec-Bu, or i-Bu.

In one embodiment, with respect to the hybrid polymers of formula II, or III, each of $R^2$ is independently phenyl or benzyl, unsubstituted or substituted with one or more groups selected from alkyl, halo, hydroxy, amino, nitro, and alkoxy.

In one embodiment, with respect to the hybrid polymers of formula II, or III, each of $R^2$ is independently phenethyl, unsubstituted or substituted with one or more groups selected from alkyl, halo, hydroxy, amino, nitro, and alkoxy.

In one embodiment, with respect to the hybrid polymers of formula II, or III, each of $R^2$ is independently 2-naphthyl, unsubstituted or substituted with one or more groups selected from alkyl, halo, hydroxy, amino, nitro, and alkoxy.

In one embodiment, with respect to the hybrid polymers of formula II, or III, each of $R^2$ is independently 2,2-diphenylethyl, unsubstituted or substituted with one or more groups selected from alkyl, halo, hydroxy, amino, nitro, and alkoxy.

In one embodiment, with respect to the hybrid polymers of formula II, or III, each of $R^2$ is independently furanyl or thienyl, unsubstituted or substituted with one or more groups selected from alkyl, halo, hydroxy, amino, nitro, and alkoxy.

In one embodiment, with respect to the hybrid polymers of formula II, or III, each of $R^2$ is independently aminomethyl, 2-aminoethyl, 3-aminopropyl, 4-aminobutyl, 5-aminopentyl, or 6-aminohexyl.

In one embodiment, with respect to the hybrid polymers of formula II, or III, each of $R^2$ is independently 3-aminopropyl.

In one embodiment, with respect to the hybrid polymers of formula II, or III, each of $R^2$ is independently guanidinoalkyl.

In one embodiment, with respect to the hybrid polymers of formula II, or III, each of $R^2$ is independently guanidinomethyl, 2-guanidinoethyl, 3-guanidinopropyl, 4-guanidinobutyl, 5-guanidinopentyl, or 6-guanidinohexyl.

In one embodiment, with respect to the hybrid polymers of formula II, or III, each of $R^2$ is independently 4-guanidinobutyl.

In one embodiment, with respect to the hybrid polymers of formula II, or III, each of $R^2$ is independently imidazolylmethyl, 2-imidazolylethyl, 3-imidazolylpropyl, 4-imidazolylbutyl, 5-imidazolylpentyl, or 6-imidazolylhexyl.

In one embodiment, with respect to the hybrid polymers of formula II, or III, each of $R^2$ is independently methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In one embodiment, with respect to the hybrid polymers of formula II, or III, each of $R^2$ is independently selected from a group consisting of any of the $R^2$ groups described above.

In one particular embodiment, with respect to the hybrid polymers of formula II, or III, each of $R^2$ is independently Me, i-Pr, i-Bu, sec-Bu, phenethyl, 4-hydroxyphenethyl, benzimidazol-3-ylmethyl, thiomethyl, methylthioethyl, hydroxymethyl, aminopropyl, guanadinopropyl, and imdazo-4-yl methyl.

In one embodiment, with respect to the hybrid polymers of formula III, each of $R^3$ is independently H, Me, Et, n-Pr, i-Pr, n-Bu, sec-Bu, or i-Bu.

In one embodiment, with respect to the hybrid polymers of formula III, each of $R^3$ is independently phenyl or benzyl, unsubstituted or substituted with one or more groups selected from alkyl, halo, hydroxy, amino, nitro, and alkoxy.

In one embodiment, with respect to the hybrid polymers of formula III, each of $R^3$ is independently phenethyl, unsubstituted or substituted with one or more groups selected from alkyl, halo, hydroxy, amino, nitro, and alkoxy.

In one embodiment, with respect to the hybrid polymers of formula III, each of $R^3$ is independently 2-naphthyl, unsubstituted or substituted with one or more groups selected from alkyl, halo, hydroxy, amino, nitro, and alkoxy.

In one embodiment, with respect to the hybrid polymers of formula III, each of $R^3$ is independently 2,2-diphenylethyl, unsubstituted or substituted with one or more groups selected from alkyl, halo, hydroxy, amino, nitro, and alkoxy.

In one embodiment, with respect to the hybrid polymers of formula III, each of $R^3$ is independently furanyl or thienyl, unsubstituted or substituted with one or more groups selected from alkyl, halo, hydroxy, amino, nitro, and alkoxy.

In one embodiment, with respect to the hybrid polymers of formula III, each of $R^3$ is independently aminomethyl, 2-aminoethyl, 3-aminopropyl, 4-aminobutyl, 5-aminopentyl, or 6-aminohexyl.

In one embodiment, with respect to the hybrid polymers of formula III, each of $R^3$ is independently 3-aminopropyl.

In one embodiment, with respect to the hybrid polymers of formula III, each of $R^3$ is independently guanidinoalkyl.

In one embodiment, with respect to the hybrid polymers of formula III, each of $R^3$ is independently guanidinomethyl, 2-guanidinoethyl, 3-guanidinopropyl, 4-guanidinobutyl, 5-guanidinopentyl, or 6-guanidinohexyl.

In one embodiment, with respect to the hybrid polymers of formula III, each of $R^3$ is independently 4-guanidinobutyl.

In one embodiment, with respect to the hybrid polymers of formula III, each of $R^3$ is independently imidazolylmethyl, 2-imidazolylethyl, 3-imidazolylpropyl, 4-imidazolylbutyl, 5-imidazolylpentyl, or 6-imidazolylhexyl.

In one embodiment, with respect to the hybrid polymers of formula III, each of $R^3$ is independently methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In one embodiment, with respect to the hybrid polymers of formula III, each of $R^3$ is selected from a group consisting of any of the $R^3$ groups described above.

In a particular embodiment, with respect to the hybrid polymers of formula III, each of $R^3$ is independently H, Me, i-Pr, i-Bu, sec-Bu, phenethyl, 4-hydroxyphenethyl, benzimidazol-3-ylmethyl, thiomethyl, methylthioethyl, hydroxymethyl, aminopropyl, guanadinopropyl, or imdazo-4-yl methyl.

In a particular embodiment, with respect to the hybrid polymers of formula III, each of the groups —[N(H)—CH($R^3$)—C(=O)]— is independently amino acid residue, and the residue is selected from glycine, L-alanine, L-valine, L-leucine, L-iso-leucine, L-tyrosine, L-proline, L-serine, L-glutamic acid, L-tryptophan, L-phenylalanine, L-methionine, L-arginine, and L-histidine residue.

In one embodiment, with respect to the hybrid polymers of formula I, II, or III, Y is acyl, unsubstituted or substituted with cycloalkyl, or phenyl.

In one embodiment, with respect to the hybrid polymers of formula I, II, or III, Y is acetyl, lauroyl, tridecanoyl, myristoyl, pentadecanoyl, palmitoyl, caproyl, benzoyl, cetyl, decyl, acetyl, phenyl acetyl, cyclohexyl acetyl, valeroyl, or glucuronyl residue.

In one embodiment, with respect to the hybrid polymers of formula I, II, or III, Y is —COCH$_3$.

In one embodiment, with respect to the hybrid polymers of formula I, II, or III, X is —NH$_2$.

In one embodiment, with respect to the hybrid polymers of formula I, II, or III, X is —OH.

In one embodiment, with respect to the hybrid polymers of formula I, II, or III, X is —O-alkyl.

In one embodiment, with respect to the hybrid polymers of formula I, II, or III, X is —OMe, or —OEt.

In one embodiment, with respect to the hybrid polymers of the present invention, the oligomers is Compound 9, Compound 10, Compound II, Compound 12, Compound 13, Compound 14, Compound 15, Compound 16, Compound 17, Compound 18, Compound 19, Compound 20, Compound 21, Compound 22, Compound 23, or Compound 24:

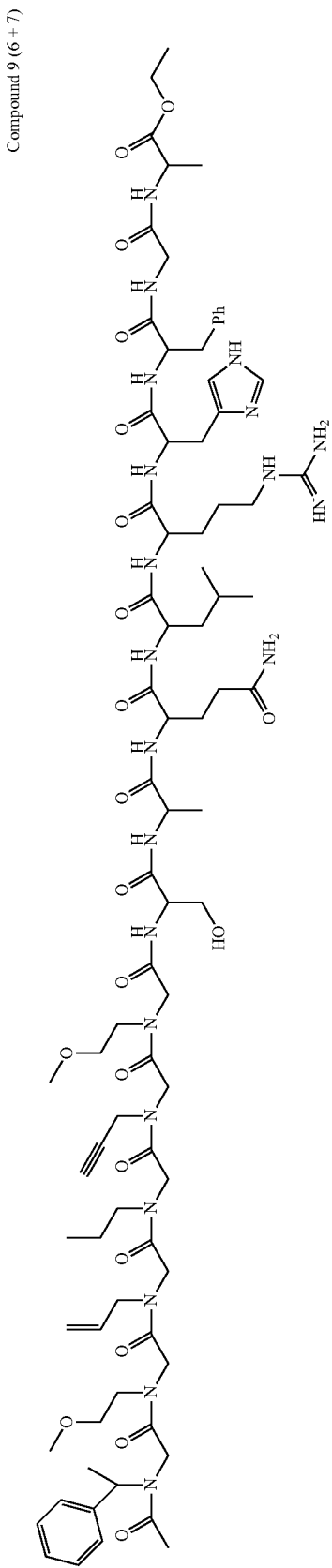
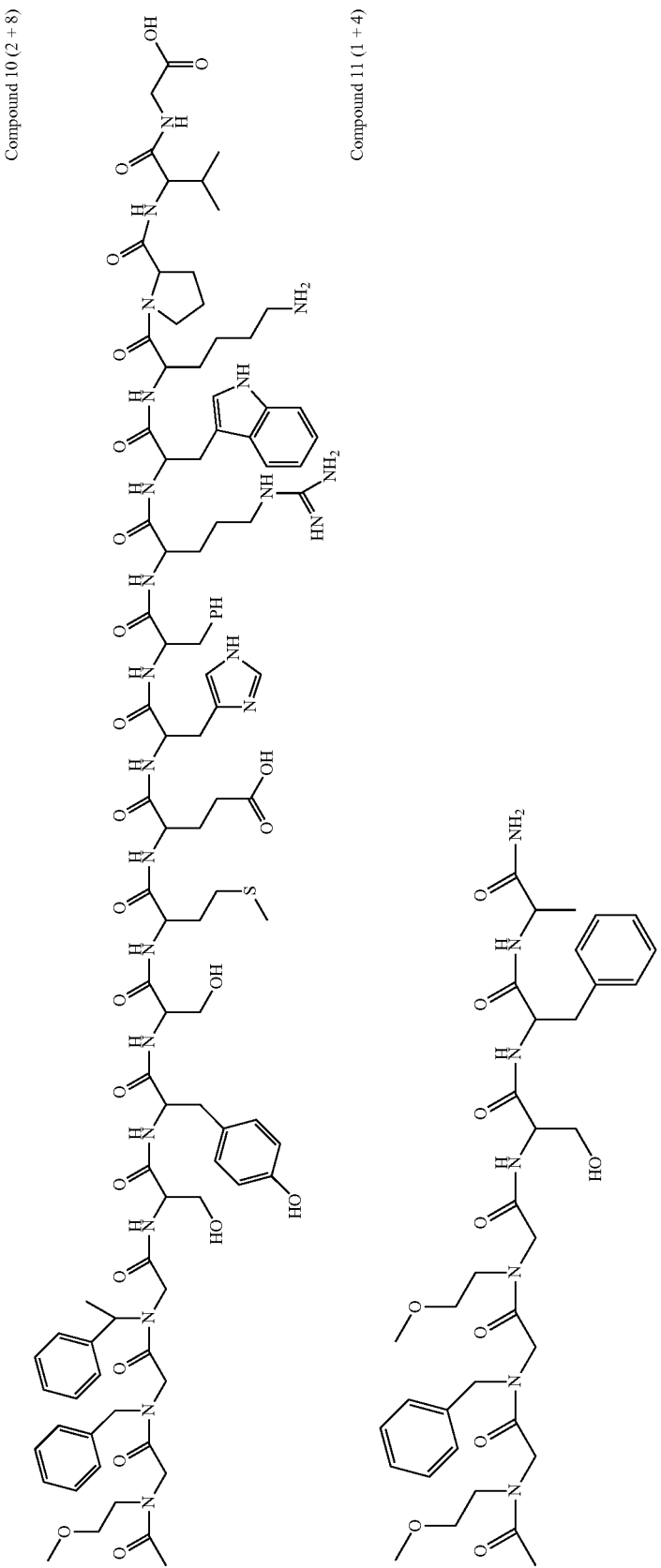

-continued
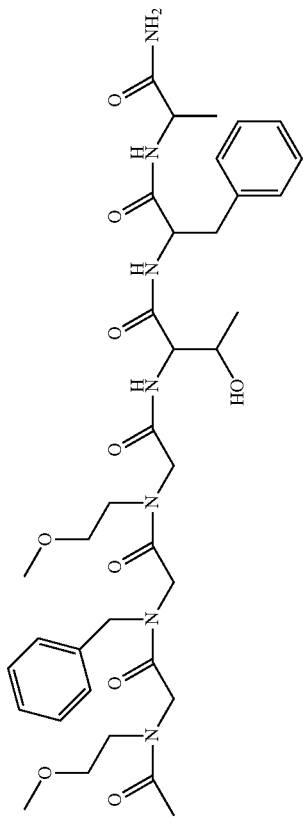
Compound 12 (1 + 5)
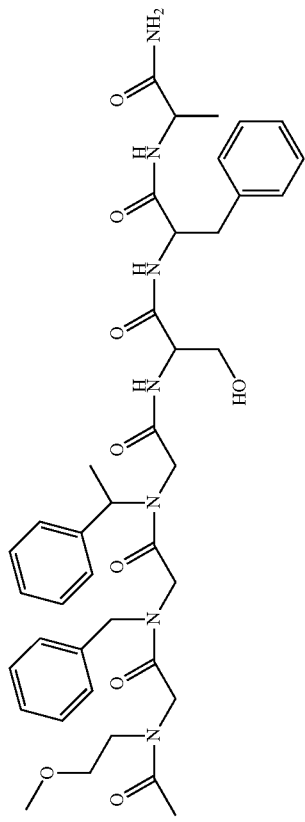
Compound 13 (2 + 4)
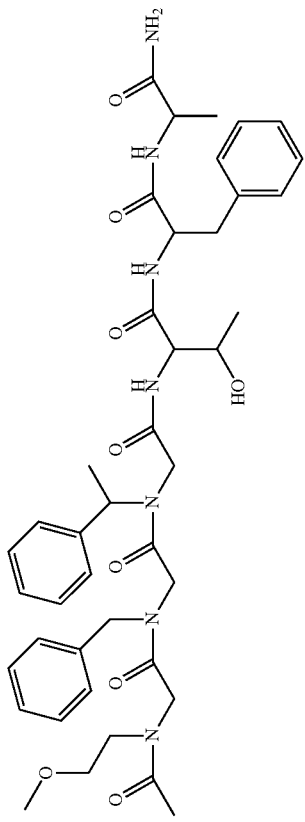
Compound 14 (2 + 5)

-continued
Compound 15 (3 + 4)
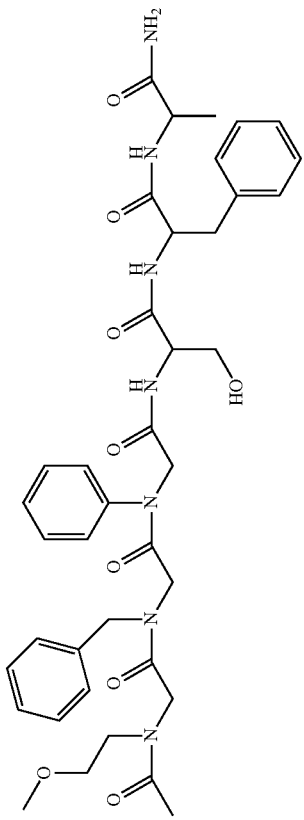
Compound 16 (3 + 5)
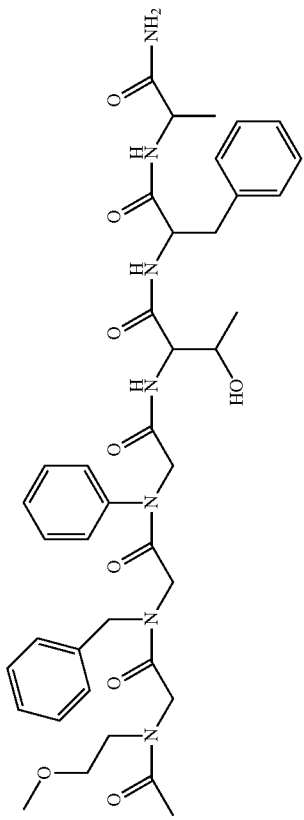
Compound 17 (6 + 4)
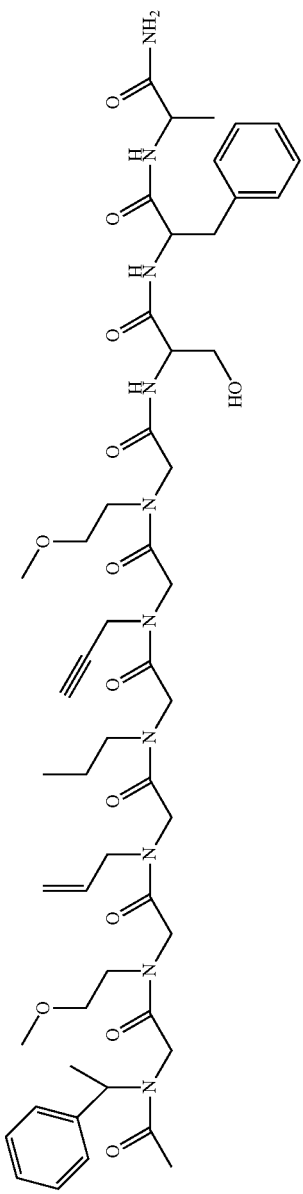

-continued
Compound 17 (6 + 4)
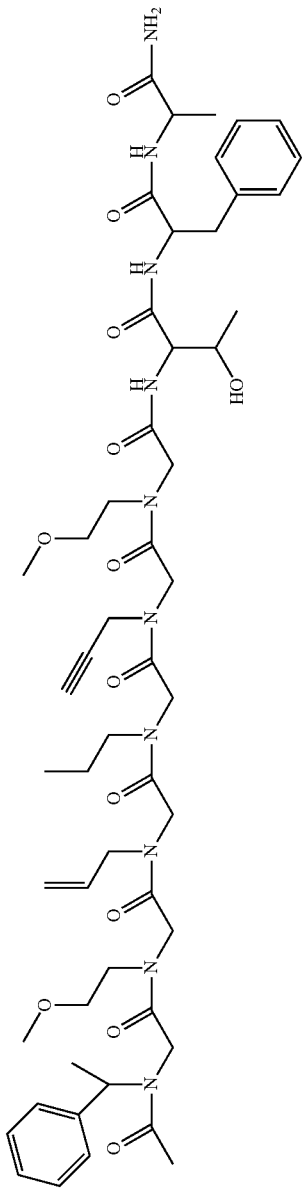
Compound 19 (1 + 7)
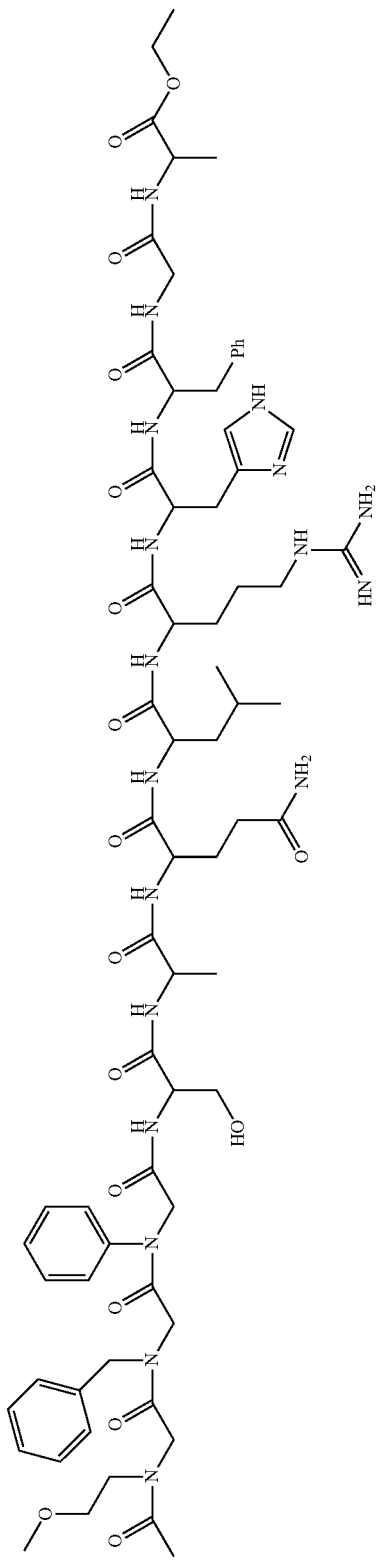
Compound 20 (2 + 7)
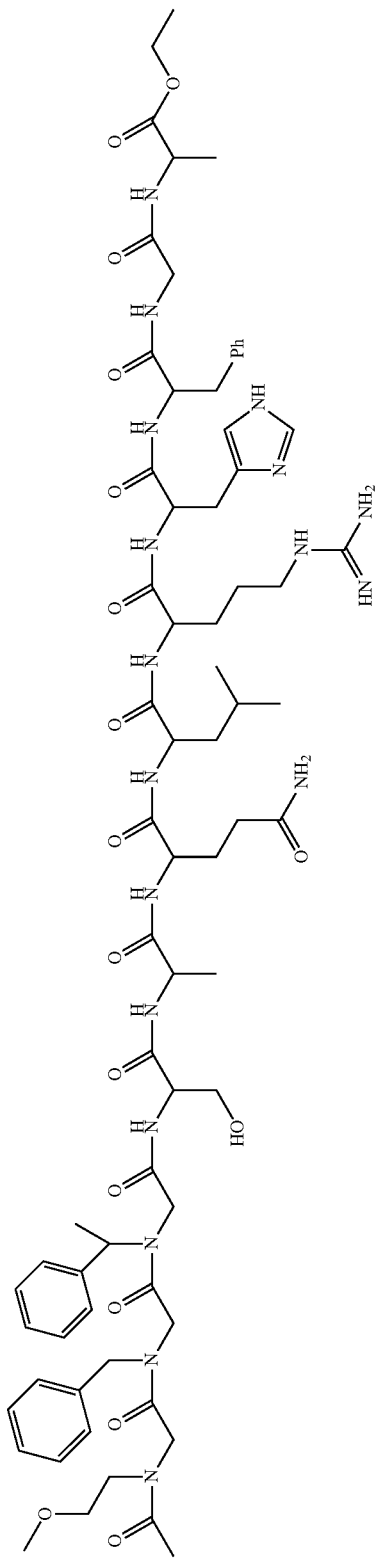

-continued
Compound 21 (3 + 7)
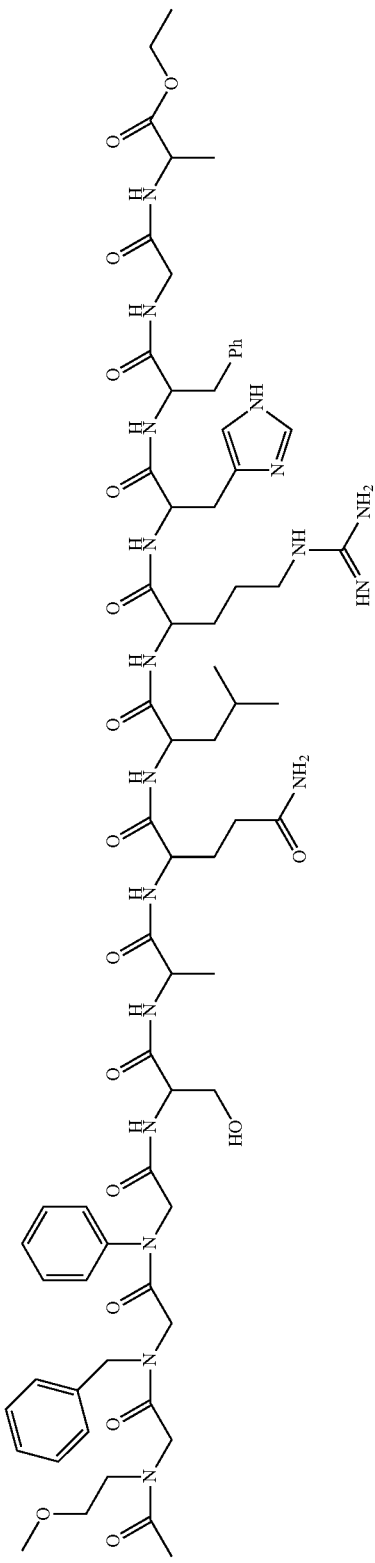
Compound 22 (1 + 8)
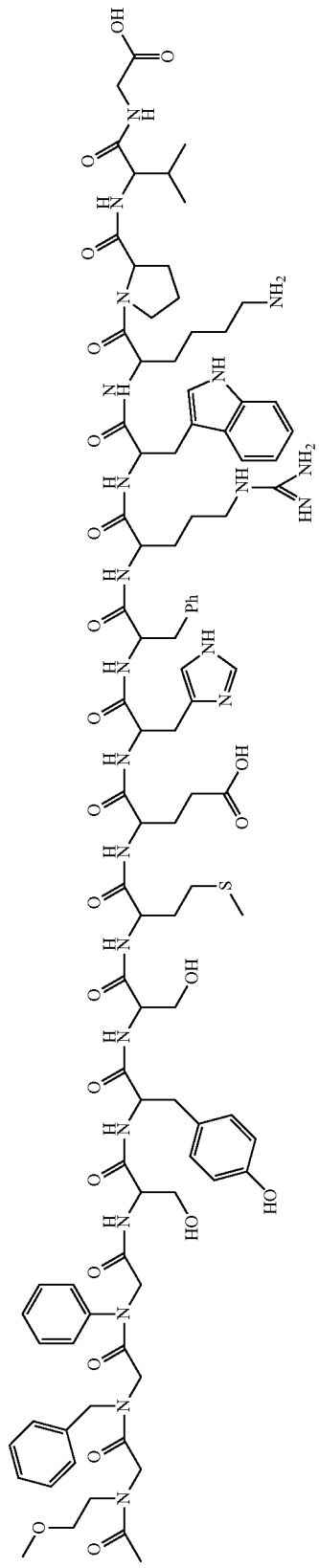
Compound 23 (3 + 8) or
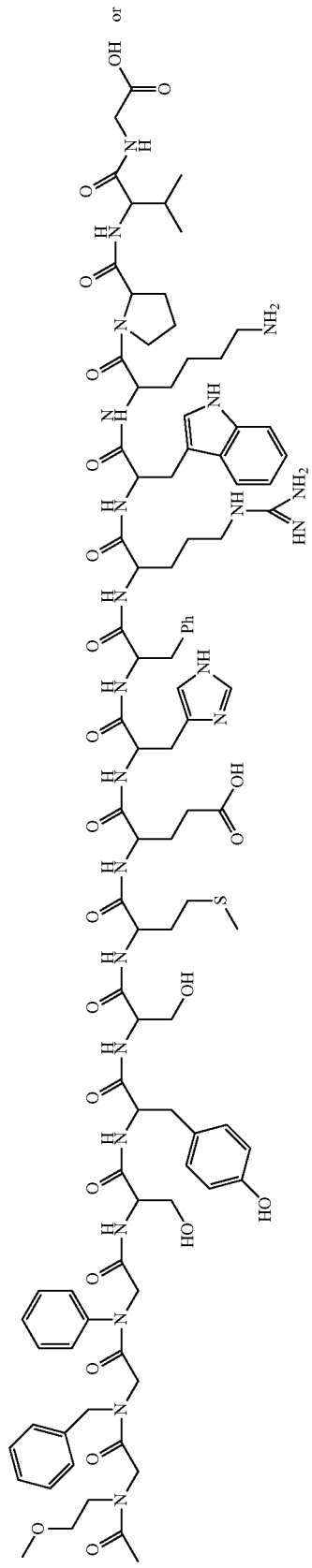

-continued
Compound 24 (6 + 8)
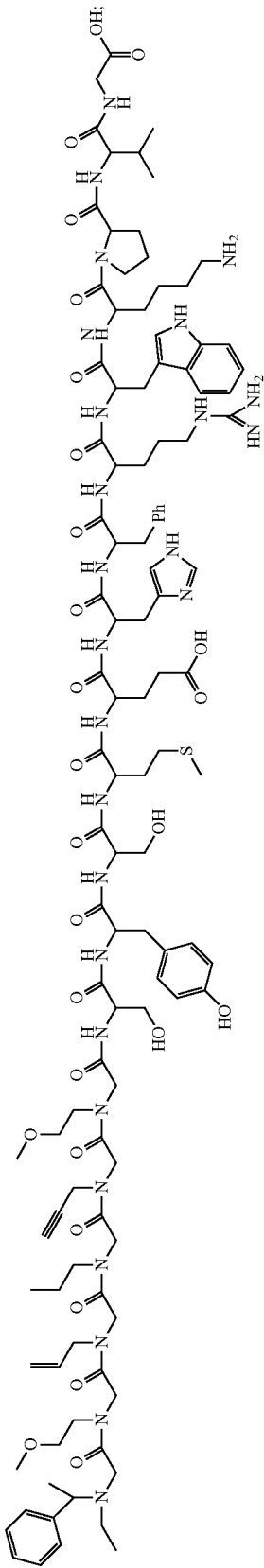

or a pharmaceutically acceptable salt, stereoisomer, isotopic variant or tautomer thereof.

In yet another aspect, the present invention provides, processes for preparing hybrid polymer according to formula I:

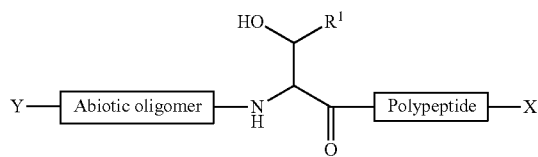

or a pharmaceutically acceptable salt, stereoisomer, isotopic variant or tautomer thereof; comprising the steps of A1) reacting the compound of formula SI-1 with salicylaldehyde of formula SI-2

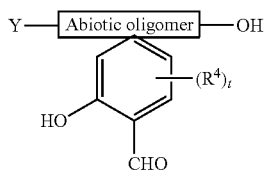

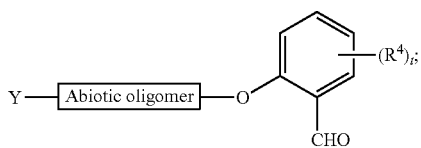

to form a compound of formula SI-3:

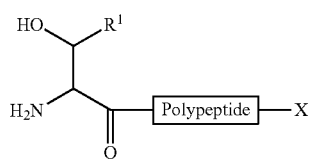

A2) reacting the compound of formula SI-3 with a polypeptide of formula SI-4

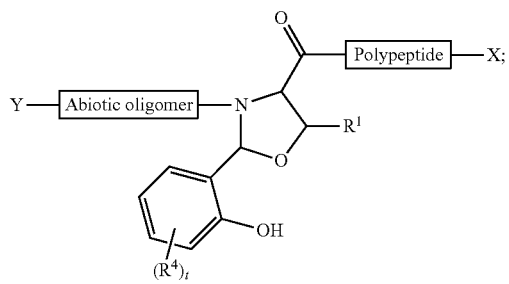

to form the oxazolidine compound of formula SI-5:

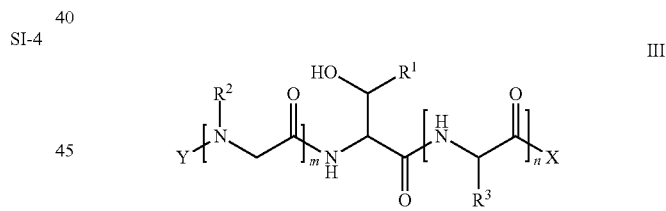

and

A3) reacting the oxazolidine compound of formula SI-5 with an acid to form the hybrid polymer of formula I;

wherein

Polypeptide is as described herein;

Abiotic oligomer is as described herein;

X is hydroxyl, alkoxy, amino or substituted amino;

Y is H or acetyl;

$R^1$ is H or methyl;

each $R^4$ is independently H or substituted or unsubstituted alkyl;

and the subscript t is 1, 2, 3, or 4.

In one embodiment, the abiotic oligomer comprises abiotic oligomer segment comprises N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas, and combinations thereof.

In one embodiment, the abiotic oligomer comprises beta-amino acid oligomers.

In one embodiment, the abiotic oligomer comprises gamma-amino acid oligomers.

In one embodiment, the abiotic oligomer comprises peptoids such as N-substituted glycine oligomers.

In one embodiment, the abiotic oligomer comprises peptoids such as N-substituted beta-alanine oligomers.

In one embodiment, the abiotic oligomer comprises oligoureas.

In one embodiment, the abiotic oligomer comprises oligophenyleneethynylenes.

In one embodiment, the abiotic oligomer comprises peptide nucleic acids (PNAs).

In yet another aspect, the present invention provides, processes for preparing hybrid polymer according to formula III:

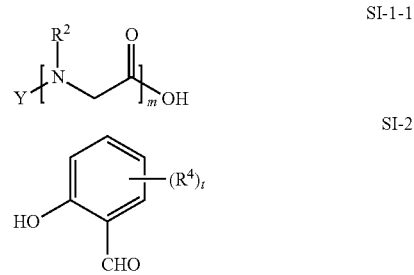

or a pharmaceutically acceptable salt, stereoisomer, isotopic variant or tautomer thereof; comprising the steps of B1) reacting the compound of formula SI-1-1 with salicylaldehyde of formula SI-2 to form a compound of formula SI-3-1:

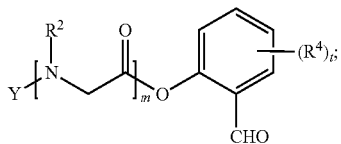

SI-3-1

B2) reacting the compound of formula SI-3-1 with a peptide of formula SI-4-1

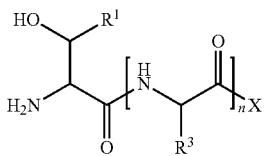

SI-4-1 to form the oxazolidine compound of formula SI-5-1:

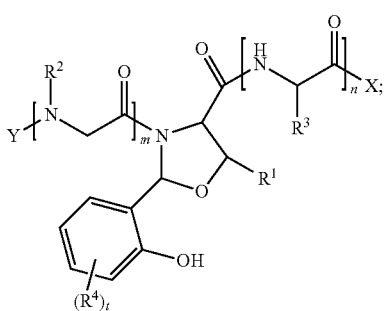

SI-5-1 and

B3) reacting the oxazolidine compound of formula SI-5-1 with an acid to form the hybrid polymer of formula III;

wherein

X is hydroxyl, alkoxy, amino or substituted amino;

Y is H or acetyl;

$R^1$ is H or methyl;

each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;

each $R^3$ is independently selected from a group consisting of H, substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;

each $R^4$ is independently H or substituted or unsubstituted alkyl;

the subscript m is an integer from 2-200; the subscript n is an integer from 2-1000; and the subscript t is 1, 2, 3, or 4.

In one embodiment, with respect to the process, the step A1 or B1 occurs in the presence of a solvent.

In one embodiment, with respect to the process, the step A1 or B1 occurs in the presence of methylene chloride, ethylene chloride, or tetrachloroethane.

In one embodiment, with respect to the process, the step A1 or B1 occurs in the presence of methylene chloride.

In one embodiment, with respect to the process, the step A1 or B1 occurs in the presence of diisopropylcarbodiimide.

In one embodiment, with respect to the process, the step A1 or B1 occurs in the presence of diisopropylcarbodiimide (DIC); and the DIC is about 1.2 equivalent of the SI-1 or SI-1-1.

In one embodiment, with respect to the process, the step A1 or B1 occurs in the presence of a catalyst. In one embodiment, the catalyst is a base. In another embodiment, the catalyst is a tertiary amine. In a particular embodiment, the catalyst is dimethylaminopyridine (DMAP).

In one embodiment, with respect to the process, the step A1 or B1 occurs in the presence of a catalytic amount of dimethylaminopyridine (DMAP).

In one embodiment, with respect to the process, the step A1 or B1 occurs at around 20-30° C.

In one embodiment, with respect to the process, the step A1 or B1 occurs for 4-24 hrs.

In one embodiment, with respect to the process, the step A2 or B2 occurs in the presence of a solvent.

In one embodiment, with respect to the process, the step A2 or B2 occurs in the presence of a solvent; and the solvent is pyridine.

In one embodiment, with respect to the process, the step A2 or B2 occurs in the presence of an acid.

In one embodiment, with respect to the process, the step A2 or B2 occurs in the presence of acetic acid.

In one embodiment, with respect to the process, step A2 or B2 occurs in the presence of 1:1 mole/mole pyridine and acetic acid.

In one embodiment, with respect to the process, the step A2 or B2 occurs at around 20-30° C.

In one embodiment, with respect to the process, the step A3 or B3 occurs in the presence of solvent.

In one embodiment, with respect to the process, the step A3 or B3 occurs in the presence of an acid.

In one embodiment, with respect to the process, the step A3 or B3 occurs in the presence of trifluoroacetic acid (TFA).

In one embodiment, with respect to the process, the step A3 or B3 occurs in the presence of i-$Pr_3SiH$.

In one embodiment, with respect to the process, the step A3 or B3 occurs in the presence of water.

In one embodiment, with respect to the process, the step A3 or B3 occurs in the presence of TFA, water and i-$Pr_3SiH$ (94/5/1, v/v/v).

In one embodiment, with respect to the process, the step A3 or B3 occurs for 0.1 to 2 hrs.

In yet another aspect, the present invention provides, oxazolidine compounds according to formula SI-5:

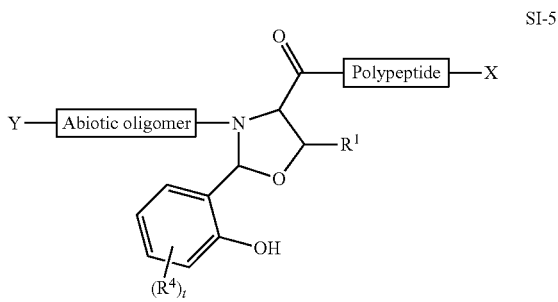

SI-5 or a stereoisomer, or a tautomer thereof;
wherein
Polypeptide is as described herein;
Abiotic oligomer is as described herein;
X is hydroxyl, alkoxy, amino or substituted amino;
Y is H or acetyl;
$R^1$ is H or methyl;
each $R^4$ is independently H or substituted or unsubstituted alkyl.

In one embodiment, the abiotic oligomer comprises abiotic oligomer segment comprises N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas, and combinations thereof.

In yet another aspect, the present invention provides, oxazolidine compounds according to formula SI-5-1:

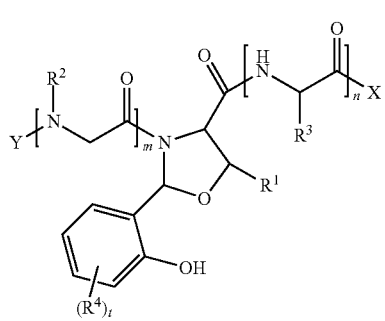

SI-5-1 or a stereoisomer, or a tautomer thereof;
wherein
X is hydroxyl, alkoxy, amino or substituted amino;
Y is H or acetyl;
$R^1$ is H or methyl;
each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
each $R^3$ is independently selected from a group consisting of H, substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
each $R^4$ is independently H or substituted or unsubstituted alkyl;
and
the subscript m is an integer from 2-200; the subscript n is an integer from 2-1000; and
the subscript t is 1, 2, 3, or 4.

In one embodiment, with respect to the process or the oxazolidine compounds, $R^1$ is H.
In one embodiment, with respect to the process or the oxazolidine compounds, $R^1$ is Me.
In one embodiment, with respect to the process or the compounds, each of $R^2$ is independently Me, Et, n-Pr, i-Pr, n-Bu, sec-Bu, or i-Bu.
In another embodiment, with respect to the process or the compounds, each of $R^2$ is independently phenyl or benzyl, unsubstituted or substituted with one or more groups selected from alkyl, halo, hydroxy, amino, nitro, and alkoxy.

In another embodiment, with respect to the process or the compounds, each of $R^2$ is independently phenethyl, unsubstituted or substituted with one or more groups selected from alkyl, halo, hydroxy, amino, nitro, and alkoxy.

In another embodiment, with respect to the process or the compounds, each of $R^2$ is independently 2-naphthyl, unsubstituted or substituted with one or more groups selected from alkyl, halo, hydroxy, amino, nitro, and alkoxy.

In another embodiment, with respect to the process or the compounds, each of $R^2$ is independently 2,2-diphenylethyl, unsubstituted or substituted with one or more groups selected from alkyl, halo, hydroxy, amino, nitro, and alkoxy.

In another embodiment, with respect to the process or the compounds, each of $R^2$ is independently furanyl or thienyl, unsubstituted or substituted with one or more groups selected from alkyl, halo, hydroxy, amino, nitro, and alkoxy.

In another embodiment, with respect to the process or the compounds, each of $R^2$ is independently aminomethyl, 2-aminoethyl, 3-aminopropyl, 4-aminobutyl, 5-aminopentyl, or 6-aminohexyl.

In another embodiment, with respect to the process or the compounds, each of $R^2$ is independently 3-aminopropyl.

In another embodiment, with respect to the process or the compounds, each of $R^2$ is independently guanidinoalkyl.

In another embodiment, with respect to the process or the compounds, each of $R^2$ is independently guanidinomethyl, 2-guanidinoethyl, 3-guanidinopropyl, 4-guanidinobutyl, 5-guanidinopentyl, or 6-guanidinohexyl.

In another embodiment, with respect to the process or the compounds, each of $R^2$ is independently 4-guanidinobutyl.

In another embodiment, with respect to the process or the compounds, each of $R^2$ is independently imidazolylmethyl, 2-imidazolylethyl, 3-imidazolylpropyl, 4-imidazolylbutyl, 5-imidazolylpentyl, or 6-imidazolylhexyl.

In another embodiment, with respect to the process or the compounds, each of $R^2$ is independently methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In one embodiment, with respect to the process or the compounds, each of $R^2$ is independently Me, i-Pr, i-Bu, sec-Bu, phenethyl, 4-hydroxyphenethyl, benzimidazol-3-yl-methyl, thiomethyl, methylthioethyl, hydroxymethyl, aminopropyl, guanadinopropyl, or imdazo-4-yl methyl.

In one embodiment, with respect to the process or the compounds, each of $R^3$ is independently H, Me, Et, n-Pr, i-Pr, n-Bu, sec-Bu, or i-Bu.

In another embodiment, with respect to the process or the compounds, each of $R^3$ is independently phenyl or benzyl, unsubstituted or substituted with one or more groups selected from alkyl, halo, hydroxy, amino, nitro, and alkoxy.

In another embodiment, with respect to the process or the compounds, each of $R^3$ is independently phenethyl, unsubstituted or substituted with one or more groups selected from alkyl, halo, hydroxy, amino, nitro, and alkoxy.

In another embodiment, with respect to the process or the compounds, each of $R^3$ is independently 2-naphthyl, unsubstituted or substituted with one or more groups selected from alkyl, halo, hydroxy, amino, nitro, and alkoxy.

In another embodiment, with respect to the process or the compounds, each of $R^3$ is independently 2,2-diphenylethyl, unsubstituted or substituted with one or more groups selected from alkyl, halo, hydroxy, amino, nitro, and alkoxy.

In another embodiment, with respect to the process or the compounds, each of $R^3$ is independently furanyl or thienyl, unsubstituted or substituted with one or more groups selected from alkyl, halo, hydroxy, amino, nitro, and alkoxy.

In another embodiment, with respect to the process or the compounds, each of $R^3$ is independently aminomethyl, 2-aminoethyl, 3-aminopropyl, 4-aminobutyl, 5-aminopentyl, or 6-aminohexyl.

In another embodiment, with respect to the process or the compounds, each of $R^3$ is independently 3-aminopropyl.

In another embodiment, with respect to the process or the compounds, each of $R^3$ is independently guanidinoalkyl.

In another embodiment, with respect to the process or the compounds, each of $R^3$ is independently guanidinomethyl, 2-guanidinoethyl, 3-guanidinopropyl, 4-guanidinobutyl, 5-guanidinopentyl, or 6-guanidinohexyl.

In another embodiment, with respect to the process or the compounds, each of $R^3$ is independently 4-guanidinobutyl.

In another embodiment, with respect to the process or the compounds, each of $R^3$ is independently imidazolylmethyl, 2-imidazolylethyl, 3-imidazolylpropyl, 4-imidazolylbutyl, 5-imidazolylpentyl, or 6-imidazolylhexyl.

In another embodiment, with respect to the process or the compounds, each of $R^3$ is independently methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In one embodiment, with respect to the process or the compounds, each of $R^3$ is independently Me, i-Pr, i-Bu, sec-Bu, phenethyl, 4-hydroxyphenethyl, benzimidazol-3-yl-methyl, thiomethyl, methylthioethyl, hydroxymethyl, aminopropyl, guanadinopropyl, or imdazo-4-yl methyl.

In another embodiment, with respect to the process or the compounds, the subscript t is 4; and each of $R^4$ is H.

In another embodiment, with respect to the process or the compounds, Y is acyl, unsubstituted or substituted with cycloalkyl, or phenyl.

In another embodiment, with respect to the process or the compounds, Y is acetyl, lauroyl, tridecanoyl, myristoyl, pentadecanoyl, palmitoyl, caproyl, benzoyl, cetyl, decyl, acetyl, phenyl acetyl, cyclohexyl acetyl, valeroyl, or glucuronyl residue.

In another embodiment, with respect to the process or the compounds, Y is —COCH$_3$.

In another embodiment, with respect to the process or the compounds, X is —NH$_2$.

In another embodiment, with respect to the process or the compounds, X is —OH.

In another embodiment, with respect to the process or the compounds, X is —O-alkyl.

In another embodiment, with respect to the process or the compounds, X is —OMe, or —OEt.

In another embodiment, with respect to formula II, III, SI-1-1, SI-3-1, SI-5, or SI-5-1, m is an integer between 2-200, 2-100, 2-50, 2-30, 2-20, 2-10, or 2-5.

In another embodiment, with respect to formula III, SI-4-1, or SI-5-1, n is an integer between 2-1000, 2-500, 2-400, 2-200, 2-100, 2-50, 2-30, 2-20, 2-10, or 2-5.

In certain embodiments, each of $R^2$ is independently unsubstituted alkyl.

In certain embodiments, each of $R^2$ is independently unsubstituted phenyl.

In certain embodiments, each of $R^2$ is independently alkyl substituted with one or more groups independently selected from among hydroxyl, thiol (—SH), alkylthio (S-alkyl), substituted or unsubstituted amino, substituted or unsubstituted carboxy, substituted or unsubstituted amido, guanidino, substituted or unsubstituted aryl, substituted or unsubstituted heteroaryl, substituted or unsubstituted cycloalkyl, and substituted or unsubstituted heterocycloalkyl.

In certain embodiments, each of $R^2$ is independently alkyl substituted with one or more groups independently selected from among hydroxyl, thiol (—SH), alkylthio (S-alkyl), amino, carboxy, amido, guanidino, aryl, heteroaryl, cycloalkyl, and heterocycloalkyl.

In certain embodiments, each of $R^2$ is independently alkyl substituted with one or more groups independently selected from among —OH, thiol (—SH), methylthio (S-Me), —NH$_2$, —CO$_2$H, —CONH$_2$, —NH—C(=NH)—NH$_2$, phenyl, hydroxyphenyl, indolyl, imidazolyl, and cyclohexyl.

In certain embodiments, each of $R^3$ is independently unsubstituted alkyl.

In certain embodiments, each of $R^3$ is independently unsubstituted phenyl.

In certain embodiments, each of $R^3$ is independently alkyl substituted with one or more groups independently selected from among hydroxyl, thiol (—SH), alkylthio (S-alkyl), substituted or unsubstituted amino, substituted or unsubstituted carboxy, substituted or unsubstituted amido, guanidino, substituted or unsubstituted aryl, substituted or unsubstituted heteroaryl, substituted or unsubstituted cycloalkyl, and substituted or unsubstituted heterocycloalkyl.

In certain embodiments, each of $R^3$ is independently alkyl substituted with one or more groups independently selected from among hydroxyl, thiol (—SH), alkylthio (S-alkyl), amino, carboxy, amido, guanidino, aryl, heteroaryl, cycloalkyl, and heterocycloalkyl.

In certain embodiments, each of $R^3$ is independently alkyl substituted with one or more groups independently selected from among —OH, thiol (—SH), methylthio (S-Me), —NH$_2$, —CO$_2$H, —CONH$_2$, —NH—C(=NH)—NH$_2$, phenyl, hydroxyphenyl, indolyl, imidazolyl, and cyclohexyl.

In certain aspects, the present invention provides hybrid polymers or compounds comprising a peptoid and a RNase A residue. In one embodiment, the RNase A residue is S-peptide or S-protein; and S-peptide or S-protein are the N-terminal portions (residues 1-20) of RNase A. In one embodiment, the S-protein or S-peptide is obtained by enzymatic cleavage with subtilisin of RNase A.

In certain aspects, the present invention provides hybrid polymers or compounds comprising a peptoid and a PTH (1-34) residue.

In certain aspects and where appropriate, the present invention extends to the preparation of prodrugs and derivatives of the hybrid polymers of the invention. Prodrugs are derivatives which have cleavable groups and become by solvolysis or under physiological conditions the peptoid of the invention, which are pharmaceutically active, in vivo.

In one embodiment, the invention provides a pharmaceutical composition comprising a pharmaceutically acceptable carrier and a pharmaceutically effective amount of the hybrid polymers of formula I.

In one embodiment, the invention provides a pharmaceutical composition of the hybrid polymers of formula I, comprising a pharmaceutically acceptable carrier, and the carrier is a parenteral carrier, oral or topical carrier.

In one embodiment, the invention provides a method for preventing, treating, ameliorating or managing a disease or condition which comprises administering to a patient in need of such prevention, treatment, amelioration or management, a prophylactically or therapeutically effective amount of the pharmaceutical composition of the hybrid polymer of formula I.

In one embodiment, the invention provides a method for preventing, treating, ameliorating or managing a disease or condition, which comprises administering to a patient in need of such prevention, treatment, amelioration or management a prophylactically or therapeutically acceptable amount of a hybrid polymer of formula I, or the pharmaceutical composition thereof.

Pharmaceutical Compositions

When employed as pharmaceuticals, the peptoid compounds of this invention are typically administered in the form of a pharmaceutical composition. Such compositions can be prepared in a manner well known in the pharmaceutical art and comprise at least one active complex. In a further embodiment, the pharmaceutical compositions of the invention may comprise one or more of the peptoid compounds in combination with one or more non-peptoid antibiotic compounds, including known antibiotic compounds. Such combinations yield compositions that exhibit improved effectiveness over like compositions containing the active compounds individually, so that a synergistic effect of the combination is conferred. The exact amounts and proportions of the compounds with respect to each other may vary within the skill of the art.

Generally, the peptide-peptoid compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non limiting example, oral, rectal, vaginal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1

Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of the invention may be admixed as a dry powder with a starch diluent in an approximate 1:1 weight ratio. The mixture is filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

A compound of the invention may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Synthetic Process of the Invention

A general route for the synthesis of structurally complex sequence-specific heteropolymers capable of performing sophisticated functions, such as enzyme-like catalysis, remains a fundamental challenge. While significant attention has been devoted to total chemical synthesis of native proteins, recent advances have also established synthetic routes to generate hybrid polymers, such as proteins bearing abiotic oligomer constituents.[1] These semi-synthetic biomolecules have the potential to exhibit new modes of molecular recognition and enhanced thermodynamic stability. In general, single-atom or small abiotic substitutions have been incorporated into native protein frameworks.[2] The inventors seek to establish new efficient routes to hybrids between diverse abiotic oligomers and polypeptide sequences.

Conventional linear solid-phase peptide synthesis (SPPS) protocols can routinely generate large polypeptides of sizable chain lengths (20-50 monomers). Limitations in the size and structural diversity of the synthetic polypeptide products can restrict their ability to exhibit particular functions, such as enzymatic catalysis. There are limited chemoselective synthetic routes for ligating abiotic and peptide oligomers through native amide linkages.[2] Discovering new methods for conducting chemoselective fragment condensation to incorporate abiotic constituents into protein constructs will facilitate the development of hybrid biohybrid polymers that can establish unprecedented structural motifs, enhanced stability, and novel functions.

General Synthetic Method for Synthesis of Hybrid Polymers of the Invention

The hybrid polymers of the invention can be synthesized following the synthetic scheme given below:

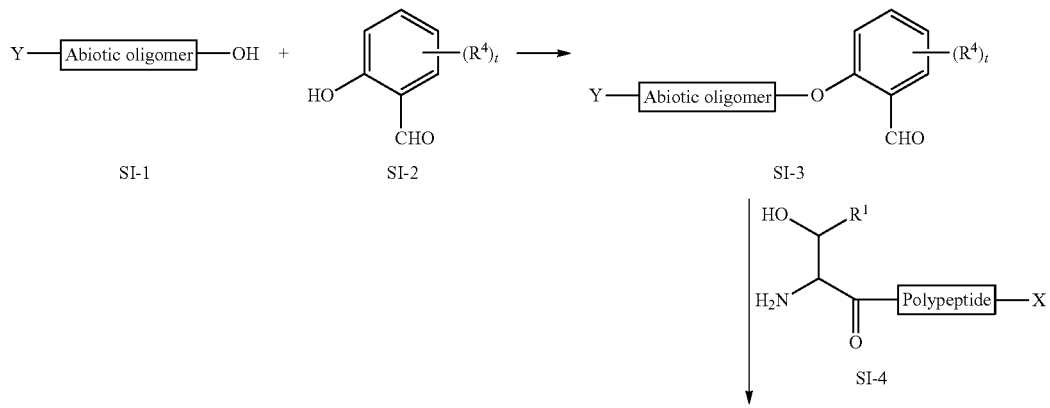

Scheme 1

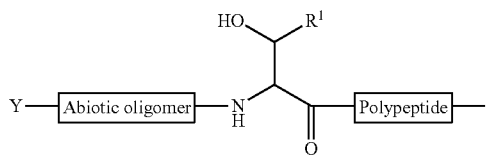 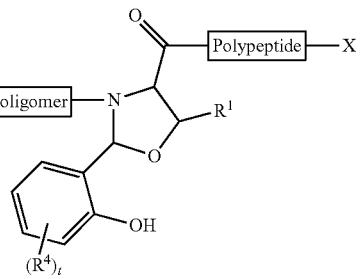

I           SI-5 and wherein Abiotic oligomer, Polypeptide, X, Y, $R^1$, $R^4$, and t are as described herein.

The abiotic oligomer can be beta-amino acid oligomers, gamma-amino acid oligomers, peptoids such as N-substituted glycine oligomers, beta peptides such as N-substituted beta-alanine oligomers, oligoureas, oligophenyleneethynylenes, peptide nucleic acids (PNAs), or combinations thereof. Particularly, the abiotic oligomer can be peptoids.

N-substituted glycine oligomers, or 'peptoids,' are an important class of foldamer compounds composed of tertiary amide linkages.[3]

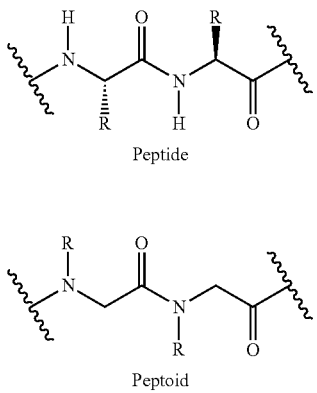

wherein R is a substitution other than hydrogen.

The ability to incorporate extensive chemical diversity into the peptoid side chains facilitates design strategies that allow for a wide range of applications, such as enantioselective catalysis, molecular recognition, and intracellular delivery.[4-6] Importantly, numerous studies have identified peptoid side chains that can control backbone conformational ordering, establishing the potential to fold peptoids into distinct secondary structures that are not populated by polypeptides.[7] More recently, two well-ordered peptoid secondary structure modules were assembled via triazole linkages to generate rudimentary peptoid tertiary structures.[8] Although this strategy permits the design of peptoids that begin to resemble small folded proteins, the ability to craft elaborate functional three-dimensional peptoid-peptide hybrids containing native amide bonds remains a fundamental challenge.

Native Chemical Ligation (NCL) has proven to be exceptionally valuable for the construction of synthetic proteins of extraordinary complexity.[9] NCL typically involves the reaction between a C-terminal peptide thioester and a peptide bearing an N-terminal cysteine residue. Following a selective transthioesterification reaction, a spontaneous S→N acyl transfer affords the native amide bond at the ligation site. Extensive developments in cysteine-based NCL have allowed a multitude of variations in this methodology, including the use of C-terminal phenyl-esters and hydrazide thioester surrogates.[10,11] However, the rare presence of cysteine (1.4% content in proteins) and challenges associated with synthesizing thioesters have limited the utility of cysteine-based NCL.[12] For this reason, new protocols have been introduced that include post-ligation desulfurization to establish native amide linkages at additional amino acid residues (i.e., Arg, Gln, Val, Leu, Lys, and Pro).[13]

In order to circumvent difficulties associated with cysteine-based NCL, alternative strategies to achieve chemoselective fragment condensation, through native amide bond formation, have been introduced. These include α-ketoacid-hydroxylamine (KAHA) ligation and traceless Staudinger ligation.[14,15]

Although initial synthetic strategies for peptoid ligation have been reported, such as disulfide bond formation and Cu-catalyzed azide-alkyne [3+2] cycloaddition (CuAAC) 'click' reactions, none have yielded native amide bond formation.[17,18] Protease-mediated ligation of peptoid oligomers has yielded sequence-defined macromolecular polymers, but of heterogeneous chain lengths.[19] Recently, cysteine-based NCL was attempted to develop peptoid-peptide hybrids of bovine pancreatic ribonuclease A.[20] This study included attempts to synthesize peptoid C-terminal thioesters, which were unsuccessful using either MBHA or hydrazinobenzoyl resin due to incompatibilities with standard peptoid synthesis protocols (e.g., prolonged exposure to primary amines or bromoacetic acid). Instead, the authors successfully utilized the thiazolidine ligation strategy (which does not form native amide bonds) to generate semi-synthetic mimics of bovine pancreatic ribonuclease A and assess their catalytic activity.

Due to the challenges associated with NCL between peptoid and peptide fragments (vida supra), the inventors decided to investigate the applicability of serine/threonine-based NCL to achieve chemoselective condensation using small peptoid and peptide fragments. Employing modified solid-phase peptoid synthesis protocols, the inventors synthesized linear peptoid oligomers containing C-terminal free acids from 2-Chlorotrityl resin (Scheme 2).[19]

Scheme 2
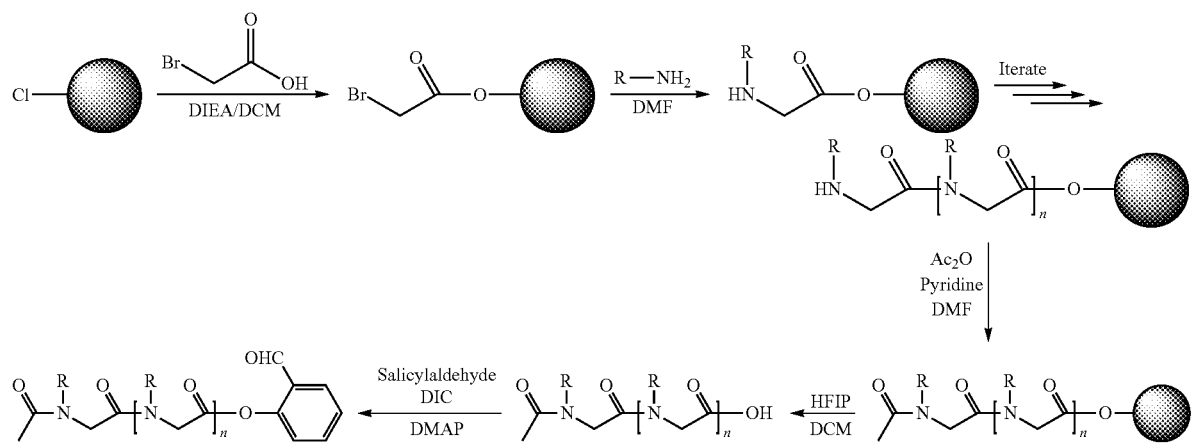
Following C-terminal phenolysis conversion in solution and purification, a small library of peptoid salicylaldehyde esters were evaluated for ligation efficiency utilizing serine/threonine-based NCL with a small set of peptide fragments [25] (see below and FIG. 1).
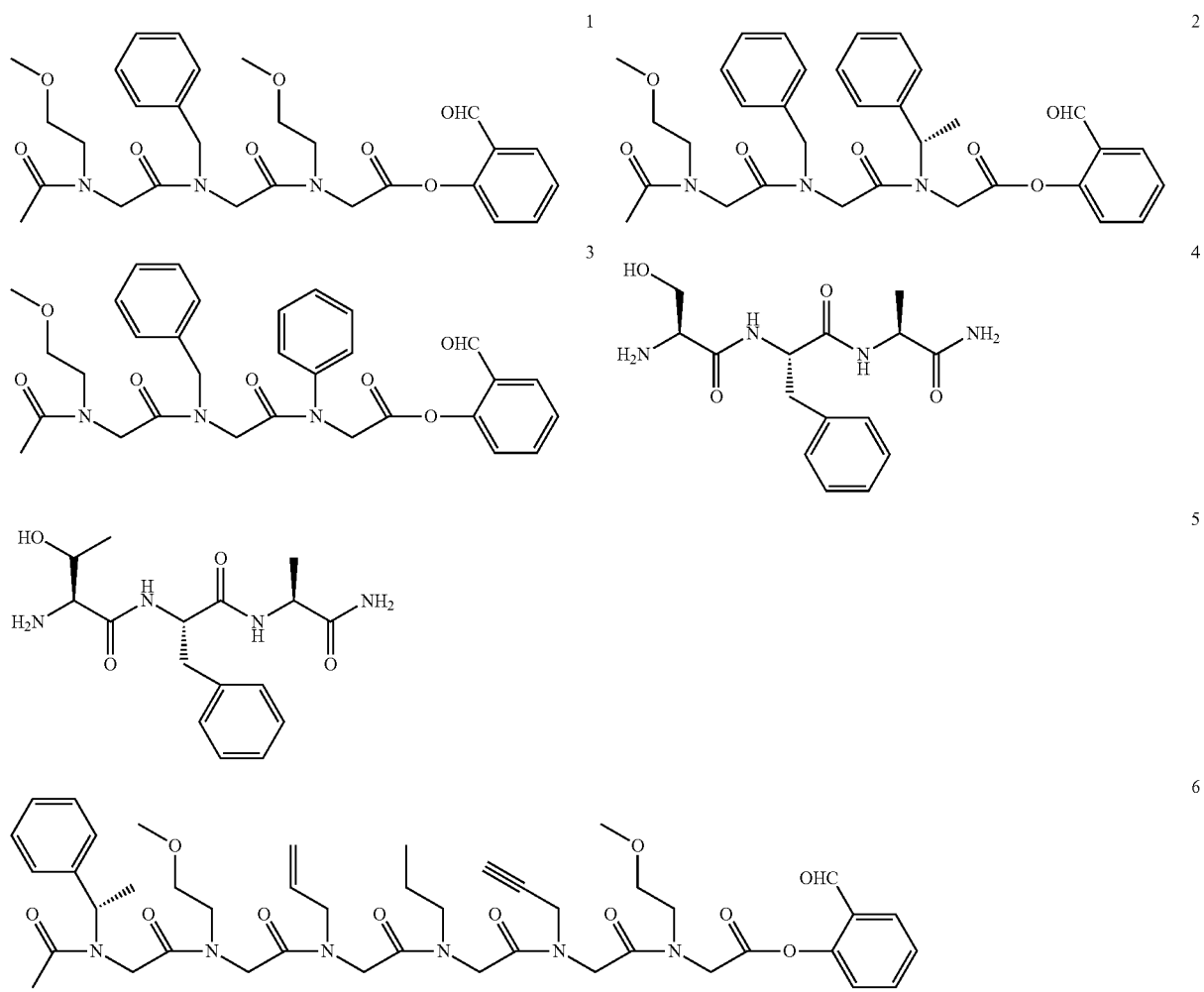

Figure 2:
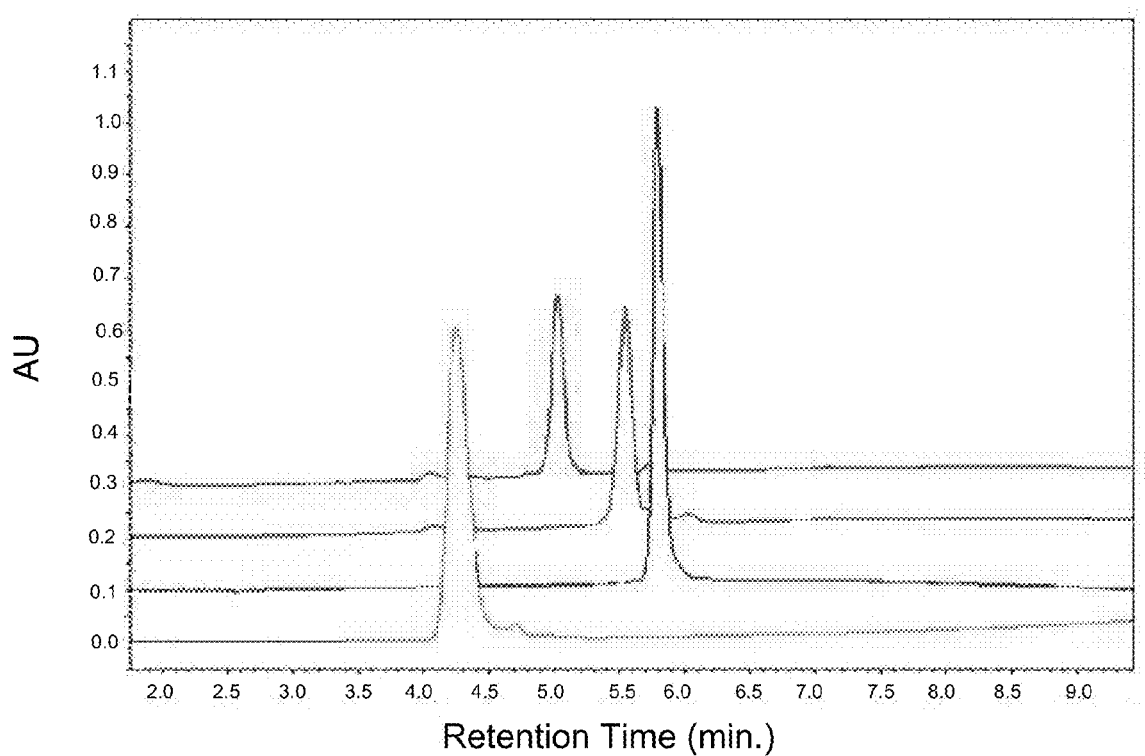
FIG. 2 shows fragment condensation between C-terminal peptoid salicylaldehyde ester 1 and peptide 4. Upper traces of peptoid 1 (purple), intermediate (blue), and product containing native serine (red) are offset in y-direction for clarity. Reaction monitored by HPLC (214 nm) and LCMS. AU indicates absorbance units.
Figure 2:
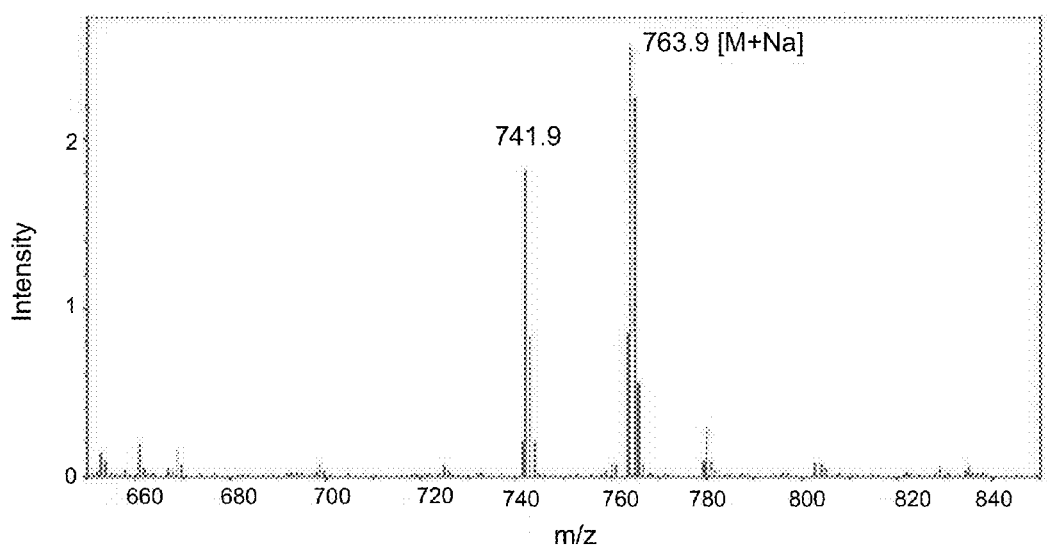
Figure 2:
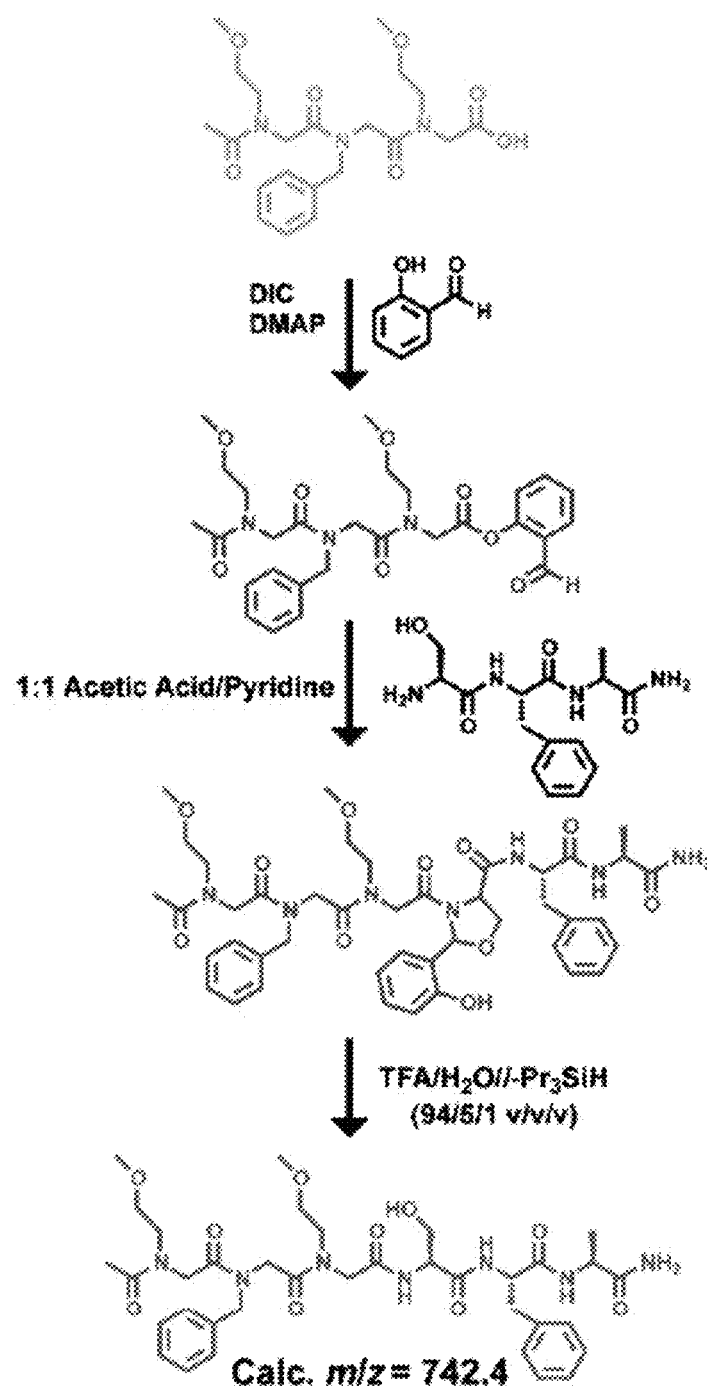

-continued
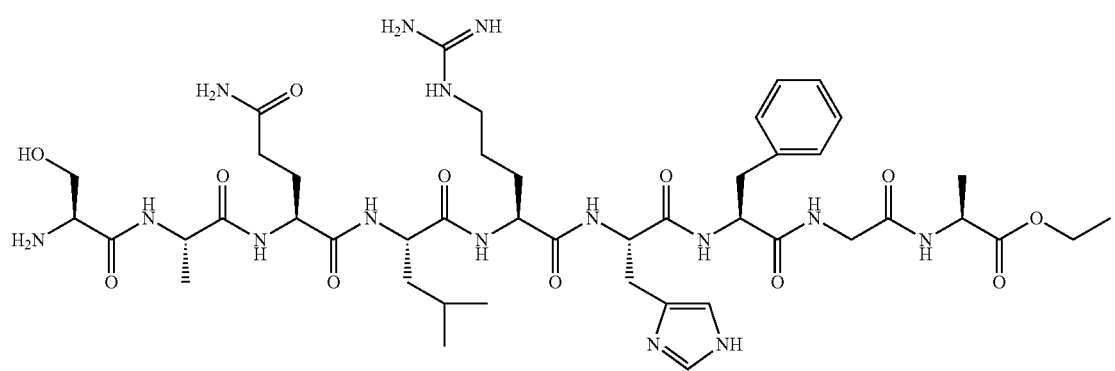
7
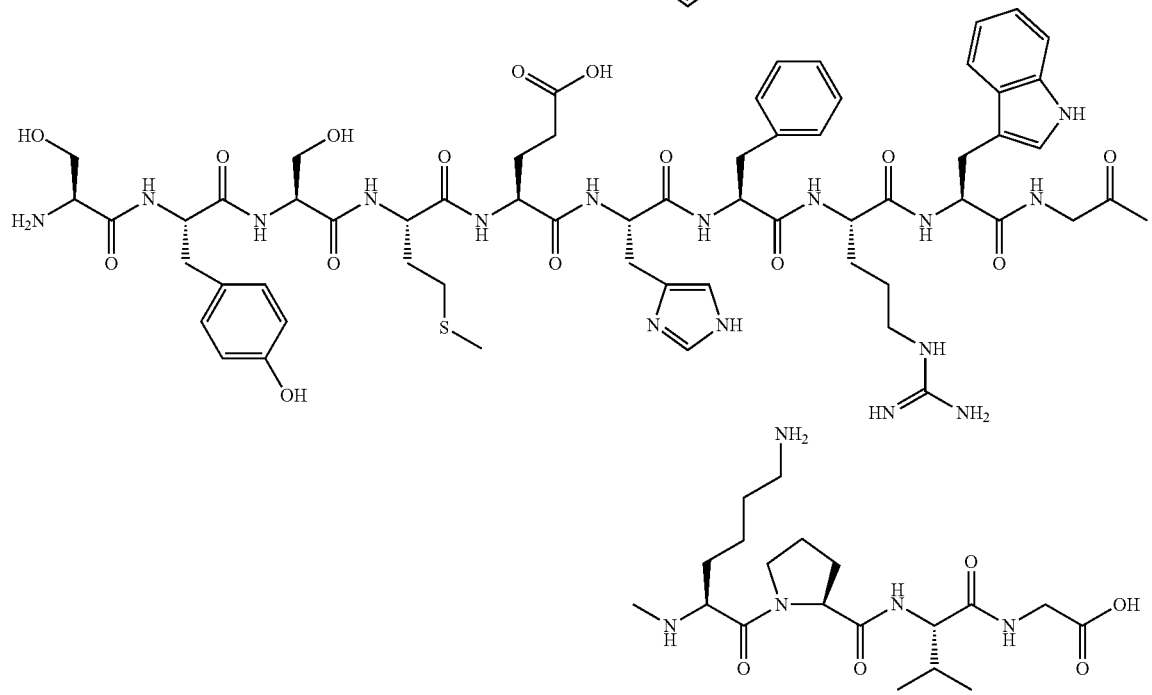
8
Using a simple trimer model system, the inventors coupled peptoid trimer 1 to tripeptide 4, forming the corresponding N,O-benzylidene acetal intermediate. This reaction was monitored by HPLC and LCMS, which established that coupling was complete after 1 hour (see below, FIG. 2 and Table 2).
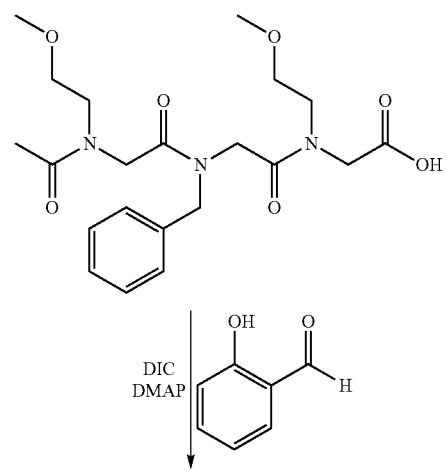

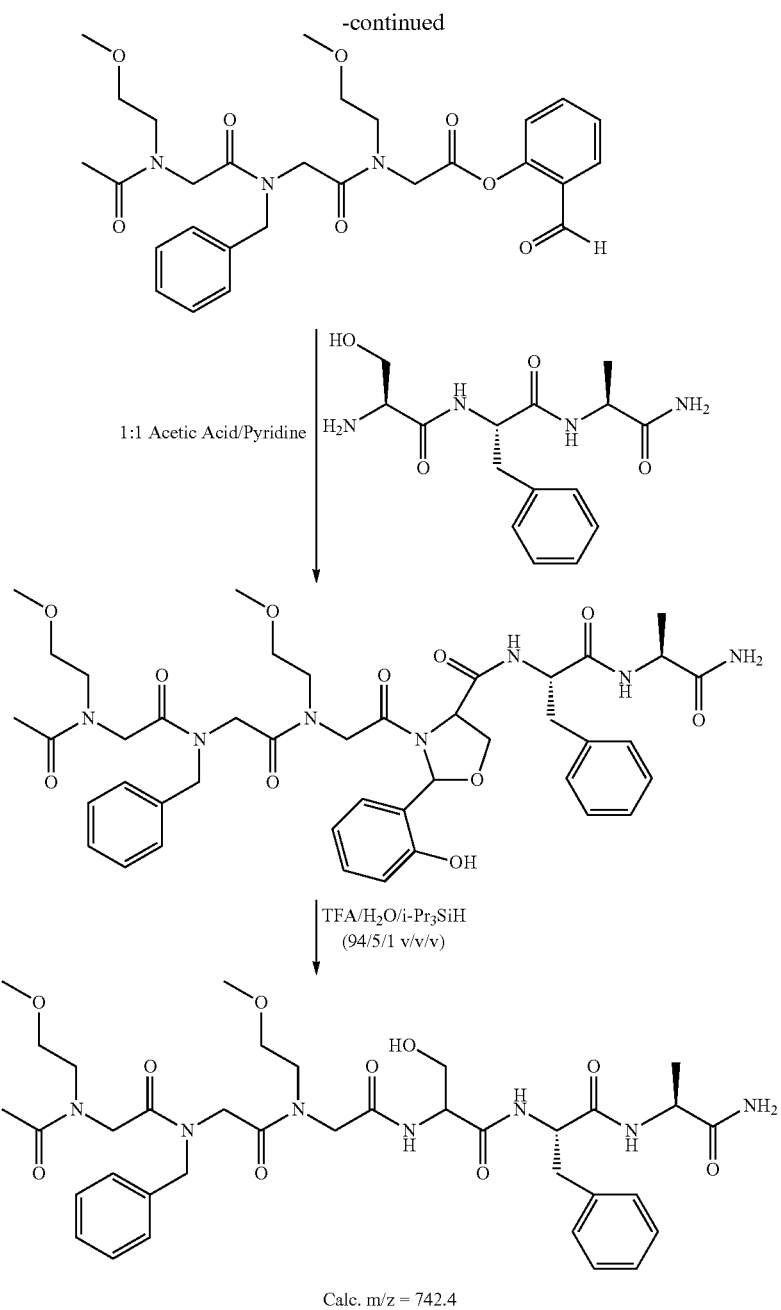

Calc. m/z = 742.4

Upon removal of the acetal group under acidic conditions, the intermediate was rapidly and quantitatively converted to the native amide product.

Because C-terminal β-branched amino acids commonly hinder peptide coupling in cysteine-based NCL reactions, the inventors evaluated ligation efficiency of peptoid salicylaldehyde esters that include steric bulk at the C-terminus (Table 3, Entries 1-4).

Ligation reactions were conducted between N-terminal serine/threonine peptide fragments and peptoid oligomers incorporating N-alkyl or N-aryl side chains at their C-termini (Table 3). The presence of the bulky C-terminal peptoid side-chains does not abrogate rapid coupling kinetics, as these reactions were conducted with ~99% conversion after 1 hr. These N-alkyl or N-aryl peptoid side-chains can promote polyproline I- or polyproline II-type helix formation, respectively, establishing the ability to generate conformationally ordered architectures, including secondary structure motifs that may be of marginal stability for polypeptides.[21,22]

In order to demonstrate that peptoid oligomers, including diverse side chain functional groups, can be ligated using unprotected peptide fragments, coupling was conducted with sequence-diverse peptoid 6 and peptide 7. Electrospray ionization mass spectrometry confirmed the initial formation of the N,O-benzylidene acetal ligation intermediate (calc. m/z: 1,842.0; obs. m/z: 1,842.0) and the peptoid-peptide hybrid product 9 (FIG. 3, calc. m/z: 1,738.9; obs. m/z: 1,738.8, and FIG. 4).

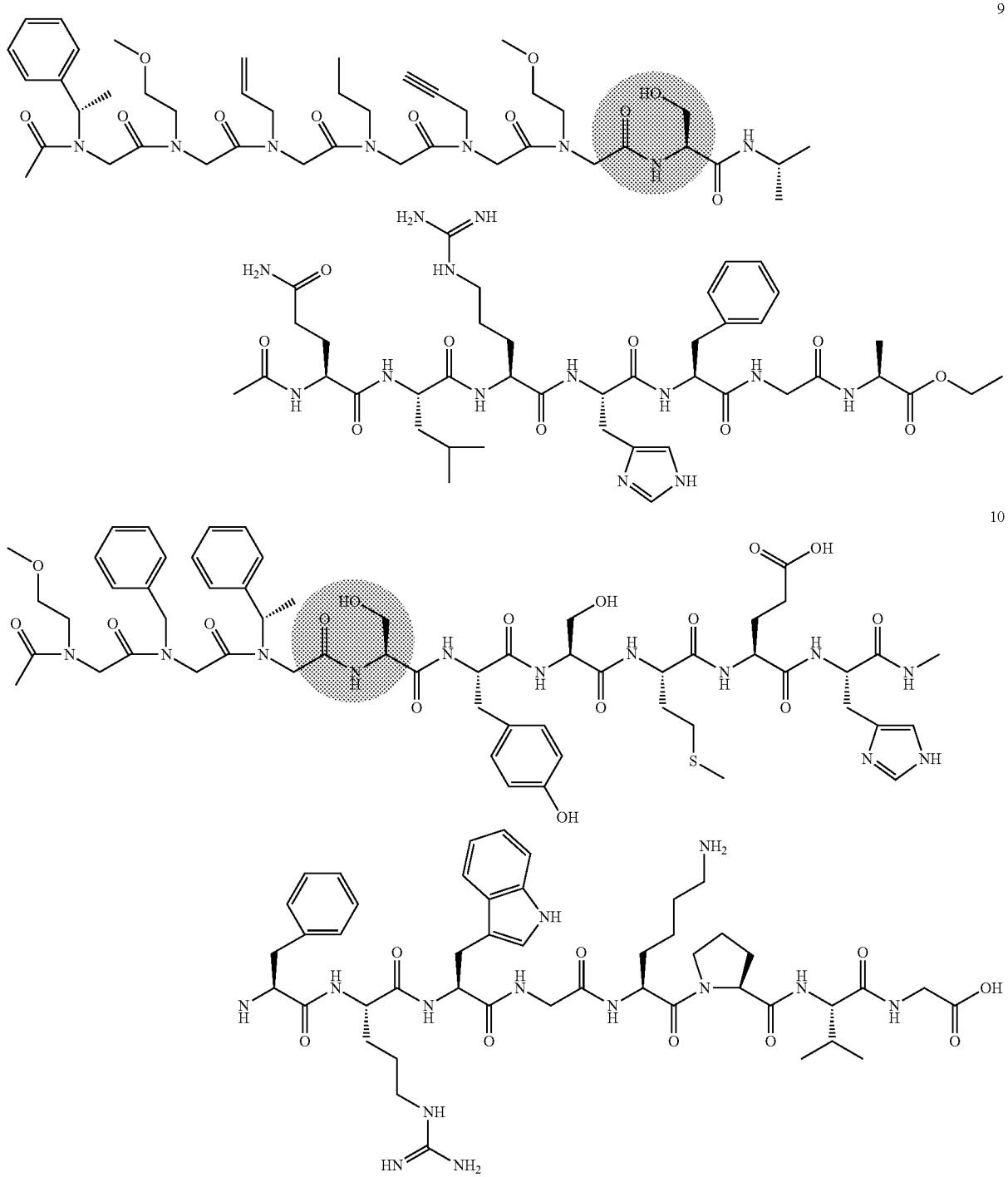

Figure 4:
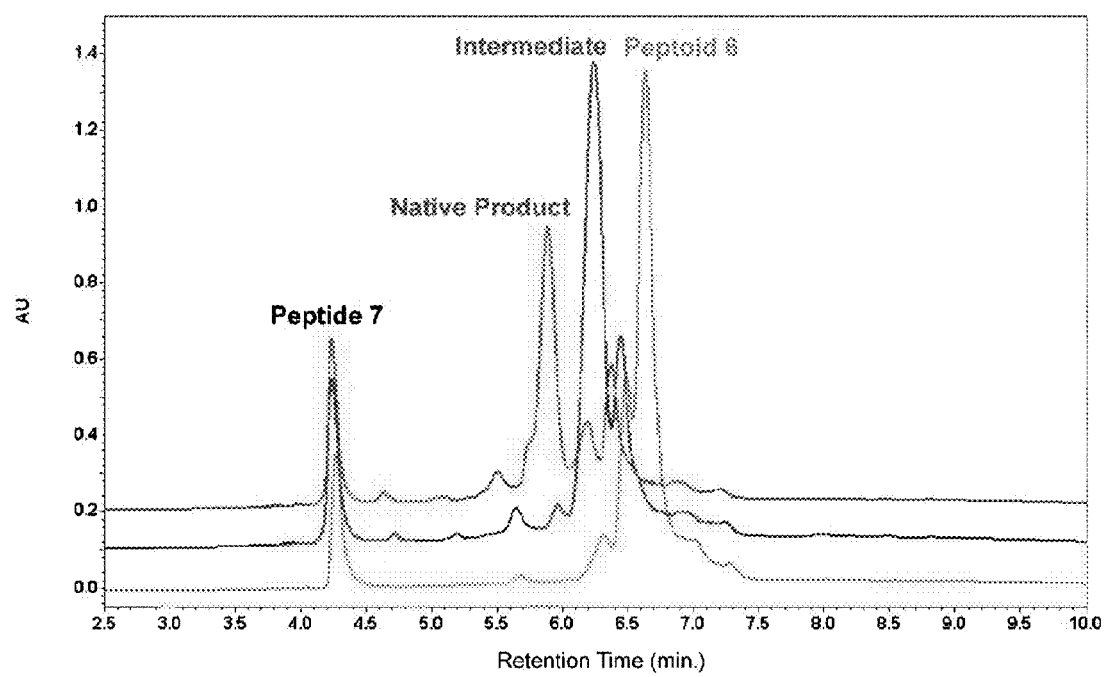
FIG. 4 shows fragment condensation between C-terminal peptoid salicylaldehyde ester 6 and peptide 7 as crude components. The reaction went to completion within 6 hours. Upper traces of intermediate (blue) and native product (red) are offset in y-direction for clarity. Reaction monitored by HPLC (214 nm) and LCMS.

In addition, peptide 8, which incorporates numerous reactive side-chains (i.e., Lys, Glu, Tyr, and Ser) was successfully coupled to peptoid 2, affording the desired ligated product 10 (FIG. 3, calc. m/z: 2,145.0; obs. m/z: 2,144.9, and FIG. 4).

Next, in order to demonstrate that peptoid oligomers, including diverse side chain functional groups, can be ligated using biosynthesized proteins, coupling was conducted with a peptoid and a biosynthesized protein.[20]

Figure 5:
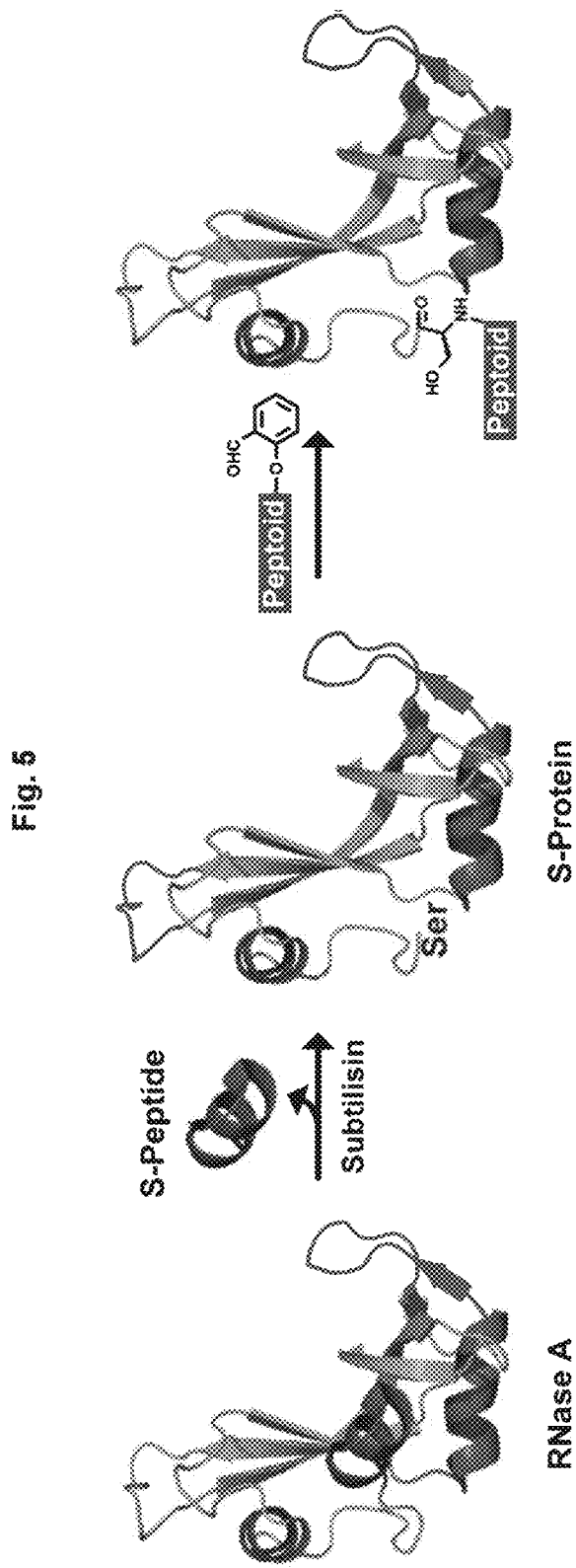
FIG. 5 shows schematic diagram of serine ligation between a peptoid bearing a C-terminal salicylaldehyde ester and the S-protein containing an N-terminal serine residue. Subtilisin cleavage was utilized to prepare the S-protein bearing the N-terminal serine residue. Ligation conditions: pyridine/acetic acid (1:1) at a final protein concentration of 10 mM (16 h, rt).
Figure 6:
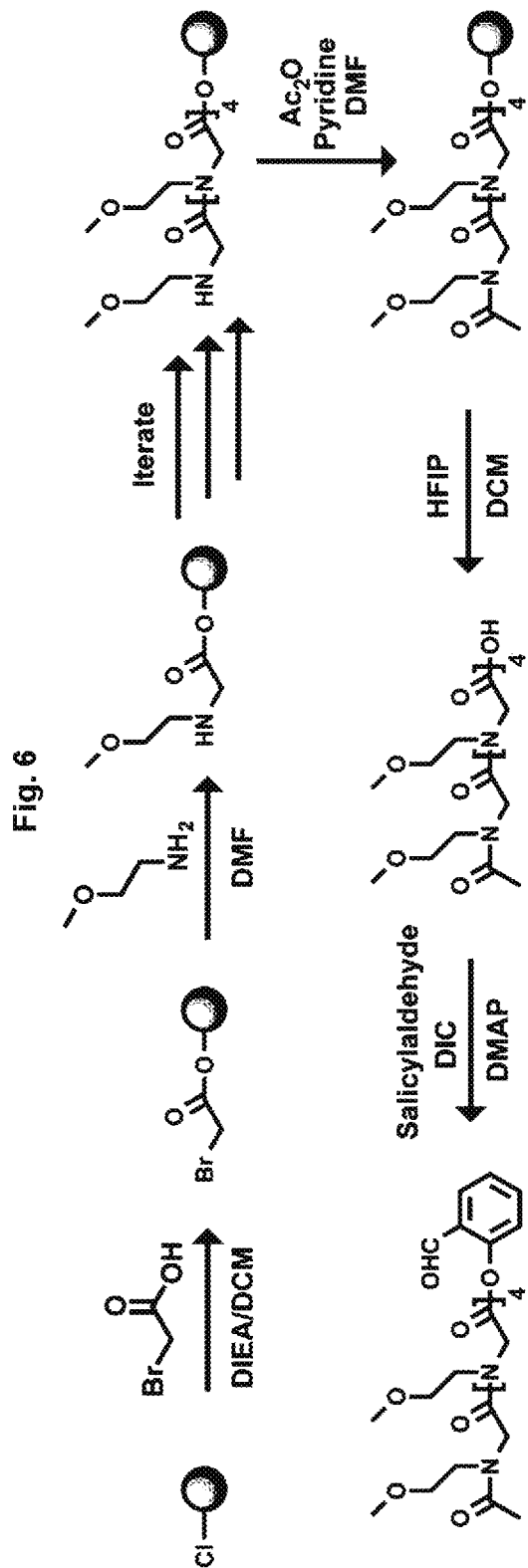
FIG. 6 shows synthesis of C-terminal peptoid salicylaldehyde ester used in RNase ligation study. The peptoid oligomer bearing a C-terminal salicylaldehyde ester was synthesized from 2-chlorotrityl resin.

As a model, the inventors selected bovine pancreatic ribonuclease A (RNase A). The N-terminal portion (residues 1-20), dubbed the S-peptide, can be readily removed by enzymatic cleavage with subtilisin, providing the S-protein which contains an N-terminal serine residue (FIG. 5).[23] Following high-performance liquid chromatography (HPLC) purification and characterization by matrix-assisted laser desorption ionization time-of-flight mass spectrometry (MALDI-TOF), the corresponding S-protein was obtained (calc. m/z: 11,534.3; obs. m/z: 11,533.2). The inventors then synthesized an N-acetylated peptoid pentamer incorporating methoxyethyl side chain groups (Scheme, FIG. 6). The pentamer was converted to the salicylaldehyde ester and coupled to the S-protein, forming the corresponding N,O-benzylidene acetal intermediate. This reaction was monitored by analytical HPLC and MALDI-TOF, which established that coupling was complete after 16 hours. Conversion of the acetal group to the amide via TFA treatment afforded the hybrid protein in 13.5% yield, confirming that peptoid oligomers can be ligated to biosynthesized proteins through native amide linkages.

Figure 7:
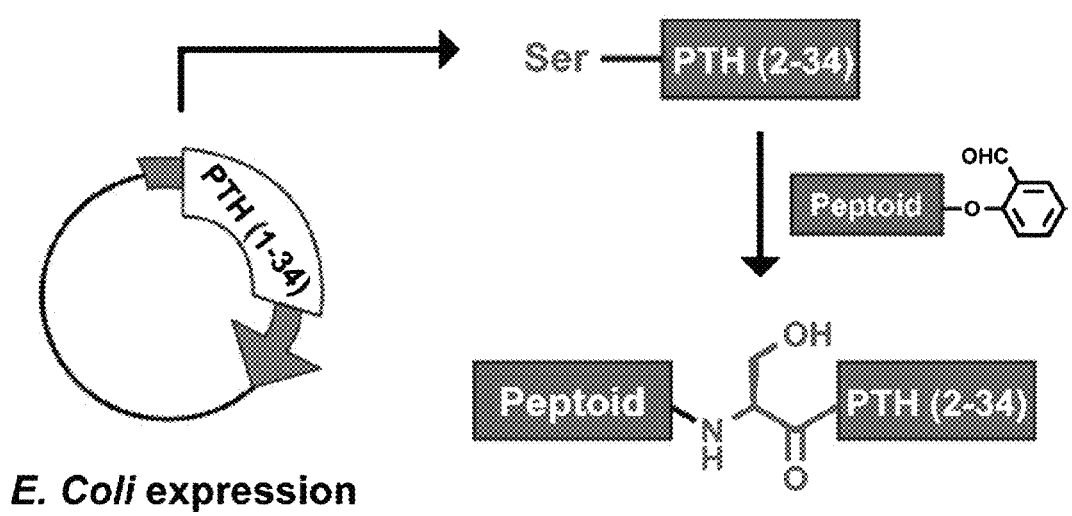
FIG. 7 shows schematic diagram of Ser/Thr ligation. Functionalization of PTH (1-34) was conducted by ligation with a peptide containing a C-terminal salicylaldehyde ester.

Next, the inventors utilized Ser/Thr ligation to generate a variant of parathyroid hormone 1-34 or PTH (1-34) (FIG. 7). PTH (1-34) agonizes the class B G-protein-coupled receptor PTHr1 and is currently marketed (Forteo) to enhance bone density and formation in patients diagnosed with osteoporosis, although it has a poor half-life in serum (~5 min).[25] Following HPLC purification of recombinant PTH (1-34) and characterization by MALDI-TOF (calcd m/z 4,117.7; obsd m/z 4,116.9), an N-(methoxyethyl)glycine (Nme) trimer peptoid oligomer containing a C-terminal salicylaldehyde ester was ligated to recombinant PTH (1-34). The inventors chose to ligate a peptoid oligomer comprising Nme side chains to PTH (1-34) because they share chemical similarities to polyethylene glycol (PEG) units, increase aqueous solubility, and have previously been shown to enhance the bioavailability of therapeutic peptides.[26] Chemoselective fragment condensation was monitored by analytical HPLC and MALDI-TOF, which determined that coupling was complete after 12 h (FIG. 8). Conversion of the acetal group under acidic conditions provided the desired semisynthetic conjugate of PTH (1-34) (calcd m/z: 4,515.9; obsd m/z: 4,514.8, 27.7% yield), confirming that Ser/Thr ligation can be accomplished with recombinant polypeptide fragments.

Figure 9:
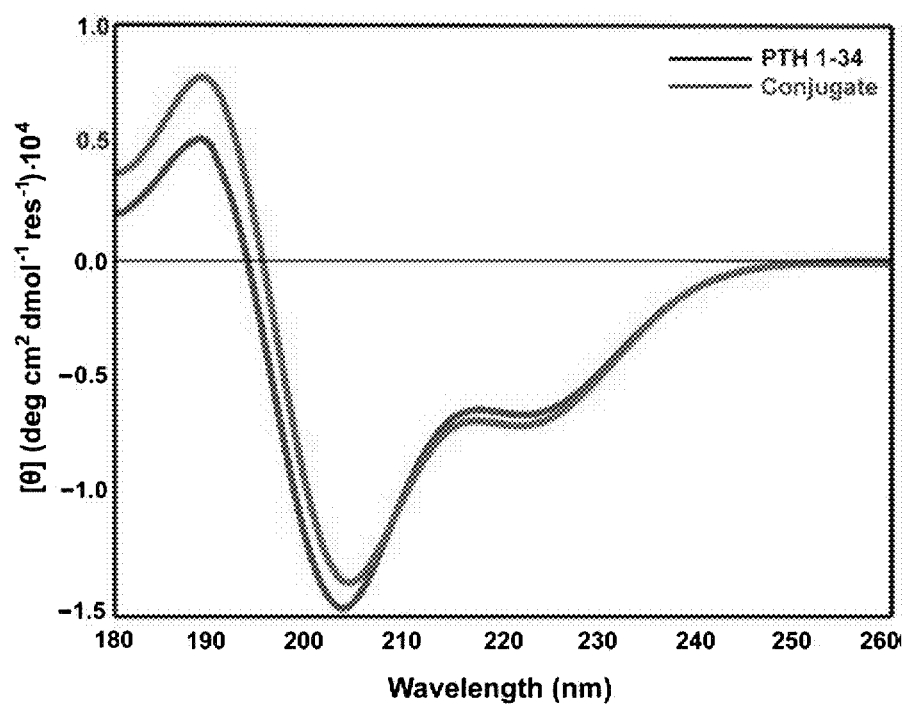
FIG. 9 depicts circular dichroism spectra of PTH (1-34) (blue) and conjugate (red). Scans were performed at 25° C.

To understand the impact on secondary structure of conjugating the peptoid oligomer to the N-terminus of PTH (1-34), the inventors used far-UV circular dichroism (CD) spectroscopy. Wild-type PTH (1-34) and the conjugate were purified to >95% by HPLC and CD spectra were obtained at 25° C. in 10 mM PBS buffer (FIG. 9). When compared to the CD spectrum of PTH (1-34), which exhibits typical helical character with minima near 208 and 222 nm, the conjugate displayed similar secondary structural features as PTH (1-34).[27] These results suggest that this modification at the N-terminus of PTH (1-34) has negligible impact on the structure of the protein. This result is desirable as the helical character at the C-terminus of PTH (1-34) may be critical for recognition by G-protein coupled receptors for PTH (PTHR). In fact, preliminary in vitro biological characterization shows that PTH (1-34) hybrids bearing peptoid oligomers at the N-terminus retain capability as full agonists to the PTH receptor.

The inventors have described a facile chemoselective synthetic route to establish native amide bond formation between peptoid and peptide oligomers. Fragment condensation was rapid, including peptoids containing β-branched side-chains at their C-termini, and the intermediates were quantitatively converted to native amide products. In addition, unprotected oligomer fragments varying in length and sequence were efficiently coupled, establishing the ability to generate highly complex peptoid-peptide hybrids. The inventors anticipate this method will be used to synthesize proteins that integrate structural features from both polypeptides and abiotic oligomers, such as peptoids.

General Synthetic Procedures

The hybrid polymers of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative hybrid polymers that have been listed hereinabove. The hybrid polymers of the invention may be prepared from known or commercially available starting materials and reagents by one skilled in the art of organic synthesis.

Solvents and reagents purchased from commercial sources were used without further purification. Abbreviations for reagents are as follows: 9-fluorenylmethoxycarbonyl (Fmoc); tert-butoxycarbonyl (Boc); benzotriazole-1-yloxy-tris-pyrrolidino-phosphonium hexafluorophosphate (PyBOP); Bromo-tris-pyrrolidino phosphoniumhexafluorophosphate (PyBrOP); trifluoroacetic acid (TFA); hexafluoroisopropyl alcohol (HFIP); methylene chloride (DCM); N,N'-dimethylformamide (DMF); N,N'-diisopropylcarbodiimide (DIC); diisopropylethylamine (DIEA); acetonitrile (ACN); N-methylmorpholine (NMM); O-Benzotriazole-N, N,N',N'-tetramethyl-uronium-hexafluoro-phosphate (HBTU).

The submonomer amines 2-methoxyethylamine, propargylamine, allylamine, propylamine, aniline, (S)-(–)-1-phenylethylamine, and benzylamine were purchased from either Aldrich or TCI America. Other reagents were obtained from commercial sources and used without additional purification.

HPLC analysis and purifications were performed on a Beckman Coulter System Gold instrument. For analytical analysis, a $C_{18}$ reversed-phase HPLC column was used (Peeke Scientific). Samples were eluted with a 5-95% acetonitrile/water gradient (0.1% TFA) in 10 minutes with a flow rate of 0.7 mL/min and monitored at 214 nm. For purifications, semi-preparative $C_{18}$ reversed-phase HPLC columns were used (Peeke Scientific). Samples were eluted with a 5-95% acetonitrile/water gradient (0.1% TFA) in 50 minutes with a flow rate of 2.5 mL/min, and monitored at 230 nm.

Mass spectrometry was performed on an Agilent 1100 Series Capillary LCMSD Trap XCT system mass spectrometer (electrospray-ion trap) or a Bruker OmniFLEX MALDI-TOF mass spectrometer.

Representative Synthetic Methods

Synthesis of Peptoid Oligomers and General Ligation Reaction Conditions

Example 1

Synthesis of Peptoid Fragments

Peptoid oligomers were synthesized on 2-chlorotrityl resin (Novabiochem). The resin (100 mg) was swollen in 3 mL of dichloromethane (DCM) for 5 min. and washed twice (3 mL DCM) for 1 min. Bromoacetic acid (90.3 mg), N,N-diisopropylethylamine (DIPEA) (107 μL) and 1 mL of DCM were added, and the mixture was stirred for 40 min. Washing steps using DCM (3×2 mL) and DMF (4×2 mL) were performed and 1.0 mL of corresponding amine in DMF (10 mL/g resin) was added and the reaction was shaken for 30 min (Step A). Following the washing, bromoacetic acid (0.167 g/1 mL DMF) and diisopropylcarbodiimide (DIC, 2 mL/g resin) in DMF were added to the resin and the mixture was allowed to shake at rt for 20 min (Step B). Steps A and B were then repeated until peptoid oligomers of desired length were obtained. Prior to cleavage, peptoid oligomers were taken up in 3 mL of a 1:2:3 (acetic anhydride/pyridine/DMF) solution for 2 hours to obtain N-terminal acetylated peptoid oligomers. The 2-chlorotrityl resin was then cleaved with 20% hexafluoroisopropanol in DCM and the peptoid was lyophilized overnight. An equimolar amount of salicylaldehyde solution was prepared in dry DCM (2-4 mL) and a slight excess of DIC (1.2 equiv.) and a catalytic amount of DMAP (0.1 equiv.) were added to the peptoid. The reaction(s) were allowed to proceed for 6-24 hours. The resulting peptoid esters were purified by HPLC, and lyophilized overnight. The mass spectral data for the peptoid and peptide oligomers is tabulated in Table 1.

TABLE 1

MS Characterization of Peptoid and Peptide Oligomers

| Entry | Compounds | Calculated Mass (m/z) | Observed Mass (m/z) |
| --- | --- | --- | --- |
| 1 | 1 | 541.2 | 564.1[a] |
| 2 | 2 | 587.3 | 609.9[a] |
| 3 | 3 | 559.2 | 581.9[a] |
| 4 | 4 | 322.2 | 344.9[a] |
| 5 | 5 | 336.2 | 358.9[a] |
| 6 | 6 | 846.2 | 868.9[a] |
| 7 | 7 | 1,013.5 | 1,014.7[b] |
| 8 | 8 | 1,680.9 | 1,680.6[b] |

Mass spectrometry data for peptoid and peptide oligomers acquired using ESI techniques.
[a][M + Na].
[b]Mass spectrometry data for peptide oligomer acquired using MALDI-TOF techniques General Procedure for Ligation:

The peptide fragment (1.1 equiv.) and the peptoid phenyl ester fragment (1.0 equiv.) were dissolved in pyridine/acetic acid (1:1 mole/mole) to a final concentration of 0.05 M. The reaction was stirred at room temperature and monitored using LCMS and HPLC. Following completion of the reaction (consumption of salicylaldehyde to form the acetal intermediate), the solvent was removed by lyophilization and the intermediate product was treated with TFA/H$_2$O/i-Pr$_3$SiH (94/5/1, v/v/v) for 10 min to give the product containing a native amide bond at the ligation site. The mass spectral data for the intermediate oxazolidines is given in Table 2.

TABLE 2

MS Characterization of Intermediate Oxazolidine Products

| Entry | Compounds | Calculated Mass (m/z) | Observed Mass (m/z) |
| --- | --- | --- | --- |
| 1 | 1 + 4 | 845.4 | 867.9[a] |
| 2 | 2 + 4 | 891.4 | 913.8[a] |
| 3 | 2 + 5 | 905.4 | 927.9[a] |
| 4 | 3 + 4 | 863.4 | 885.9[a] |
| 5 | 3 + 5 | 877.4 | 899.9[a] |
| 6 | 2 + 8 | 2,249.0 | 2,250.7[b] |

Mass spectrometry data for peptoid and peptide oligomers acquired using ESI techniques. The conversion is calculated based on the consumption of the salicylaldehyde.
[a][M + Na].
[b]Mass spectrometry data for oligomer acquired using MALDI-TOF techniques.

TABLE 3

Ligation efficiency of peptoid salicylaldehyde esters displaying steric bulk at the C-terminus with peptides containing N-terminal serine or threonine residues.

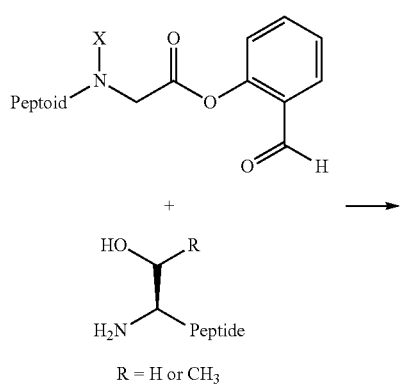

R = H or CH$_3$

TABLE 3-continued

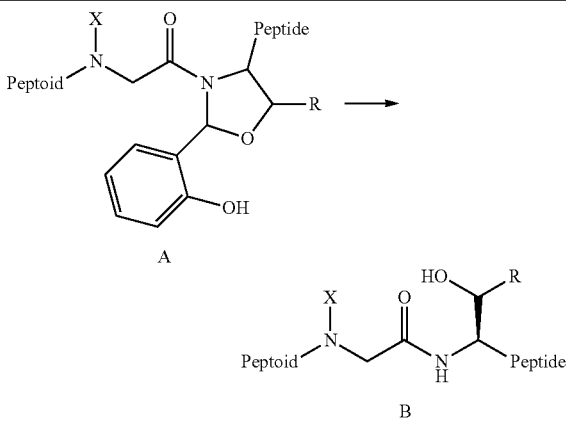

| Entry | Peptoid | Peptide | A[a] (%) | B[b] (%) | B Calc. m/z | B Obs. m/z |
|---|---|---|---|---|---|---|
| 1 | 2 | 4 | 99 | 99 | 787.4 | 787.9 |
| 2 | 2 | 5 | 99 | 99 | 801.4 | 801.7 |
| 3 | 3 | 4 | 99 | 99 | 759.4 | 759.9 |
| 4 | 3 | 5 | 99 | 99 | 773.4 | 773.9 |

[a] Reaction conversion after 1 hr. The conversion was monitored by HPLC and was calculated based on the consumption of the salicylaldehyde.
[b] Deprotection conversion after 10 min. The conversion was monitored by HPLC and was calculated based on the consumption of the N,O-benzylidene acetal intermediate. X denotes (S)-N-1-phenylethyl glycine (peptoid 2) or N-aryl glycine (peptoid 3).

Example 2

Hybrid Polymers comprising RNase

General—The submonomer amine 2-methoxyethylamine, Ribonuclease A (≥60% (SDS-PAGE)), and subtilisin were purchased from Sigma Aldrich. Other reagents were obtained from commercial sources and used without additional purification. Forteo was obtained as the recombinantly expressed product in buffer solution (0.41 mg/mL acetic acid, 0.1 mg/mL sodium acetate (anhydrous), 45.4 mg/mL mannitol, 3 mg/mL metacresol). Semipreparative HPLC was conducted to extract Forteo from buffered solution. HPLC analysis and purifications were performed on a Beckman Coulter System Goldinstrument. For analytical analysis, a C18 reversed-phase HPLC column was used (Peeke Scientific). Samples were eluted with a 5-95% acetonitrile/water gradient (0.1% TFA) in 10 minutes or 30 minutes with a flow rate of 0.7 mL/min and monitored at 214 nm. For purifications, semi-preparative C18 or C4 reversed-phase HPLC columns were used (Peeke Scientific). Samples were eluted with a 5-95% acetonitrile/water gradient (0.1% TFA) in 50 minutes with a flow rate of 2.5 mL/min, and monitored at 214 nm. All HPLC chromatograms in main text are of purified material.

All mass spectrometry data was obtained on a Bruker UltrafleXtreme MALDI-TOF mass spectrometer in positive-ion mode. Matrix: Sinapic acid in acetonitrile with 0.01% TFA.

Circular Dichroism (CD) Spectroscopy:

Circular Dichroism spectra were measured on an Aviv spectrophotometer (Lakewood, N.J.). Spectra were acquired at concentrations of 10 μM oligomer in 10 mM PBS (pH 7.4) in a 1 mm cuvette. Wavelength-dependent spectra were acquired from 260 nm to 180 nm (data pitch 0.5 nm, scan speed 50 nm/min, 4 sec, 1 nm bandwidth and 10 accumulations). Mean residue ellipticity values were calculated from the equation MRE=(Θsample−Θbuffer)/(L·c·n), where Θ is observed signal in millidegrees, L is the length of the cuvette in cm, c is the concentration of peptide in dmol/cm3, and n is the number of residues in the peptide and peptoid oligomers.

Preparation of S-Protein: S-protein was prepared as previously reported.[23]

Synthesis of Peptoid Fragments: Peptoids were prepared as described herein (Example 1) and as reported by Levine et al.[24]

Figure 10:
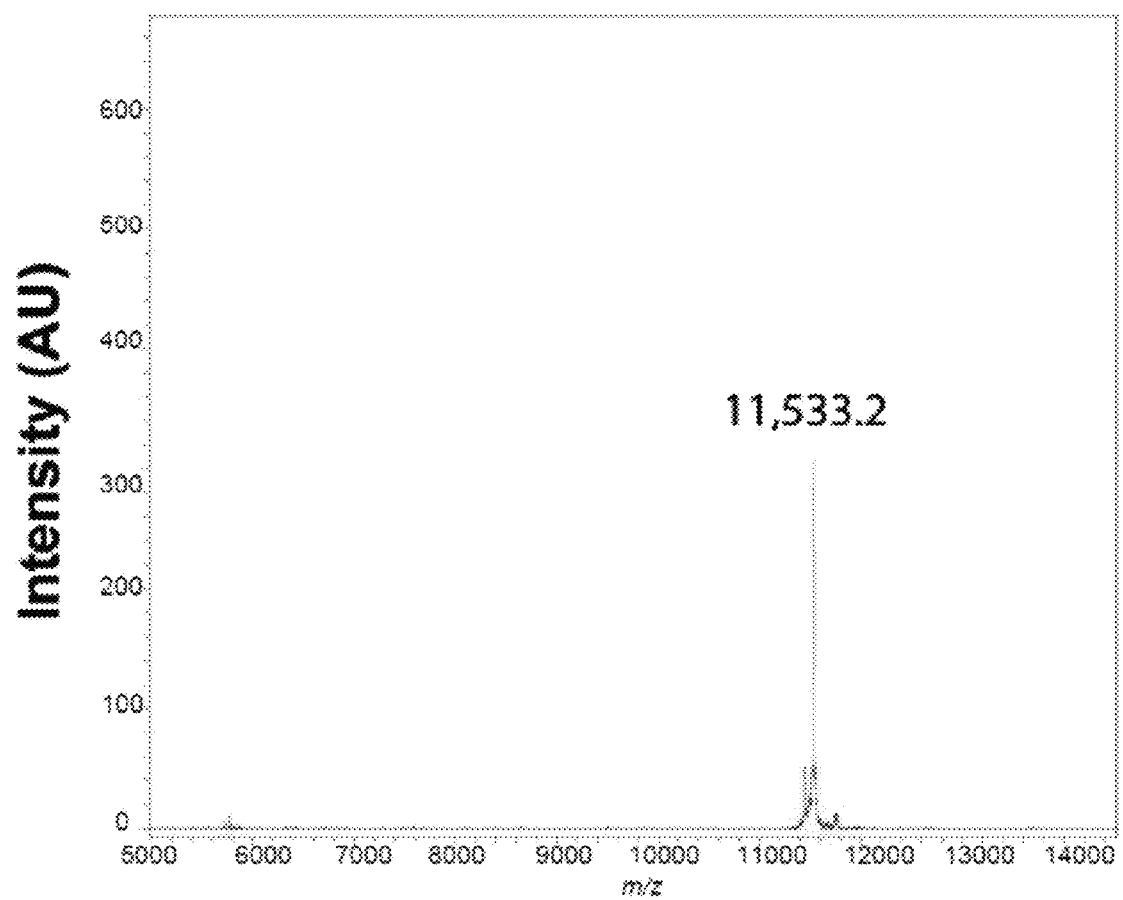
FIG. 10 shows mass spectrometry data acquired using MALDI-TOF techniques to monitor ligation reaction between peptoid oligomer and S-protein. Top: S-protein, Middle: N,O-benzylidene acetal intermediate, Bottom: Native semi-synthetic protein.
Figure 10:
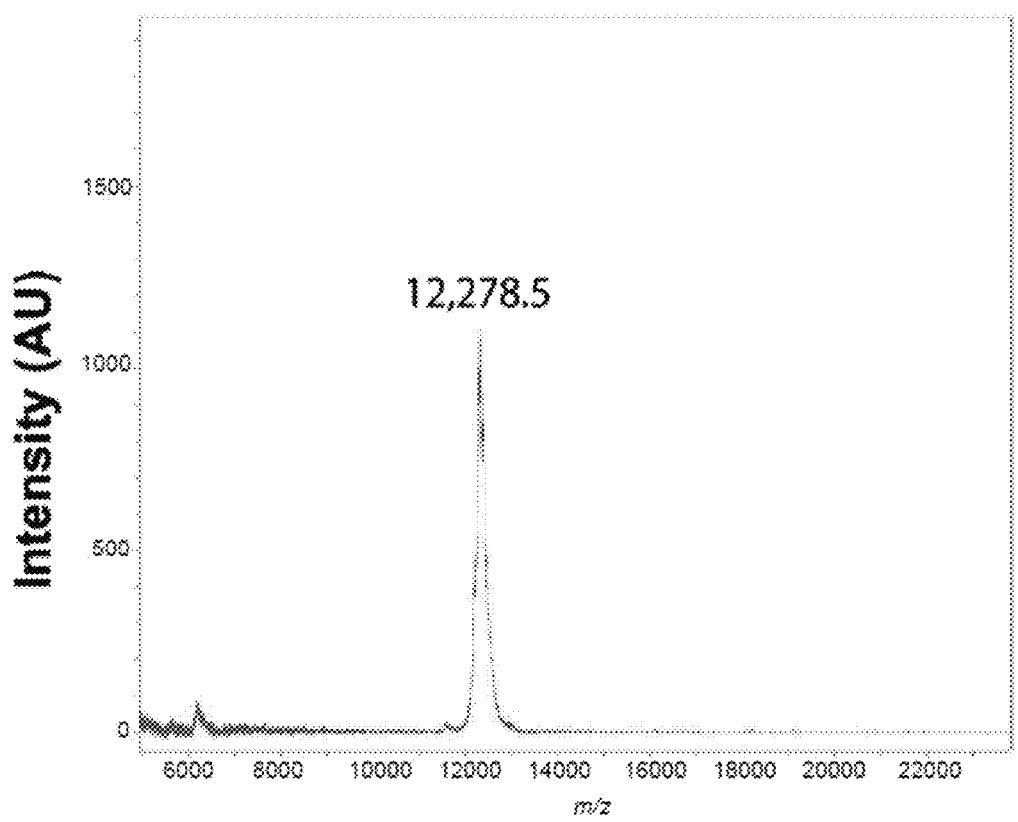
Figure 10:
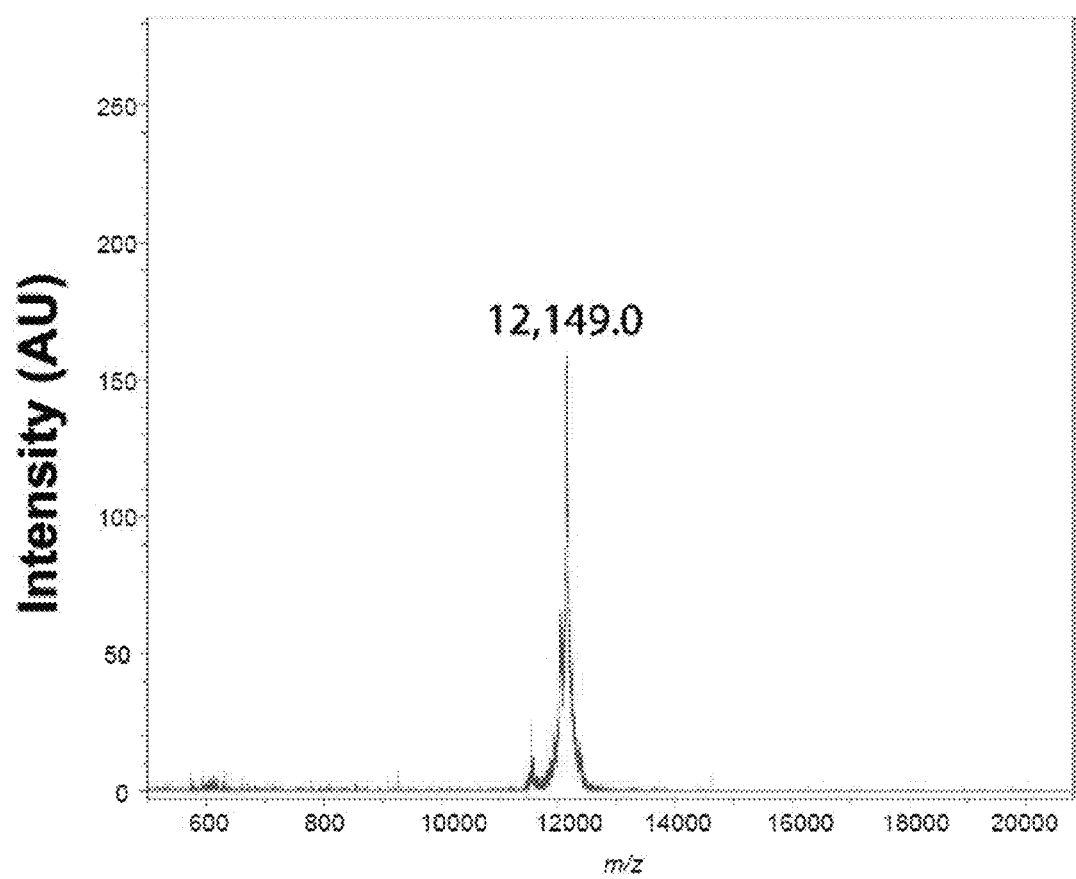
Figure 11:
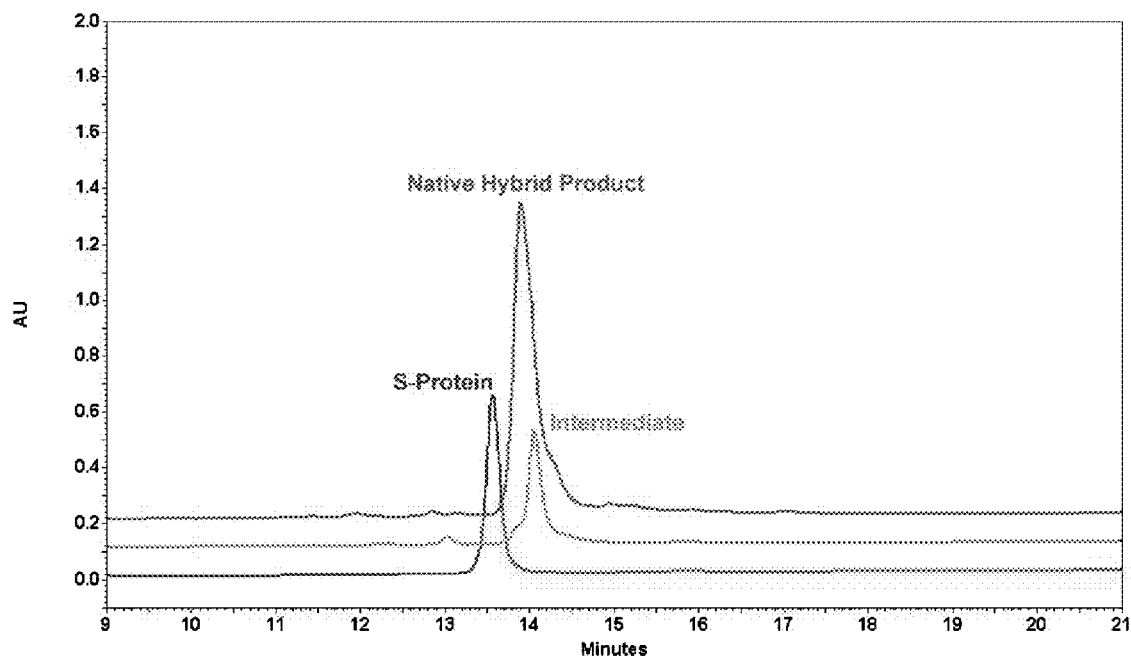
FIG. 11 shows fragment condensation between C-terminal peptoid salicylaldehyde ester and the S-protein. The reaction went to completion within 16 hours. Intermediate trace (green) is of crude reaction between purified S-Protein (purple) and purified peptoid oligomer (not shown). Trace of native product (red) is of purified compound. Green and red traces are offset in y-direction for clarity. Reaction monitored at 214 nm.

General Procedure for Ligation: 1 mg of Forteo or 5 mg of S-protein were dissolved in pyridine/acetic acid (1:1 mole/mole) to a final concentration of ~10 mM, depending on solubility, and the peptoid fragment (1.1 equiv.) was added. The reaction was stirred at room temperature and monitored using MALDI-TOF and HPLC (FIGS. 10 and 11). Following completion of the reaction (consumption of salicylaldehyde to form the acetal intermediate), the solvent was removed by lyophilization and the intermediate product was treated with TFA/H$_2$O/i-Pr$_3$SiH (94/5/1, v/v/v) for 10 min to give the product containing a native amide bond at the ligation site.

Additional Exemplary Hybrid polymers of the Invention

Compound 11 (1 + 4)
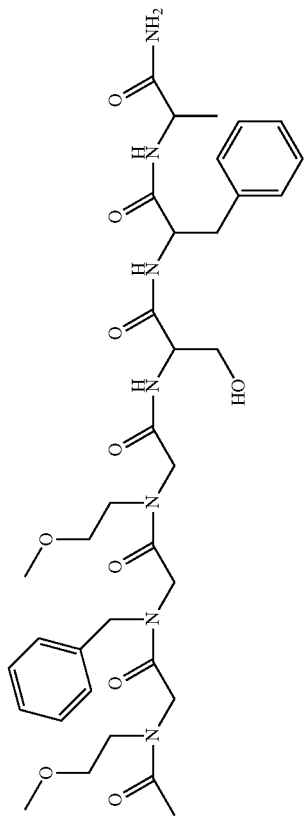
Compound 12 (1 + 5)
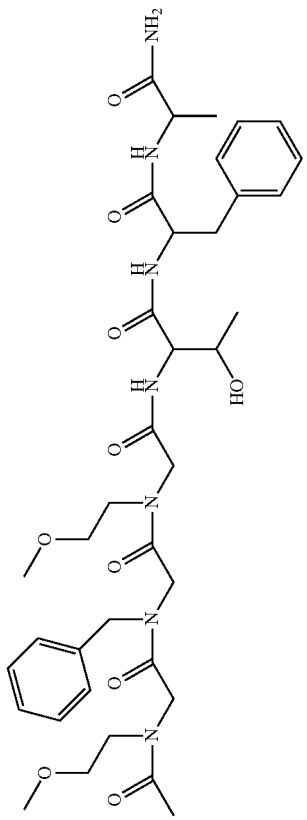
Compound 13 (2 + 4)
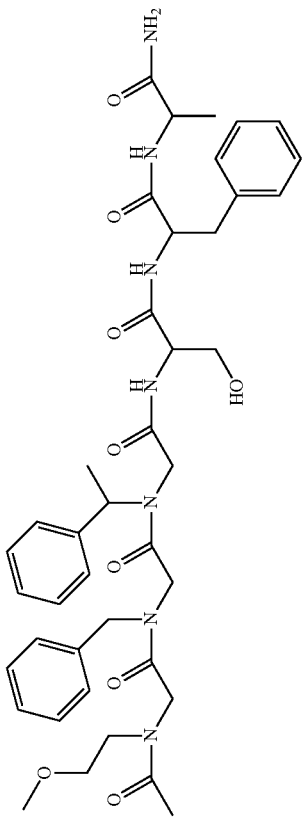

Compound 14 (2 + 5)
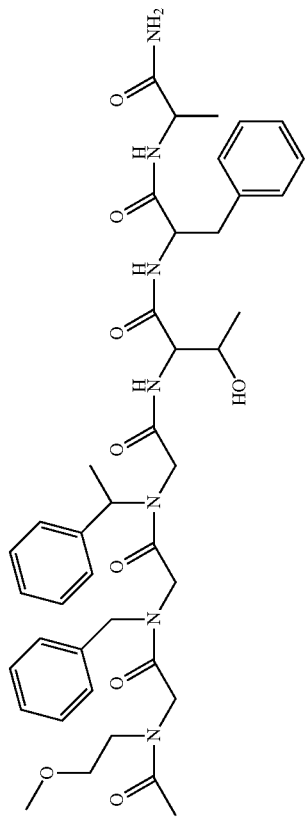
Compound 15 (3 + 4)
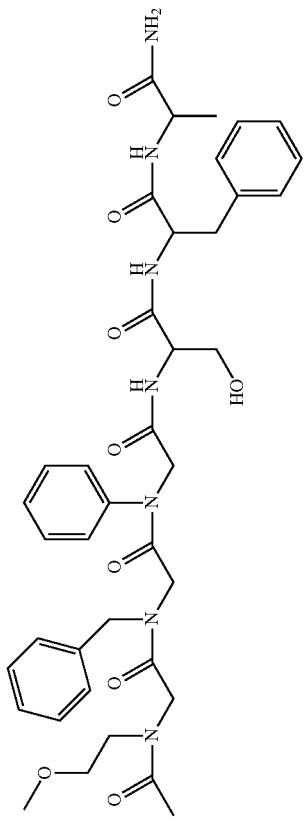
Compound 16 (3 + 5)
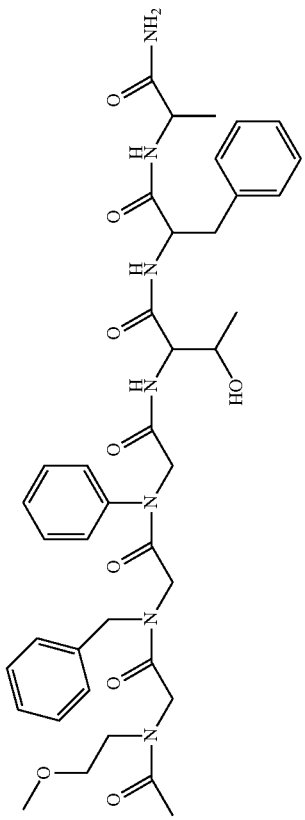

-continued
Compound 17 (6 + 4)
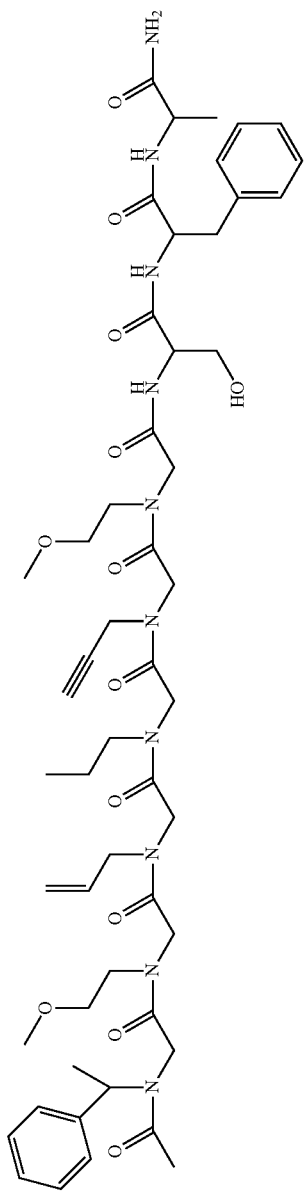
Compound 18 (6 +5)
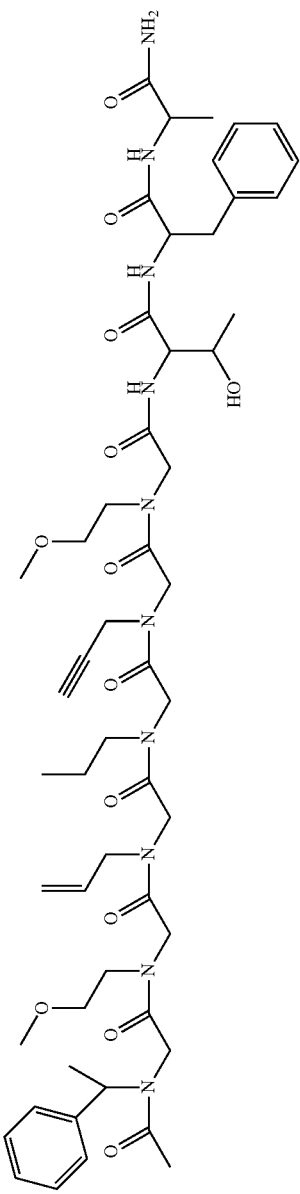
Compound 19 (1 + 7)
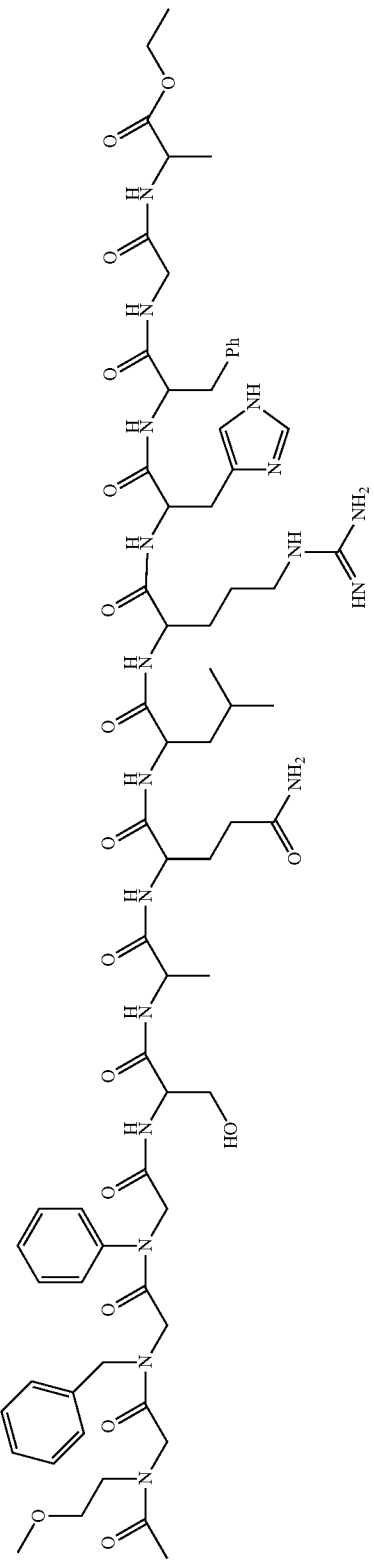

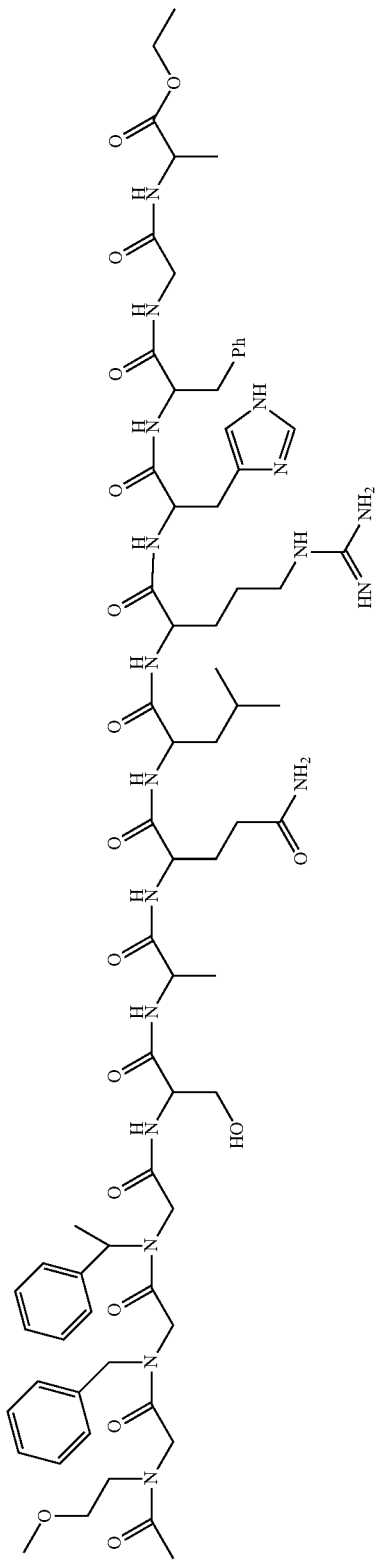
Compound 20 (2 + 7)
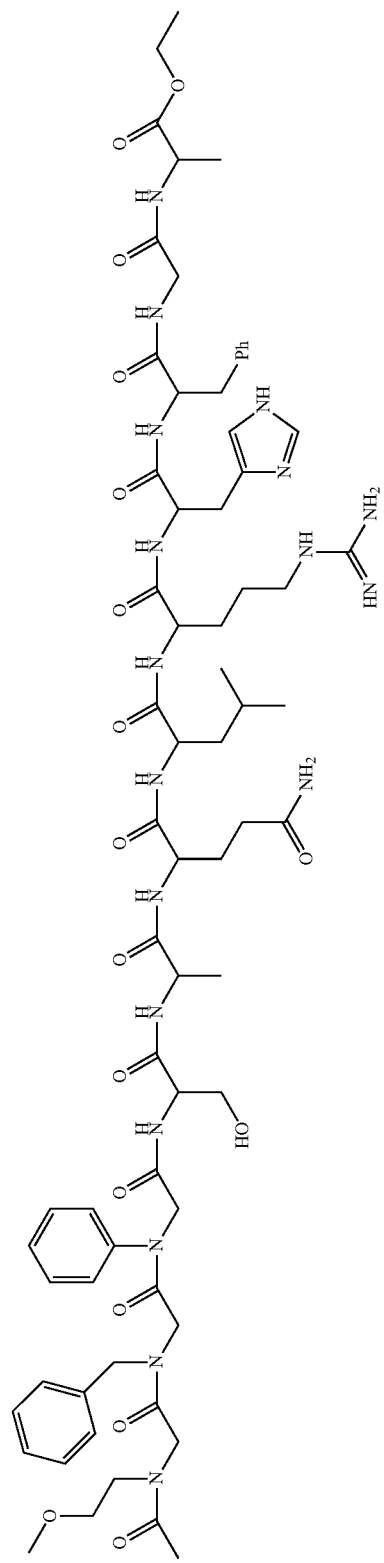
Compound 21 (3 + 7)

-continued
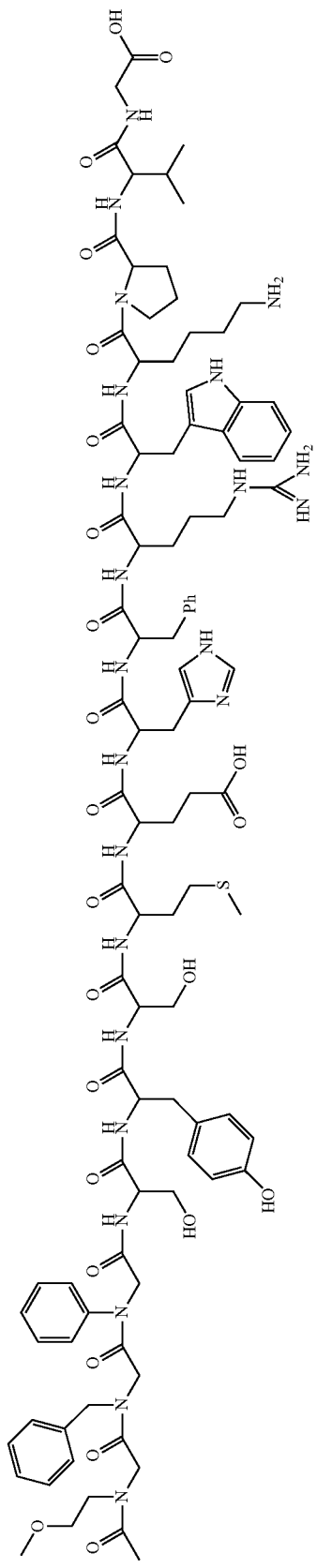
Compound 22 (1 + 8)
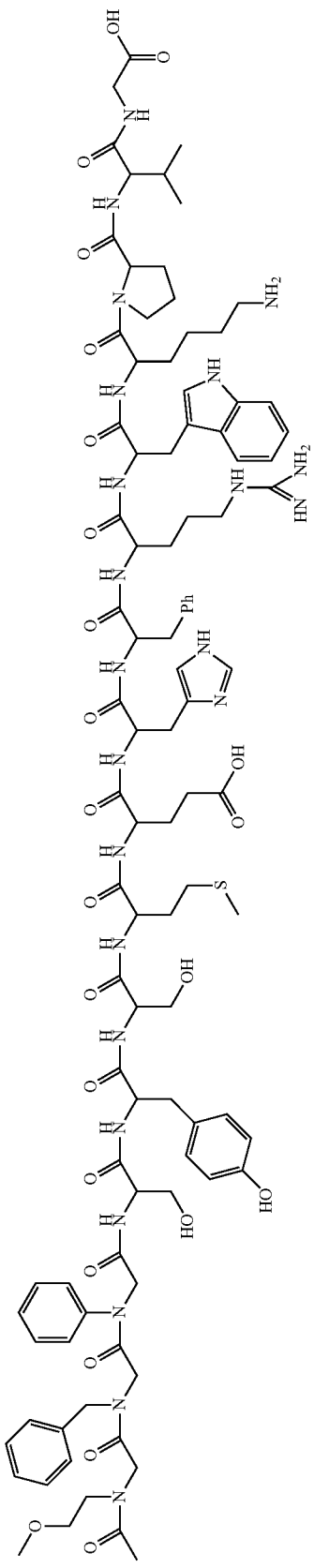
Compound 23 (3 + 8)
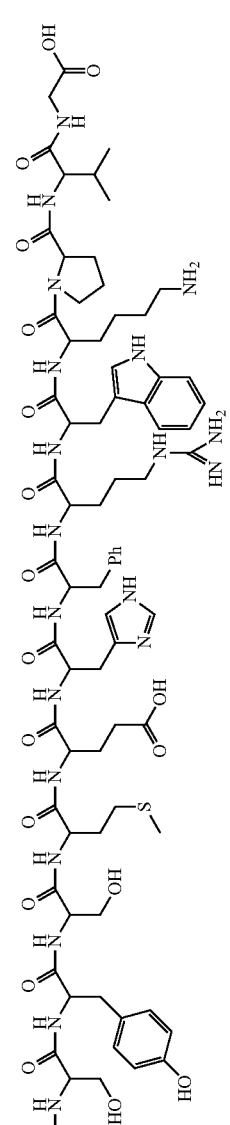
Compound 24 (6 + 8)

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for peptoid oligomers are approximate, and are provided for description.

All publications, including but not limited to patents and patent applications, cited in this specification are herein incorporated by reference as if each individual publication were specifically and individually indicated to be incorporated by reference herein as though fully set forth.

REFERENCES

1. U. Arnold, M. P. Hinderaker, B. L. Nilsson, B. L. Huck, S. H. Gellman and R. T. Raines, *J. Am. Chem. Soc.*, 2002, 124, 8522.
2. (a) S. Batjargal, Y. J. Yang, J. M. Goldberg, R. F. Wissner and E. J. Petersson, *J. Am. Chem. Soc.*, 2012, 134, 9172. (b) U. Arnold, M. P. Hinderaker, J. Köditz, R. Ulbrich-Hofmann and R. T. Raines, *J. Am. Chem. Soc.*, 2003, 125, 1700. (c) A. Tam, U. Arnold, M. P. Hinderaker and R. T. Raines, *J. Am. Chem. Soc.*, 2007, 129, 12670. (d) X. Lu, S. K. Olsen, A. D. Capili, J. S. Cisar, C. D. Lima and D. S. Tan, *J. Am. Chem. Soc.*, 2010, 132, 1748. (e) A. A. Fuller, D. Du, F. Liu, J. E. Davoren, G. Bhabha, G. Kroon, D. A. Case, H. J. Dyson, E. T. Powers, P. Wipf, M. Gruebele and J. W. Kelly, *Proc. Natl. Acad. Sci. U.S.A.*, 2009, 106, 11067. (f) I. E. Valverde, F. Lecaille, G. Lalmanach, V. Aucagne and A. F. Delmas, *Angew. Chem. Int. Ed.*, 2012, 51, 718. (g) R. David, R. Günther, L. Baumann, T. Lühmann, D. Seebach, H.-J. Hofmann and A. G. Beck-Sickinger, *J. Am. Chem. Soc.*, 2008, 130, 15311. (h) B. R. Green, P. Catlin, M. M. Zhang, B. Fiedler, W. Bayudan, A. Morrison, R. S. Norton, B. J. Smith, D. Yoshikami, B. M. Olivera and G. Bulaj, *Chem. Biol.*, 2007, 14, 399.
3. R. N. Zuckermann, J. M. Kerr, S. B. H. Kent, and W. H. Moos, *J. Am. Chem. Soc.*, 1992, 114, 10646.
4. G. Maayan, M. D. Ward and K. Kirshenbaum, *Proc. Natl. Acad. Sci.*, 2009, 106, 13679.
5. D. G. Udugamasooriya, S. P. Dineen, R. A. Brekken and T. Kodadek, *J. Am. Chem. Soc.*, 2008, 130, 5744.
6. J. E. Murphy, T. Uno, J. D. Hamer, F. E. Cohen, V. Dwarki, and R. N. Zuckermann, *Proc. Natl. Acad. Sci.*, 1998, 95, 1517.
7. (a) B. Yoo and K. Kirshenbaum, *Curr. Opin. Chem. Biol.*, 2008, 12, 714. (b) J. R. Stringer, J. A. Crapster, I. A. Guzei and H. E. Blackwell, *J. Am. Chem. Soc.*, 2011, 133, 15559.
8. S. B. L. Vollrath, S. Base and K. Kirshenbaum, *Chem. Sci.*, 2012, 3, 2726.
9. (a) P. Dawson, T. Muir, I. Clark-Lewis and S. Kent, *Science*, 1994, 266, 776. (b) J. M. Monbaliu and A. R. Katritzky, *Chem. Commun.*, 2012, 48, 11601.
10. (a) G.-M. Fang, H.-K. Cui, J.-S. Zheng and L. Liu, *ChemBioChem*, 2010, 11, 1061. (b) Q. Wan, J. Chen, Y. Yuan and S. J. Danishefsky, *J. Am. Chem. Soc.*, 2008, 130, 15814.
11. G.-M. Fang, Y.-M. Li, F. Shen, Y.-C. Huang, J.-B. Li, Y. Lin, H.-K. Cui and L. Liu, *Angew. Chem. Int. Ed.*, 2011, 50, 7645.
12. J. B. Blanco-Canosa and P. E. Dawson, *Angew. Chem. Int. Ed.*, 2008, 47, 6851.
13. (a) L. R. Malins, K. M. Cergol and R. J. Payne, *ChemBioChem*, 2013, 14, 559. (b) S. D. Townsend, Z. Tan, S. Dong, S. Shang, J. A. Brailsford, and S. J. Danishefsky, *J. Am. Chem. Soc.*, 2012, 134, 3912. (c) P. Siman, S. V. Karthikeyan and A. Brik, *Org. Lett.*, 2012, 14, 1520. (d) Z. Tan, S. Shang and S. J. Danishefsky, *Angew. Chem. Int. Ed.*, 2010, 49, 9500. (e) Z. Harpaz, P. Siman, K. S. A. Kumar and A. Brik, *ChemBioChem*, 2010, 11, 1232. (f) R. L. Yang, K. K. Pasunooti, F. P. Li, X. W. Liu, and C. F. J. Liu, *J. Am. Chem. Soc.*, 2009, 131, 13592. (g) K. S. A. Kumar, M. Haj-Yahya, D. Olschewski, H. A. Lashuel and A. Brik, *Angew. Chem. Int. Ed.*, 2009, 48, 8090. (h) J. Chen, Q. Wan, Y. Yuan, J. Zhu and S. J. Danishefsky *Angew. Chem. Int. Ed.*, 2008, 47, 8521. (i) C. Hasse, H. Rohde and O. Seitz, *Angew. Chem. Int. Ed*, 2008, 47, 6807. (j) Q. Wan and S. J. Danishefsky, *Angew. Chem. Int. Ed.*, 2007, 46, 9248.
14. J. W. Bode, R. M. Fox and K. D. Baucom, *Angew. Chem. Int. Ed.*, 2006, 45, 1248.
15. (a) E. Saxon, J. I. Armstrong, and C. R. Bertozzi, *Org. Lett.*, 2000, 2, 2141. (b) B. L. Nilsson, R. J. Hondal, M. B. Soellner and R. T. Raines, *J. Am. Chem. Soc.*, 2003, 125, 5268.
16. (a) X. Li, H. Y. Lam, Y. Zhang and C. K. Chan, *Org. Lett.*, 2010, 12, 1724. (b) Y. Zhang, C. Xu, H. Y. Lam, C. L. Lee and X. Li, *Proc. Natl. Acad. Sci.*, DOI: 10.1073/pnas.1221012110.
17. T. Horn, B.-C. Lee, K. A. Dill and R. N. Zuckermann, *Bioconj. Chem.* 2004, 15, 428.
18. H. K. Murnen, A. R. Khokhlov, P. G. Khalatur, R. A. Segalman and R. N. Zuckermann, *Hybrid polymers*, 2012, 45, 5229.
19. B. Yoo and K. Kirshenbaum, *J. Am. Chem. Soc.*, 2005, 127, 17132.
20. B.-C. Lee and R. N. Zuckermann, *ACS Chem. Biol.*, 2011, 6, 1367.
21. N. H. Shah, G. L. Butterfoss, K. Nguyen, B. Yoo, R. Bonneau, D. L. Rabenstein and K. Kirshenbaum, *J. Am. Chem. Soc.*, 2008, 130, 16622.
22. K. Kirshenbaum, A. E. Barron, R. A. Goldsmith, P. Armand, E. K. Bradley, K. T. V. Truong, K. A. Dill, F. E. Cohen and R. N. Zuckermann, *Proc. Natl. Acad. Sci.*, 1998, 95, 4303.
23. A. T. Fafarman and S. G. Boxer, *J. Phys. Chem. B*, 2010, 114, 13, 536.
24. P. M. Levine, T. W. Craven, R. Bonneau, and K. Kirshenbaum, *Org. Biomol. Chem.*, 2013, 11, 4142.
25. Narayanan, D.; Anith, A.; Chemazhi, K. P. Mol. *Pharmaceutics*, 2013, 10, 4159.
26. Park, M.; Jardetsky, T. S.; Barron, A. E. *Biopolymers* 2011, 96, 688.
27. Pellegrini, M.; Royo, M.; Rosenblatt, M.; Chorev, M.; Mierke, D. F. *J. Biol. Chem.* 1998, 273, 10420

What is claimed is:

1. A hybrid polymer comprising an abiotic oligomer segment and a polypeptide segment; and wherein the polypeptide segment comprises at least one serine or threonine residue at its N-terminus, and the abiotic oligomer segment is bonded to the polypeptide through the serine or the threonine residue; and wherein the said abiotic oligomer segment comprises N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas or any combinations thereof;
provided that the hybrid polymer is other than HP1, HP2, HP3, HP4, HP5, or HP6.

2. The hybrid polymer according to claim 1, wherein the hybrid polymer is according to formula I:

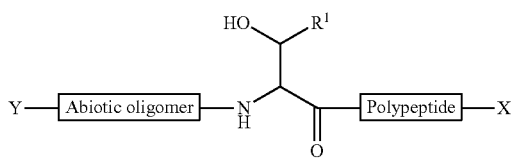

or a pharmaceutically acceptable salt, stereoisomer, isotopic variant or tautomer thereof;
wherein
abiotic oligomer is selected from N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas;
the group

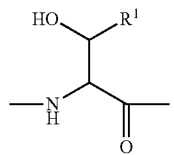

is a serine or threonine residue;
X is hydroxyl, alkoxy, amino or substituted amino;
Y is H or acetyl;
$R^1$ is H or methyl; and
wherein the terminal nitrogen of abiotic oligomer is attached to Y; and the terminal carbonyl carbon, —C(=O)—, of the abiotic oligomer is attached to the nitrogen of the serine or threonine residue;
provided that the hybrid polymer is other than HP1, HP2, HP3, HP4, HP5, or HP6.

3. The hybrid polymer according to claim 1, wherein the hybrid polymer is according to formula II:

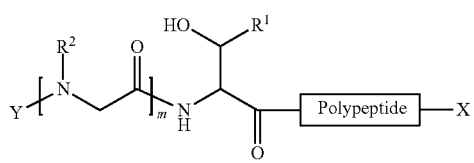

or a pharmaceutically acceptable salt, stereoisomer, isotopic variant or tautomer thereof;
wherein
X is hydroxyl, alkoxy, amino or substituted amino;
Y is H or acetyl;
$R^1$ is H or methyl;
each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl; and
the subscript m is an integer from 2-200;
provided that the hybrid polymer is other than HP1, HP2, HP3, HP4, HP5, or HP6.

4. The hybrid polymer according to claim 1, wherein the hybrid polymer is according to formula III:

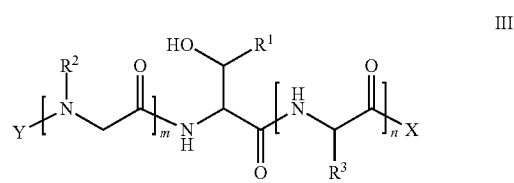

or a pharmaceutically acceptable salt, stereoisomer, isotopic variant or tautomer thereof;
wherein
X is hydroxyl, alkoxy, amino or substituted amino;
Y is H or acetyl;
$R^1$ is H or methyl;
each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
each $R^3$ is independently selected from a group consisting of H, substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
the subscript m is an integer from 2-200; and the subscript n is an integer from 2-1000;
provided that the oligomer is other than HP1, HP2, HP3, HP4, HP5, or HP6.

5. A pharmaceutical composition comprising a pharmaceutically acceptable carrier and a pharmaceutically effective amount of the hybrid polymer of claim 1.

6. A compound according to formula SI-5:

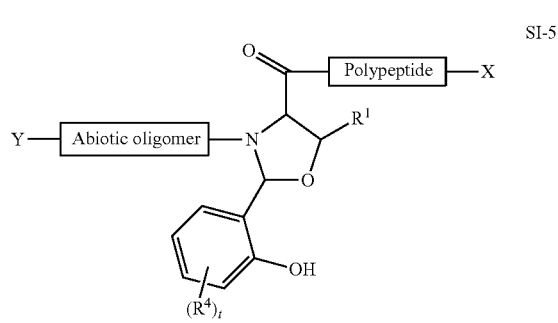

or a stereoisomer, or a tautomer thereof;
wherein
Abiotic oligomer is selected from N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas, and combinations thereof;

X is hydroxyl, alkoxy, amino or substituted amino;
Y is H or acetyl;
$R^1$ is H or methyl;
each $R^4$ is independently H or substituted or unsubstituted alkyl; and
wherein the terminal nitrogen of the abiotic oligomer is attached to Y; and the terminal carbonyl carbon, —C(=O)—, of the abiotic oligomer is attached to the nitrogen of oxazolidine.

7. The compound of claim 6, wherein the compound is according to formula SI-5-1:

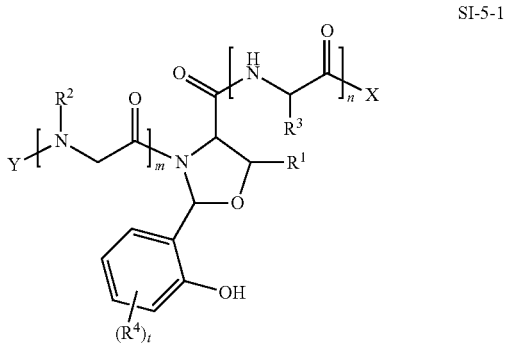

or a stereoisomer, or a tautomer thereof;
wherein
X is hydroxyl, alkoxy, amino or substituted amino;
Y is H or acetyl;
$R^1$ is H or methyl;
each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
each $R^3$ is independently selected from a group consisting of H, substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
each $R^4$ is independently H or substituted or unsubstituted alkyl;
and
the subscript m is an integer from 2-200; the subscript n is an integer from 2-1000; and
the subscript t is 1, 2, 3, or 4.

8. The compound according to claim 7, wherein each of $R^2$ or each of $R^3$ is independently phenyl, benzyl, phenethyl, 2-napthyl, 2,2-diphenylethyl, furanyl, thienyl, unsubstituted or substituted with one or more groups selected from alkyl, halo, hydroxy, amino, nitro, and alkoxy.

9. The compound according to claim 7, wherein each of $R^2$ or each of $R^3$ is independently guanidinoalkyl.

10. The compound according to claim 7, wherein each of $R^2$ or each of $R^3$ is independently imidazolylmethyl, 2-imidazolylethyl, 3-imidazolylpropyl, 4-imidazolylbutyl, 5-imidazolylpentyl, or 6-imidazolylhexyl.

11. The compound according to claim 7, wherein each of $R^2$ or each of $R^3$ is independently methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

12. The compound according to claim 7, wherein each of $R^2$ or each of $R^3$ is independently Me, i-Pr, i-Bu, sec-Bu, phenethyl, 4-hydroxyphenethyl, benzimidazol-3-ylmethyl, thiomethyl, methylthioethyl, hydroxymethyl, aminopropyl, guanadinopropyl, or imdazo-4-yl methyl.

13. The compound according to claim 7, wherein t is 4; and each of $R^4$ is H.

14. The compound according to claim 7, wherein the polypeptide comprises more than 100 or between 50-100, or fewer than 50 amino acid residues.

15. The compound according to claim 7, wherein the polypeptide comprises amino acid residues; and the amino acid residues are selected from one or more glycine, L-alanine, L-valine, L-leucine, L-iso-leucine, L-tyrosine, L-proline, L-tyrosine, L-serine, L-glutamic acid, L-tryptophan, L-phenylalanine, L-methionine, L-arginine, and L-histidine residues.

16. The compound according to claim 7, wherein Y is acyl, unsubstituted or substituted with cycloalkyl, or phenyl; or Y is —COCH$_3$.

17. The compound according to claim 7, wherein X is —NH$_2$, —OH, or —O-alkyl.

18. The compound according to claim 7, wherein m is an integer between 2-200, 2-100, 2-50, 2-30, 2-20, 2-10, or 2-5; and n is an integer between 2-1000, 2-500, 2-400, 2-200, 2-100, 2-50, 2-30, 2-20, 2-10, or 2-5.

19. A process for preparing a hybrid polymer according to formula I:

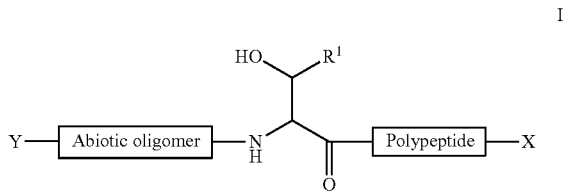

or a pharmaceutically acceptable salt, stereoisomer, isotopic variant or tautomer thereof;
comprising the steps of
A1) reacting the compound of formula SI-1 with salicylaldehyde of formula SI-2

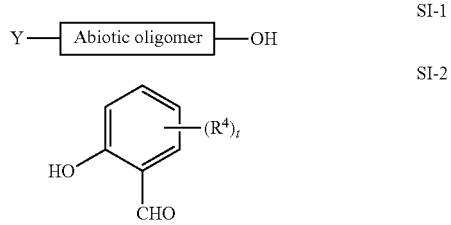

to form a compound of formula SI-3:

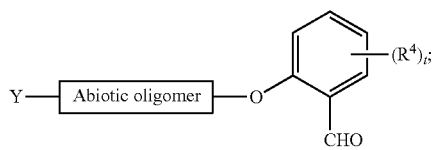

A2) reacting the compound of formula SI-3 with a polypeptide of formula SI-4

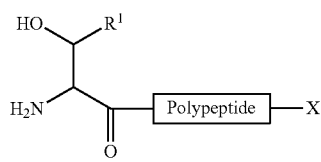

to form the oxazolidine compound of formula SI-5:

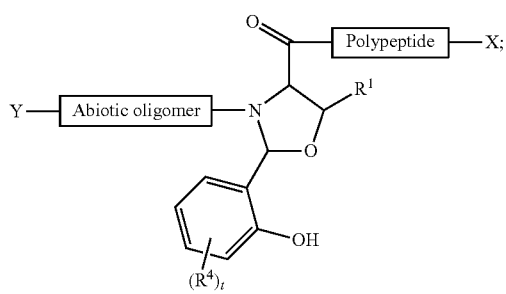

and

A3) reacting the oxazolidine compound of formula SI-5 with an acid to form the hybrid polymer of formula I; wherein Abiotic oligomer is selected from N-substituted glycine peptoid oligomers, beta-peptoids, beta-peptides, alternating alpha/beta peptides, gamma-peptides, pyridine oligoamides, quinoline oligoamides, aryl oligoamides, aedemers, peptide nucleic acids, other abiotic oligoamides, sulfonamidopeptides, aminoxy acid oligomers, hydrazone-linked pyrimidines, oligo-ureidophthalimides, triazine-based oligomers, triazole-based oligomers, oligooxopiperazine oligomers, and oligoureas, and combinations thereof;

X is hydroxyl, alkoxy, amino or substituted amino;

Y is H or acetyl;

$R^1$ is H or methyl;

each $R^4$ is independently H or substituted or unsubstituted alkyl;

and the subscript t is 1, 2, 3, or 4; and wherein in formula I, the terminal nitrogen of the abiotic oligomer is attached to Y; and the terminal carbonyl carbon, —C(=O)—, of the abiotic oligomer is attached to the nitrogen of the serine or threonine residue.

20. The process for preparing a hybrid polymer according to claim 19, wherein the polymer of formula I is a polymer of formula III:

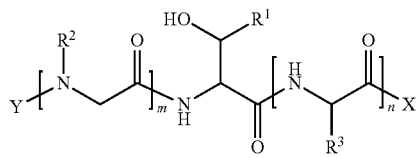

or a pharmaceutically acceptable salt, stereoisomer, isotopic variant or tautomer thereof;

the process comprises the steps of

B1) reacting the compound of formula SI-1-1 with salicylaldehyde of formula SI-2

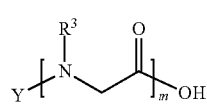

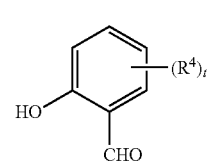

to form a compound of formula SI-3-1:

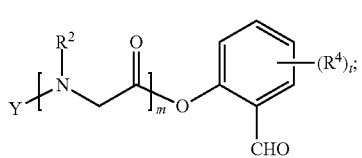

B2) reacting the compound of formula SI-3-1 with a polypeptide of formula SI-4-1

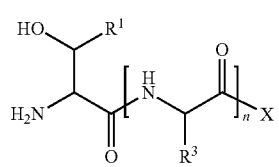

to form the oxazolidine compound of formula SI-5-1:

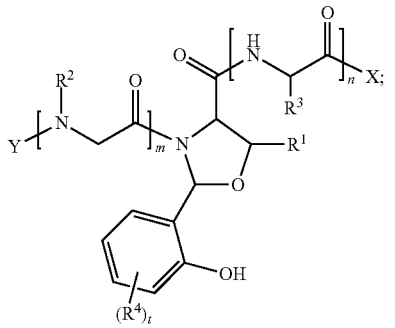

SI-5-1 and

B3) reacting the oxazolidine compound of formula SI-5-1 with an acid to form the hybrid polymer of formula III;
wherein
X is hydroxyl, alkoxy, amino or substituted amino;
Y is H or acetyl;

$R^1$ is H or methyl;

each $R^2$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;

each $R^3$ is independently selected from a group consisting of H, substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;

each $R^4$ is independently H or substituted or unsubstituted alkyl;

and the subscript m is an integer from 2-200; the subscript n is an integer from 2-1000;

the subscript t is 1, 2, 3, or 4.

* * * * *